United States Patent
Vasudevan et al.

(12)

(10) Patent No.: US 6,720,423 B2
(45) Date of Patent: Apr. 13, 2004

(54) DIHYDROBENZOFURAN AND DIHYDROBENZOTHIOPHENE 2,4-PENTADIENOIC ACID DERIVATIVES HAVING SELECTIVE ACTIVITY FOR RETINOID X (RXR) RECEPTORS

(75) Inventors: Jayasree Vasudevan, Anaheim, CA (US); Dehua Huang, San Diego, CA (US); Vidyasagar Vuligonda, Irvine, CA (US); Roshanta S. Chandraratna, Laguna Hills, CA (US)

(73) Assignee: Allergan, Inc., Irvine, CA (US)

( * ) Notice: Subject to any disclaimer, the term of this patent is extended or adjusted under 35 U.S.C. 154(b) by 9 days.

(21) Appl. No.: 10/135,595

(22) Filed: Apr. 30, 2002

(65) Prior Publication Data

US 2003/0216570 A1 Nov. 20, 2003

(51) Int. Cl.$^7$ .................. A61K 31/34; A61K 31/38; C07D 307/79; C07D 333/54

(52) U.S. Cl. ................ 546/281.1; 546/284.1; 549/51; 549/57; 549/58; 549/462

(58) Field of Search ............... 549/462, 51, 57, 549/58; 546/281.1, 284.1

(56) References Cited

U.S. PATENT DOCUMENTS

| | | | |
|---|---|---|---|
| 4,447,445 A | 5/1984 | Jacobs et al. | |
| 4,943,589 A | 7/1990 | Crews et al. | |
| 5,162,365 A | 11/1992 | Chinn et al. | |
| 5,208,364 A | 5/1993 | Ohkuma et al. | |
| 5,324,840 A | 6/1994 | Chandraratna | 546/318 |
| 5,344,959 A | 9/1994 | Chandraratna | 560/100 |
| 5,455,265 A | 10/1995 | Chandraratna | 514/448 |
| 5,466,861 A | 11/1995 | Dawson et al. | 562/490 |
| 5,563,292 A | 10/1996 | Shih et al. | |
| 5,648,376 A | 7/1997 | Strobel et al. | |
| 5,675,033 A | 10/1997 | Vuligonda et al. | 560/100 |
| 5,728,846 A | 3/1998 | Vuligonda | 549/16 |
| 5,877,207 A | 3/1999 | Klein et al. | 514/456 |
| 5,917,082 A | 6/1999 | Vuligonda et al. | 560/100 |
| 6,034,110 A | 3/2000 | Nagpal | 514/350 |
| 6,048,873 A | 4/2000 | Vasudevan et al. | 514/311 |
| 6,069,146 A | 5/2000 | Fenical et al. | |
| 6,093,838 A | 7/2000 | Vasudevan et al. | 549/467 |
| 6,147,224 A | 11/2000 | Vuligonda et al. | 548/518 |
| 6,172,115 B1 | 1/2001 | Chandraratna | 514/569 |

FOREIGN PATENT DOCUMENTS

| | | |
|---|---|---|
| EP | 0098591 | 7/1983 |
| WO | WO9311755 | 6/1993 |
| WO | WO9321162 | 10/1993 |
| WO | WO9605165 | 7/1995 |
| WO | WO9503021 | 2/1996 |
| WO | WO 98/00168 | 1/1998 |
| WO | WO 98/01134 | 1/1998 |

OTHER PUBLICATIONS

Jaspara, et al, "The Cyclorenierins, Sesquiterpenoid Quinols from the Sponge Haliclona SP. Collected in Vanuatu"; Journal of Natural Products, vol. 58, No. 4, pp. 609–612; Apr. 1995.

De Vries, et al, "Preferenctal Inhibition of 5–Lipoxygenase Activity by Manoalide"; Biochemical Pharmacology, vol. 37, No. 15. pp. 2899–2905, 1988.

Cabre'et al, "Effect of Manolalide on Human 5–lipoxygenase Activity", Inflamm Re. 45: 218–223(1996); Original Research Paper.

Look, et al, The Pseudopterosins: A New Class of Antiinflammatory and Analgesic Diterpene Pentosides from the Marine Sea Wip *Pseudopterogorgia elisabethae* (Octocorallia); J. Org. Chem. 1986, 51, pp. 5140–5145.

Muyer, et al, Pharmacological Characterization of the Pseudopterosins: Novel Anti–Inflammatory Natural Products Isolated from the Caribbean Soft Coral, *Pseudopterogorgia elisabethae*; Life Sciences, vol. 62. No. 26, pp. Pl. 401–407, 1998.

Jacobson, et al., "Fuscoside: An Anti–Inflammatory Marine Natural Product which Selectively Inhibits 5–Lipoxygenase. Part I: Physiological and Biochemical Studies in Murine Inflammatory Models", The Journal of Pharmacology and Experimental Therapeutics, vol. 262. No. 2 pp. 866–873.

Kazlauskas, et al., "Heteronemin, A New Scalarin Type Sesterterpene for the Sponge *Heteronema Erecta*", Tetrahedron Letters, No. 30, pp. 2631–2634, 1976.

Hoang Tran, et al., New Oxygenated Sesquiterpenes from a Southern Australian Marine Sponge, Dictyodendrilla sp. Aust. J. Chem, 1995, 48, pp. 1757–1760.

Fu, et al., Halisulfate 7, a New Sesterterpene Sulfate from a Sponge, Coscinoderma sp. J. Nat. Prod. 1999, 62, pp. 1190–1191.

Murray, et al. "Geographic Variation in the Tropical Marine Sponge Jaspis cf. johnstoni: An Unexpected Source of New Terpene–Benzenoids" J. Org. Chem 1997, 62, pp. 5638–5641.

Verma & Boutwell, Cancer Research 1977, vol. 37, pp. 2196–2201, Jul. 1977.

(List continued on next page.)

Primary Examiner—Bernard Dentz
(74) Attorney, Agent, or Firm—Gabor L. Szekeres; Robert J. Baran; Martin A. Voet

(57) ABSTRACT

Compounds of the formula

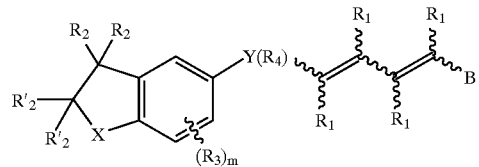

where the variables have the meaning defined in the specification, are specific or selective agonists of RXR retinoid receptors.

54 Claims, No Drawings

OTHER PUBLICATIONS

Allegretto et al. J. Biol. Chem. 268, 26625–26633.

Chen et al. Molecular and Cellular Biology, Aug. 1987, Vol 7, No. 8, pp. 2745–2752.

Cheng et al. Biochemical Pharmacology vol. 22 pp 3099–3108.

Dawson, et al. "Chemistry and Biology of Synthetic Retinoids", published by *CRC Press, Inc.*, (1990), pp. 324–356.

De Wet et al. Molecular and Cellular Biology, Feb. 1987, vol. 7, No. 2, pp. 725–737.

Felger et al. Spring 1989 Focus 11:2, pp. 21–24.

Heyman et al. Cell 68, 397–406, (Jan. 24, 1992).

Iida et al. Tetrahedron Letters, vol. 23, No. 35, pp 3591–3594, 1982 Printed in Great Britain, Pergamon Press Ltd.

Janusz et al. J. Med. Chem. 1998, 41, 1124–1137.

Klein et al. *The Journal of Biological Chemistry* vol. 271, No. 37, Sep 13, pp 22692–22696, 1996.

Mangelsdorf et al. The Retinoids: Biology, Chemistry and Medicine, pp 319–349, Raven Press Ltd., New York.

Vuligonda et al. Bioorganic & Medicinal Chemistry Letters, vol. 6 No. 2, pp. 213–218, 1996.

DIHYDROBENZOFURAN AND DIHYDROBENZOTHIOPHENE 2,4-PENTADIENOIC ACID DERIVATIVES HAVING SELECTIVE ACTIVITY FOR RETINOID X (RXR) RECEPTORS

BACKGROUND OF THE INVENTION

1. Field of the Invention

The present invention relates to novel compounds having retinoid-like biological activity. More specifically, the present invention relates to dihydrobenzofuranyl and dihydrobenzothienyl-cycloalkyl or cycloalkenyl-2,4-pentadienoic acid derivatives and to dihydrobenzofuranyl and dihydrobenzothienyl aryl or heteroaryl 2,4-pentadienoic acid derivatives having selective activity for retinoid X (RXR) receptors.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as agents to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis. Retinoid compounds have relatively recently been also discovered to be useful for treating type II non-insulin dependent diabetes mellitus (NIDDM).

It is now general knowledge in the art that two main types of retinoid receptors exist in mammals (and other organisms). The two main types or families of receptors are respectively designated the RARs and RXRs. Within each type there are subtypes; in the RAR family the subtypes are designated $RAR_\alpha$, $RAR_\beta$ and $RAR_\gamma$, in RXR the subtypes are: $RXR_\alpha$, $RXR_\beta$ and $RXR_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist) or the compound may elicit an agonist-like response on all receptor subtypes (pan-agonist). As still another alternative a compound may be a selective agonist and/or selective antagonist of certain receptor subtypes if the compound binds to but does not activate certain receptor subtype or subtypes but elicits an agonist-like response in other receptor subtype or subtypes. A pan-antagonist is a compound that binds to all known retinoid receptors but does not elicit an agonist-like response in any of the receptors.

Recently a two-state model for certain receptors, including the above-mentioned retinoid receptors, have emerged. In this model, an equilibrium is postulated to exist between inactive receptors and spontaneously active receptors which are capable of coupling with a G protein in the absence of a ligand (agonist). In this model, so-called "inverse agonists" shift the equilibrium toward inactive receptors, thus bringing about an overall inhibitory effect. Neutral antagonists do not effect the receptor equilibrium but are capable of competing for the receptors with both agonists (ligands) and with inverse agonists. U.S. Pat. No. 5,877,207 titled "Synthesis and Use of Retinoid Compounds Having Negative Hormone and/or Antagonist Activities" describes the foregoing two-state model and the use of retinoid antagonist and negative hormones in detail.

Among the scientific publications Dawson and William H. Okamura, *Chemistry and Biology of Synthetic Retinoids*, published by CRC Press Inc., 1990, pages 334–335, 354 and 324–356 is of special interest as an overview of the prior art on the subject.

The following is a list of United States and foreign patents and publications which disclose compounds having structural similarity to the compounds of the present invention, or disclose compounds having retinoid agonist, antagonist or inverse agonist like biological activity having a benzofuran, indole, benzothiophene or closely related moiety or a pentadienoic acid moiety: U.S. Pat. Nos. 6,172,115; 6,048,873; 6,034,110; 5,917,082; 6,093,838; 5,675,033; 6,147,224; 5,728,846; 5,324,840; 5,344,959; 5,466,861; WO 96/05165; WO 93/21162; EPO 0 098 591; Janusz et al. J. Med. Chem. 1998 41 1124–1137; Iida et al. Tetrahedron Letters 35, 1982 p 3591–3594; Vuligonda et al. Bioorg. Med. Chem. Lett. 6 (2) 213–8, 1996.

SUMMARY OF THE INVENTION

The present invention relates to compounds of Formula 1

Formula 1

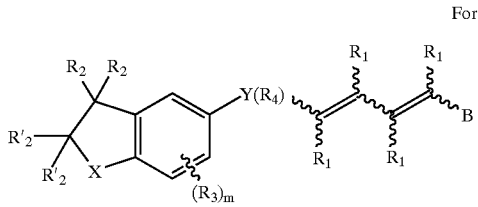

where X is O or S;

Y is a bivalent cycloalkyl or cycloalkenyl radical optionally substituted with one to four $R_4$ groups, the cycloalkenyl radical having 5 or 6 carbons and one double bond, or Y is a bivalent aryl or 5 or 6 membered heteroaryl radical having 1 to 3 heteroatoms selected from N, S and O, said aryl or heteroaryl groups optionally substituted with 1 to 4 $R_4$ groups;

$R_1$ is independently H, alkyl of 1 to 6 carbons, or fluoroalkyl of 1 to 6 carbons;

$R_2$ is independently H, alkyl of 1 to 8 carbons, or fluoroalkyl of 1 to 8 carbons;

$R'_2$ is independently H, alkyl of 1 to 8 carbons, or fluoroalkyl of 1 to 8 carbons;

$R_3$ is hydrogen, alkyl of 1 to 10 carbons, fluoro substituted alkyl of 1 to 10 carbons, halogen, alkoxy of 1 to 10 carbons, or alkylthio of 1 to 10 carbons; $NO_2$, $NH_2$, $NHCO(C_1-C_6$ alkyl), $NHCO(C_1-C_6)$alkenyl, $NR_1H$ or $N(R_1)_2$, benzyloxy, $C_1-C_6$alkyl-substituted benzyloxy, hydroxyalkyl of 1 to 10 carbons, or $R_3$ is selected from the groups shown below,

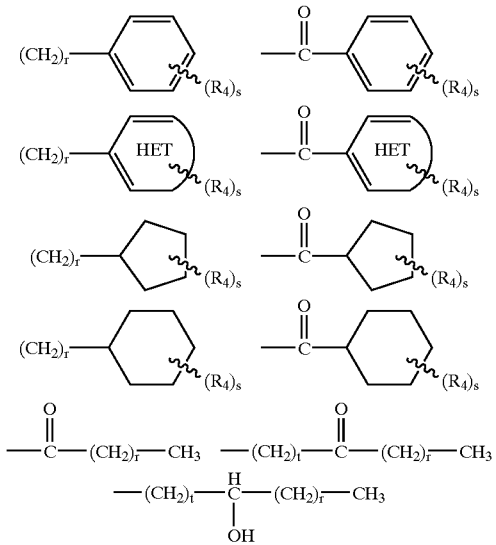

$R_4$ is H, halogen, alkyl of 1 to 10 carbons, fluoro substituted alkyl of 1 to 6 carbons, alkoxy of 1 to 10 carbons, or alkylthio of 1 to 10 carbons;

m is an integer having the values of 0 to 3;
r is an integer having the values of 1 to 10;
s is an integer having the values 1 to 4;
t is an integer having the values 1 to 5;

represents a 5 or 6 membered heteroaryl ring having 1 to 3 heteroatoms selected from the group consisting of N, S and O;

B is COOH or a pharmaceutically acceptable salt thereof, $COOR_8$, $COOCH_2COR_7$, $CONR_9R_{10}$, $-CH_2OH$, $CH_2OR_{11}$, $CH_2OCOR_{11}$, CHO, $CH(OR_{12})_2$, $CH(OR_{13}O)$, $-COR_7$, $CR_7(OR_{12})_2$, $CR_7(OR_{13}O)$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, $CH_2OCOR_{12}$, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl, hydroxyphenyl or lower alkylphenyl, $R_{11}$ is alkyl of 1 to 6 carbons, phenyl or lower alkylphenyl, $R_{12}$ is alkyl of 1 to 6 carbons, and $R_{13}$ is divalent alkyl radical of 2–5 carbons.

In a second aspect, this invention relates to the use of the compounds of Formula 1 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, atopic dermatitis, Darriers disease, lichen planus, prevention and reversal of glucocorticoid damage (steroid atrophy), as a topical antimicrobial, as skin anti-pigmentation agents and to treat and reverse the effects of age and photo damage to the skin. The compounds are also useful for the prevention and treatment of metabolic diseases such as type II diabetes and diabetes mellitus and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other comeopathies, as well as in the treatment and prevention of various cardiovascular diseases, including, without limitation, diseases associated with lipid metabolism such as dyslipidemias, prevention of post-angioplasty restenosis and as agents to increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil®, diseases associated with the immune system, including use of the present compounds as immunosuppressants and immunostimulants, modulation of organ transplant rejection and facilitation of wound healing, including modulation of chelosis.

Generally speaking, the second aspect of the invention relates to the use of the novel compounds to prevent or treat diseases and conditions which are responsive to compounds that promote the expression of or bind to receptors belonging to the steroid or thyroid receptor superfamily.

This invention also relates to a pharmaceutical formulation comprising a compound of Formula 1 in admixture with a pharmaceutically acceptable excipient, said formulation being adapted for administration to a mammal, including a human being, to treat or alleviate the conditions which were described above as treatable by retinoids.

Biological Activity, Modes of Administration
Assays of Retinoid-Like Biological Activity A classic measure of retinoic acid activity involves measuring the effects of retinoic acid on ornithine decarboxylase. The original work on the correlation between retinoic acid and a decrease in cell proliferation was done by Verma & Boutwell, Cancer Research, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Research: 1662–1670,1975 may be used to demonstrate inhibition of TPA induction of ODC by compounds of this invention. "$IC_{60}$" is that concentration of the test compound which causes 60% inhibition in the ODC assay. By analogy, "$IC_{80}$", for example, is that concentration of the test compound which causes 80% inhibition in the ODC assay.

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a $K_d$ value of less than approximately 1 micromolar. In the below described assays the ability of the compounds to bind to $RAR_\alpha$, $RAR_\beta$, $RAR_\gamma$, $RXR_\alpha$, $RXR\beta$ and $RXR_\gamma$ receptors, and the ability or inability of the compounds to activate transcription of a reporter gene through these receptor subtypes can be tested. These assays are expected to demonstrate that the compounds of the present invention act as agonists of one or more of the above-described receptors. Because of the complex distribution of the different retinoid receptors in various organs of the mammalian body subtype selective agonists may lend themselves to particularly useful therapeutic applications and may avoid serious side effects of conventional retinoid drugs.

As far as specific assays are concerned to demonstrate the activities of the compounds of the present invention, a chimeric receptor transactivation assay which tests for agonist-like activity in the $RAR_\alpha$, $RAR_\beta$, $RAR_\gamma$, $RXR_\alpha$, receptor subtypes, and which is based on work published by Feigner P. L. and Holm M (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO93/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in $EC_{50}$ numbers, as they are also in the chimeric receptor transactivation assay. The results of ligand binding assay are expressed in $K_d$ numbers. (See Cheng et al. Biochemical Pharmacology Vol. 22 pp 3099–3108, expressly incorporated herein by reference.)

Still another transactivation assay, the "PGR assay" is described in the publication Klein et al. J. Biol. Chem. 271, 22692–22696 (1996) which is expressly incorporated herein by reference, and a detailed description is also provided below. The results of the PGR assay are also expressed in $EC_{50}$ numbers (nanomolar concentration).

CV-1 cells ($4 \times 10^5$ cells/well) were transiently transfected with the luciferase reporter plasmid MTV-4 (R5G)-Luc (0.7 ug/well) containing four copies of the R5G retinoid DNA response element along with the RXRα expression plasmid pRS-hRXRα (0.1 ug/well) and one of the RAR-P-GR expression plasmids (0.05 ug/well) in 12 well plates via calcium phosphate precipitation Chen et al. (1987) Mol. Cell. Biol. 7, 2745–2752 as described by Klein et al. in J. Biol. Chem. 271, 22692, referenced above. The three different RAR-P-GR expression plasmids, pRS-RARα-P-GR, pcDNA3-RARβ-P-GR and pcDNA3-RARγ-P-GR, express RARα, RARβ and RARγ receptors, respectively, which contain modified DNA binding domains such that their "P-boxes" have been altered to that of the glucocorticoid receptor. These RAR-P-GR receptors bind to DNA as heterodimeric complexes with RXR. Specifically, the RAR-P-GR receptors bind retinoic acid response elements designated R5G, comprised of two RAR half sites (nucleotide sequence 5'-GGTTCA-3') separated by 5 base pairs in which the 3'-half site has been modified to that of a glucocorticoid receptor half site, 5'-AGAACA-3'. To allow for various in transfection efficiency a β-galactosidase expression plasmid (0.01 ug/well) was used as an internal control. Alternatively, the assay was performed in a 96-well microtiter plate format (5000 cells/well) in a manner which was identical to that described above except ⅕ of the amount of the DNA-calcium phosphate precipitant (20 µl instead of 100 µl) was applied to each well. Eighteen hours after introduction of the DNA precipitants, cells were rinsed with phosphate buffered saline (PBS) and fed with D-MEM (Gibco-BRL) containing 10% activated charcoal extracted fetal bovine serum (Gemini Bio-Products). Cells were treated for 18 hours with the compounds indicated in the figures. After rinsing with PBS cells were lysed and luciferase activity was measured as previously described in de Wet (1987) Mol. Cell. Biol. 7, 725–737. Luciferase values represent the mean±SEM of triplicate determinations normalized to β-galactosidase activity.

Table 1 discloses the activity of certain exemplary compounds of the invention in the above-described chimeric receptor transactivation and ligand binding assays. Table 1 also discloses the most preferred compounds of the invention, shown in their free carboxylic acid form. In the chimeric receptor transactivation assay the compounds were essentially inactive in activating RARα, RARβ and RARγ receptors.

TABLE 1

| Compound No. | Structure | RAR Trans. $EC_{50}$ (nM) RAR Bind. $K_i$ (nM) | | | RXR Trans. $EC_{50}$ (nM) RXR Bind $K_i$ (nM) | | |
|---|---|---|---|---|---|---|---|
| | | α | β | γ | α | β | γ |
| 2 | 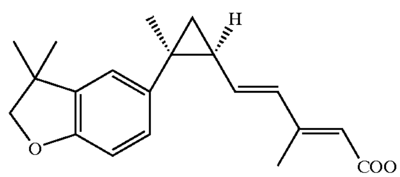 | NA >10K | NA >10K | NA >10K | 1.1 (110) 7.8 | 9.8 (106) 21.1 | 2.7 (119) 35 |
| 4 | 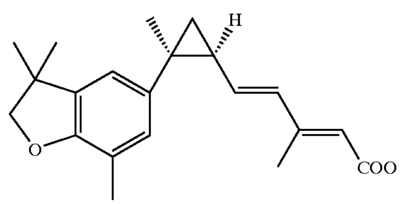 | NA >10K | NA >10K | NA >10K | 2.9 (106) 6.3 | 21 (108) 74 | 4.4 (108) 9.9 |
| 6 | 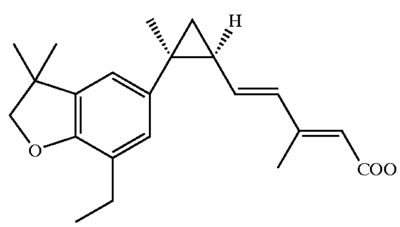 | NA >30K | NA >30K | NA 13K | 0.3 (83) 0.72 | 2.8 (75) 1.8 | 0.56 (85) 3.2 |
| 8 | 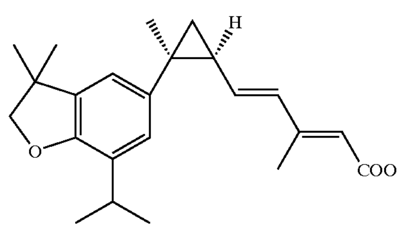 | NA 42K | NA 41K | NA 7515 | 0.159 (111) 1.7 | 0.66 (110) 10.6 | 0.23 (108) 8.6 |
| 10 | 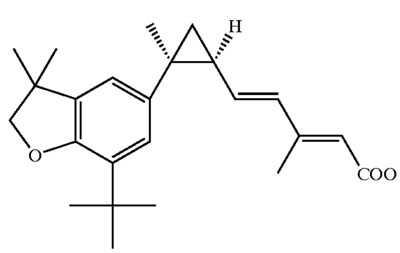 | NA 11K | NA 19K | NA 13K | 0.55 (110) 0.8 | 12 (90) 7.1 | 0.78 (95) 1.3 |

TABLE 1-continued

| Compound No. | Structure | RAR Trans. EC$_{50}$ (nM) RAR Bind. K$_i$ (nM) | | | RXR Trans. EC$_{50}$ (nM) RXR Bind K$_i$ (nM) | | |
|---|---|---|---|---|---|---|---|
| | | α | β | γ | α | β | γ |
| 22 | 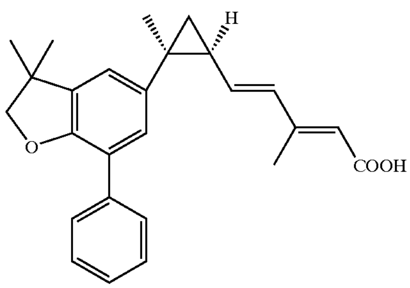 | NA >10K | NA >10K | NA >5257 | 8.3 (115) 2.3 | 28.4 (75) 9.6 | 12.8 (110) 6.2 |
| 12 | 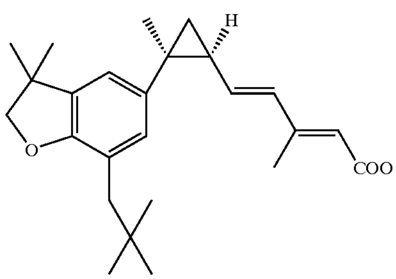 | NA 18K | NA 9510 | NA 8911 | 0.246 (92) 0.2 | 1.67 (93) 1.5 | 0.42 (101) 0.7 |
| 14 | 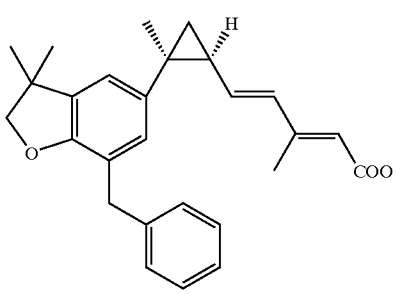 | NA 8722 | NA 4768 | NA 6651 | 0.086 (109) 0.8 | 0.515 (114) 1.1 | 0.0973 (105) 9.2 |
| 18 | 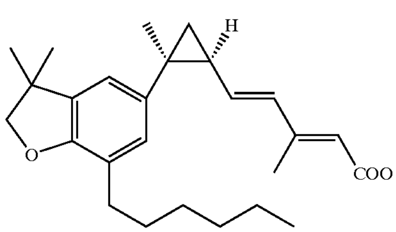 | NA 12K | NA 15K | NA 9263 | 0.25 (91) 1.9 | 2.8 (96) 5.1 | 0.36 (99) 2 |
| 20 | 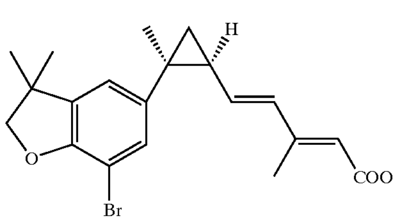 | NA >10K | NA >10K | NA >10K | 2.4 (95) 7.1 | 12 (108) 21.5 | 3.4 (111) 40 |

TABLE 1-continued

| Compound No. | Structure | RAR Trans. EC$_{50}$ (nM) / RAR Bind. K$_i$ (nM) | | | RXR Trans. EC$_{50}$ (nM) / RXR Bind K$_i$ (nM) | | |
|---|---|---|---|---|---|---|---|
| | | α | β | γ | α | β | γ |
| 26 | 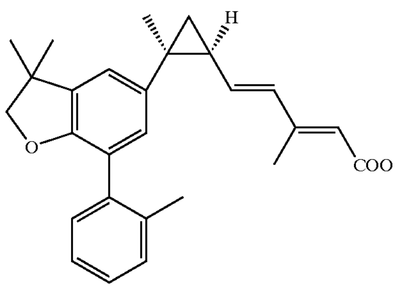 | NA<br>>10K | NA<br>>10K | NA<br>>10K | 0.2<br>(106)<br>1.2 | 0.65<br>(99)<br>1.9 | 0.32<br>(107)<br>6.1 |
| 24 | 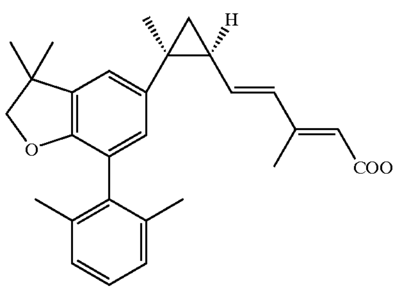 | NA<br>>10K | NA<br>>10K | NA<br>>10K | 0.52<br>(106)<br>0.7 | 6.7<br>(125)<br>2.6 | 0.86<br>(105)<br>4.8 |
| 30 | 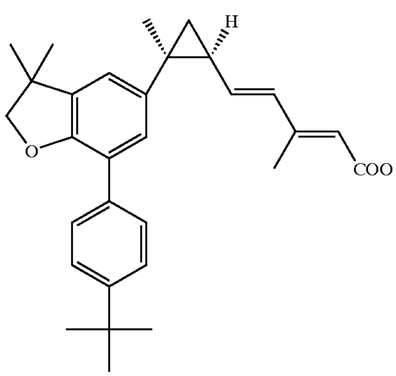 | NA<br>>10K | NA<br>>10K | NA<br>>10K | 1517<br>(85)<br>129 | >1K<br>(50)<br>441 | >1K<br>(80)<br>69.9 |
| 28 | 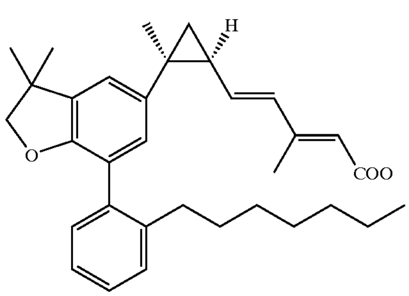 | NA<br>2621 | NA<br>3744 | NA<br>9544 | 594<br>(86)<br>35 | >1000<br>111 | 850<br>(88)<br>ND |
| 36 | 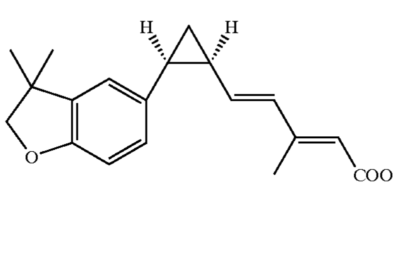 | NA<br>>10K | NA<br>>10K | NA<br>>10K | 609<br>(114)<br>114 | >1000<br>312 | 743<br>(109)<br>602 |

TABLE 1-continued

| Compound No. | Structure | RAR Trans. EC$_{50}$ (nM) RAR Bind. K$_i$ (nM) | | | RXR Trans. EC$_{50}$ (nM) RXR Bind K$_i$ (nM) | | |
|---|---|---|---|---|---|---|---|
| | | α | β | γ | α | β | γ |
| 40 | 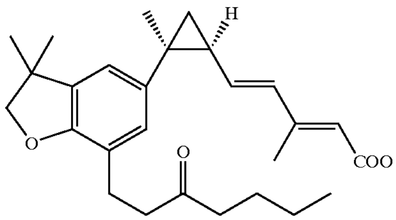 | NA 11K | NA 22K | NA >10K | 330 (102) 41 | 2043 (103) 69 | 395 (94) 70 |
| 38 | 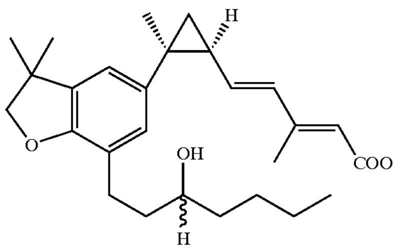 | NA >10K | NA >10K | NA >10K | 1949 (102) 306 | 1355 557 | 7684 (142) 283 |
| 16 | 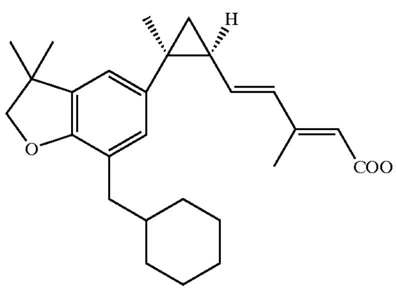 | NA 8798 | NA 9294 | NA 12K | 0.215 (92) 0.3 | 1.15 (85) 1.9 | 0.29 (83) 1.9 |
| 34 | 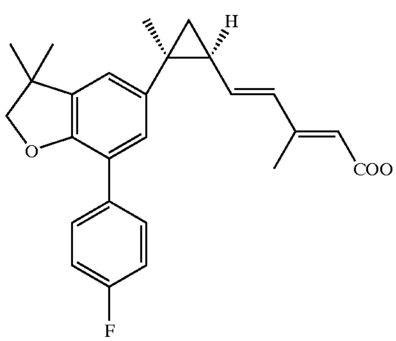 | NA 23K | NA 8746 | NA 25K | 0.37 (105) 0.5 | 4.55 (93) 4 | 0.56 (109) 1.5 |
| 32 | 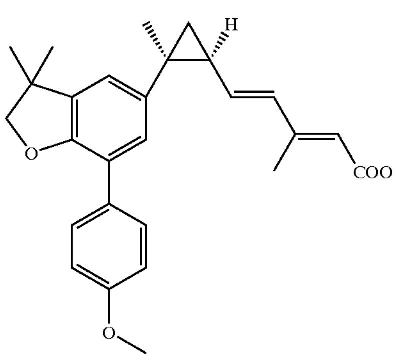 | NA 29K | NA 15K | NA >10K | 581 (105) 66 | >1000 926 | 561 (106) 227 |

As it can be seen from the foregoing assay results, the compounds of the invention are specific or selective agonists of RXR receptors.

Modes of Administration

The compounds of this invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pa. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection. Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg of body weight per day would be expected to effect a therapeutic result in the treatment of many diseases for which these compounds are useful.

General Embodiments and Synthetic Methodology

Definitions

The term alkyl refers to and covers any and all groups which are known as normal alkyl, branched-chain alkyl, cycloalkyl and also cycloalkyl-alkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Unless specified otherwise, lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo-lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1 is —COOH, this term covers the products derived from treatment of this function with alcohols or thiols preferably with aliphatic alcohols having 1–6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$, is a variable as defined above in connection with Formula 1.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

The term amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula-CK where K is (—OR)$_2$. Here, R is lower alkyl. Also, K may be —OR$_7$O— where R$_7$ is lower alkyl of 2–5 carbon atoms, straight chain or branched.

A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The compounds of the present invention are capable of existing as trans and cis (E and Z) isomers relative to olephinic double bonds, cycloalkyl rings and particularly and in case of the preferred compounds relative to the cyclopropane ring. The invention covers trans as well as cis isomers relative to each center that gives rise to such isomerism. However for certain preferred compounds specific orientation of substituents relative to a double bond or the ring is indicated in the name of the respective compound, and/or by specific showing in the structural formula of the orientation of the substituents relative to the double bond or ring.

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well.

Reaction Scheme 1 discloses a general and nevertheless presently preferred synthetic route to a class of preferred compounds of the invention where the variable Y of Formula 1 represents a bivalent cyclopropyl radical, the variable X is O or S (dihydrobenzofuran and dihydrobenzothiophen derivatives) and where the 2,2' position of dihydrobenzofuran or of dihydrobenzothiophen is unsubstituted. Referring now to this scheme, the starting compound in this synthetic route is a compound of Formula 2, which is a 4-bromo (or other halogeno)-phenol or corresponding thiophenol substituted with the $R_3$ group, or groups. (The variable $R_3$ and m are defined as in connection with Formula 1.) Compounds of Formula 2 are available commercially and/or can be prepared in accordance with the chemical literature, or by such modifications of known synthetic procedures which are readily apparent to those skilled in the art. In the ensuing description the scheme is described with primary reference to the preparation of dihydrobenzofuran compounds because these are the most preferred embodiments, however it should be kept in mind that the corresponding dihydrobenzothiophen derivatives can be prepared in the same manner with intermediates where the variable X is S (sulfur).

Thus, the 4-bromophenol derivative of Formula 2 is reacted with a 3-chloro-2-methylpropene derivative of Formula 3. In Formula 3 the variable $R_2$ is defined as in connection with Formula 1 and the variable $R_{2(-1)}$ is defined as the variable $R_2$ minus one methylene group and can be just a H. Compounds of Formula 3 are available commercially and/or can be prepared in accordance with the chemical literature, or by such modifications of known synthetic procedures which are readily apparent to those skilled in the art. An example of a reagent of Formula 3 which is utilized for the synthesis of several preferred compounds of the invention is 3-chloro-2-methylpropene. The reaction between the 4-bromophenol derivative of Formula 2 and the 3-chloro-2-methylpropene derivative of Formula 3 is conducted under Friedel Crafts conditions (e.g. in concentrated sulfuric acid) to provide 4-bromo-2-(2-chloro-1,1-dialkyl-ethyl)phenol (or thiophenol) compounds of Formula 4. In the most preferred compounds of the invention the $R_2$ groups are methyl. The compound of Formula 4 is ring closed with strong base in an aprotic solvent (sodium hydride in tetrahydrofuran (THF)) to give the 5-bromo-3,3-dialkyl-2,3-dihydro-benzofuran derivative of Formula 5.

The 5-bromo-3,3-dialkyl-2,3-dihydro-benzofuran derivative of Formula 5 is then reacted with t-butyllithium in n-pentane and trimethyl borate is added to the resulting solution to give a 3,3-dialkyl-2,3-dihydro-benzofuran-5-boronic acid derivative or the corresponding dihydrobenzothiophene derivative of Formula 6. The 3,3-dialkyl-2,3-dihydro-benzofuran-5-boronic acid derivative of Formula 6 is heated with 3-iodo-but-2 (Z)-ene-ol of Formula 7, in the presence of tetrakis(triphenyl-phosphine)palladium(0) (Pd (PPh$_3$)$_4$) and potassium carbonate in a mixture of methanol, toluene and water under an argon atmosphere. Although the reaction scheme illustrates 3-iodo-but-2 (Z)-ene-ol because this reagent is used for the synthesis of the presently preferred compounds of the invention, it should be understood that further alkyl substituted derivatives of 3-iodo-but-2 (Z)-ene-ol can also be used to provide alternative embodiments of this class of preferred compounds of the invention where the cyclopropyl ring is substituted with alkyl groups other than in the below shown preferred embodiments.

After work-up with sodium carbonate a 3,3-dialkyl-5-(3-hydroxy-1-methyl-prop-(1Z)-enyl)-2,3-dihydro-benzofuran derivative of Formula 8 is obtained. The compound of Formula 8 is converted into the 3,3-dialkyl-5-[(1S,2 S)-3-hydroxy-1,2-methano-1-methyl-propyl]-2,3-dihydro-benzofuran derivative of Formula 9 by treatment with diethylzinc and diiodomethane in anhydrous dichloromethane in the presence of (4S-trans)-2-butyl-N,N,N',N'-tetramethyl[1,3,2]dioxaborolane-[4,5]dicarboxamide (Formula 10) which can be prepared in accordance with the teaching of J. Amer. Chem. Soc. 1998, 120, 11943 (incorporated herein by reference). As is known, the cyclopropylation reaction with diiodomethane preserves the cis or trans stereochemistry of the double bond to which the "CH$_2$" moiety is added. Thus, depending on the cis or trans nature of the reagent of Formula 7 either cis or trans stereochemistry relative to the cyclopropane ring can be obtained. Reaction Scheme 1 shows only one such compound (Formula 9) which is cis. The levorotatory reagent (4S,-trans)-2-butyl-N,N,N,N-tetramethyl[1,3,2-]-dioxaborolane-[4,5]dicarboxamide causes the reaction to provide a mixture of enantiomers wherein one of the two enantiomers predominates but is not the exclusive product. In order to obtain predominantly the other enantiomer, the reagent derived from (R$_1$R)-N,N,N', N'-tetramethlyl tartaramide would be used. In the next few steps of the synthesis of this class of preferred compounds of the invention the compound of Formula 9 is further resolved to provide a predominantly or substantially pure optical isomer. The resolution is conducted through esterification with (1S)-camphanic chloride (Formula 11) to give the corresponding (1S)-camphanate ester of Formula 12 which is thereafter saponified to provide the predominantly or substantially optically pure 3,3-dialkyl-5-[(1S,2S)-3-hydroxy-1,2-methano-1-methyl-propyl]-2,3-dihydro-benzofuran derivative of Formula 13.

The predominantly or substantially optically pure 3,3-dialkyl-5-[(1S,2S)-3-hydroxy-1,2-methano-1-methyl-propyl]-2,3-dihydro-benzofuran derivative of Formula 13 is then oxidized to the "aldehyde level" by treatment with molecular sieves powder, tetra-n-propylammoniumperruthenate (TPAP) and N-methylmorpholine-N-oxide (NMO) to provide a 3,3-dialkyl-5-[(1S,2S)-1,2-methano-1-methyl-3-oxo-propyl]-2,3-dihydro-benzofuran derivative of Formula 14. The aldehyde of Formula 14 is subjected to a Horner Emmons reaction with a diethylphosphono reagent of Formula 15 wherein the $R_1$ group is defined as in connection with Formula 1. A preferred example of the reagent of Formula 15 is ethyl-diethylphosphono-3-methyl-2 (E)butenoate (also known as methyl-3-methyl-4-diethylphosphonocrotonate) which can be obtained in accordance with the chemical literature (*J. Org. Chem.* 1974, Volume 39 page 821). The resulting dihydrobenzofuranyl-cyclopropyl-pentadienoic acid ester derivatives or the corresponding dihydrothiophene derivatives of Formula 16 are compounds within the scope of the present invention. These compounds are also saponified to provide the free pentadienoic acid derivatives (or their salts) of Formula 17.

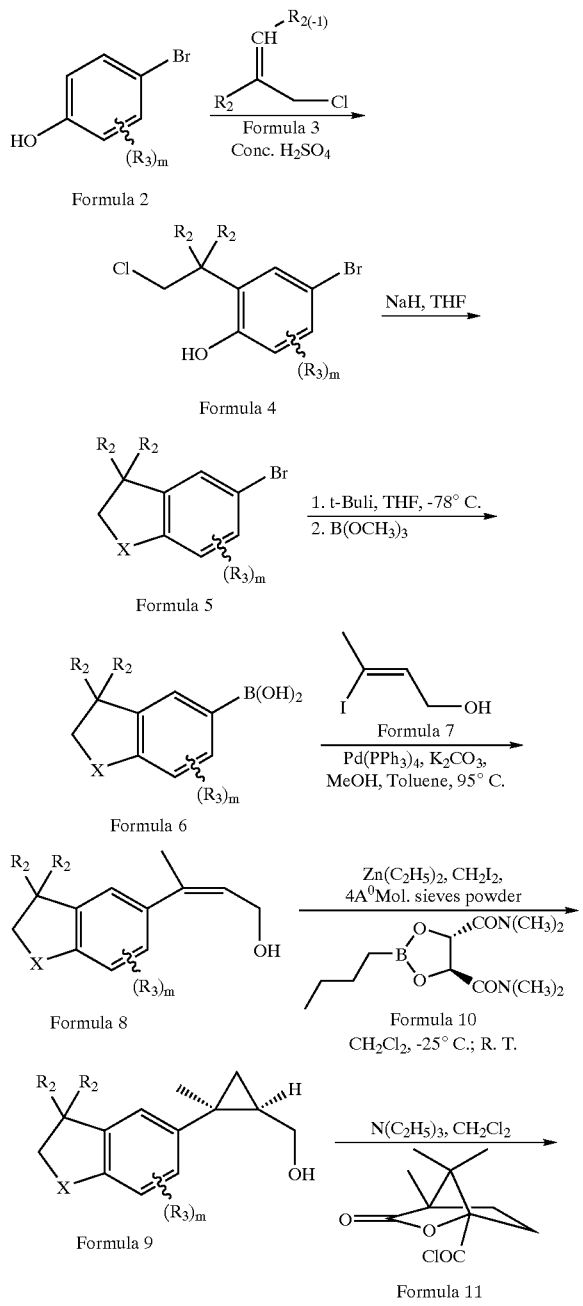

The compounds shown in Reaction Scheme 1 by Formulas 16 and 17 can be converted into further homologs and derivatives still within the scope of the invention, by such reactions as esterification, saponification, homologation, reduction to aldehyde or alcohol stage and the like, which per se are well known in the art. These reactions usually involve transformations of the group B in Formula 1, but are not necessarily limited to those. Some of the known and published general principles and synthetic methodology employed in the transformations of the B group are briefly described below.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and Protecting Groups, Ed. Greene, John Wiley & Sons, 1981.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Acetals or ketals can be prepared from the corresponding aldehyde or ketone by the method described in March, ibid, p 810.

Reaction Scheme 2 discloses a general and nevertheless presently preferred synthetic route to a class of preferred compounds of the invention where the variable Y of Formula 1 represents a bivalent 5 or 6 membered cycloalkyl radical, the variable X is O or S (dihydrobenzofuran and dihydrobenzothiophen derivatives) and where the 2,2' position of dihydrobenzofuran or of dihydrobenzothiophen is unsubstituted. Referring now to this scheme, one starting compound in this synthetic route is a compound of Formula 6, which can be obtained as described above in connection with Reaction Scheme. The other starting material is a bromo (or other halogeno) substituted cyclohexane or cyclopentane carboxylic acid ester of Formula 18 which may have additional $R_4$ substituents ($R_4$ is defined as in connection with Formula 1 and p in this and the ensuing schemes is defined as an integer having the values of 0 to 4). The bromo (or other halogeno) group and the carboxylic acid ester group are in adjacent (1,2) position in the compounds of Formula 18. Compounds of Formula 18 can be obtained in accordance with the chemical literature, for example by following the procedures described by Cook in J.Chem.Soc.; 1934; 946, 954 and by Ives in J.Chem.Soc.; 1943; 513, 516, or by such modifications of these chemical procedures which become readily apparent to those skilled in the art. The Cook and Ives publications are hereby expressly incorporated by reference.

The compounds of Formula 6 and of Formula 18 are reacted by heat in the presence of tetrakis (triphenylphosphine)palladium(0) ($Pd(PPh_3)_4$) and sodium carbonate in a mixture of methanol, toluene and water under an argon atmosphere to provide the dihydrobenzofuranyl or dihydrobenzothienyl-cycloalkylcarboxylic acid esters of Formula 19. The dihydrobenzofuranyl or dihydrobenzothienyl-cycloalkylcarboxylic acid esters of Formula 19 are then reduced to the corresponding aldehyde level by treatment with DIBAL-H (diisobutyl aluminum hydride) in the presence of tetra-n-propylammonium-perruthenate (TPAP) and N-methylmorpholine-N-oxide (NMO), providing the dihydrobenzofuranyl or dihydrobenzothienyl-cycloalkyl-aldehydes of Formula 20. The aldehyde of Formula 20 is thereafter coupled with the diethylphosphono reagent of Formula 15 in a Horner Emmons reaction to give the dihydrobenzofuranyl-cycloalkyl-pentadienoic acid ester derivatives or the corresponding dihydrothiophene derivatives of Formula 21. The compounds of Formula 21 are within the scope of the present invention and can be saponified to provide the free pentadienoic acid derivatives (or their salts) of Formula 22 or can be converted into further derivatives within the scope of the invention, as is described in connection with Reaction Scheme 1.

REACTION SCHEME 2

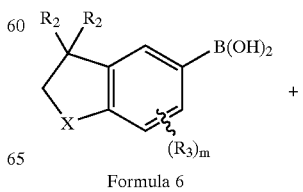

Formula 6

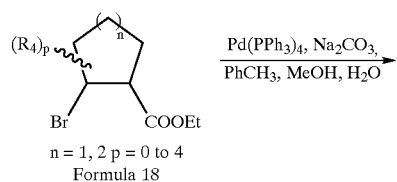

n = 1, 2 p = 0 to 4
Formula 18

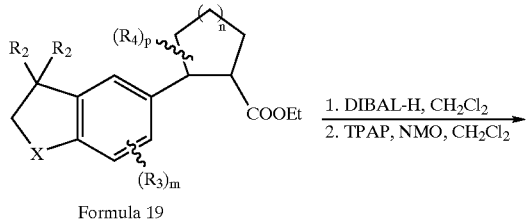

Formula 19

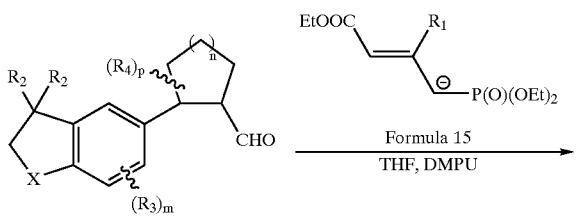

Formula 20

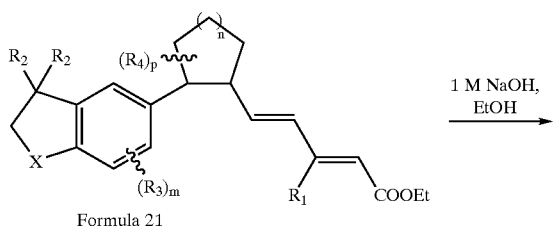

Formula 21

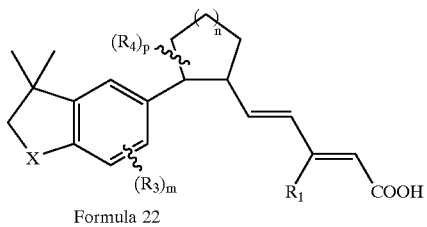

Formula 22

Reaction Scheme 3 discloses a general and nevertheless presently preferred synthetic route to a class of preferred compounds of the invention where the variable Y of Formula 1 represents a bivalent 5 or 6 membered cycloalkenyl radical having a single double bond in the ring and where the variable X is O or S (dihydrobenzofuran and dihydrobenzothiophen derivatives) and where the 2,2' position of dihydrobenzofuran or of dihydrobenzothiophen is unsubstituted. Referring now to this scheme, the starting compound in this synthetic route is a compound of Formula 23 which is a bromo (or other halogeno) substituted cyclohexene or cyclopentene carbaldehyde which may have additional $R_4$ substituents ($R_4$ is defined as in connection with Formula 1). The bromo (or other halogeno) group and the aldehyde group are in adjacent (1,2) position in the compounds of Formula 23. Compounds of Formula 23 can be obtained in accordance with the chemical literature, for example by following the procedures described by Arnold et al., Collect. Czech. Chem. Commun., 26, 1961, 3059–3073, or by such modifications of these chemical procedures which are readily apparent to those skilled in the art. The Arnold et al. publication is hereby expressly incorporated by reference.

The aldehyde of Formula 23 is reacted with the diethylphosphono reagent of Formula 15 in a Horner Emmons reaction to give a bromo substituted cycloalkenyl pentadioenoic acid ester of Formula 24. The compound of Formula 24 is then reacted with the 3,3-dialkyl-2,3-dihydrobenzofuran-5-boronic acid derivative (or corresponding dihydrobenzothienyl derivative) of Formula 6 in the presence of tetrakis(triphenylphosphine)-palladium(0) (Pd$(PPh_3)_4$) and sodium carbonate in a mixture of methanol, toluene and water under an argon atmosphere to provide the dihydrobenzofuranyl or dihydrobenzothienyl-cycloalkenyl-pentadienoic acid esters of Formula 25. The compounds of Formula 25 are within the scope of the present invention and can be saponified to provide the free pentadienoic acid derivatives (or their salts) of Formula 26 or can be converted into further derivatives within the scope of the invention, as is described in connection with Reaction Scheme 1.

REACTION SCHEME 3

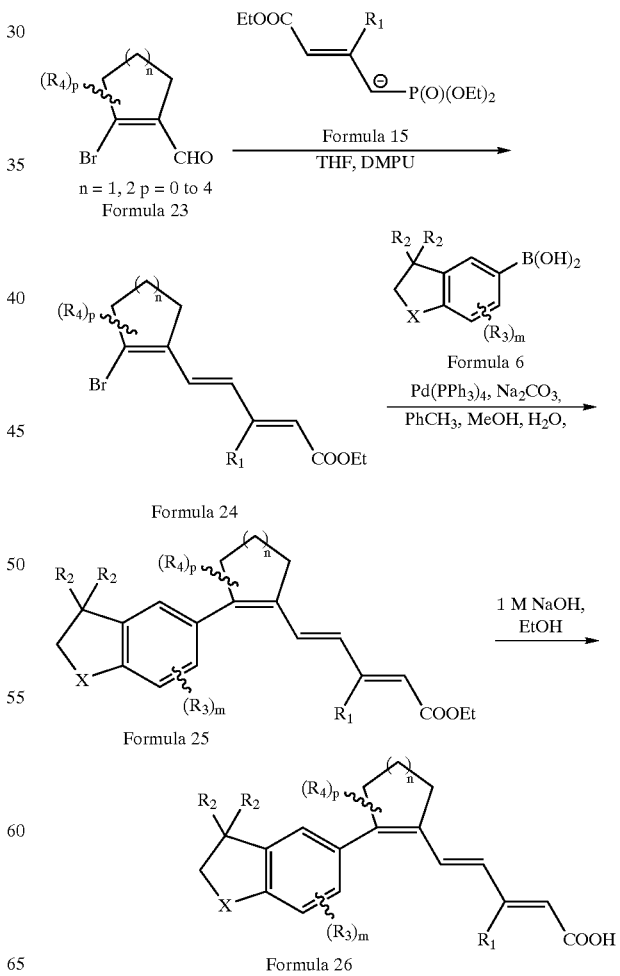

REACTION SCHEME 4

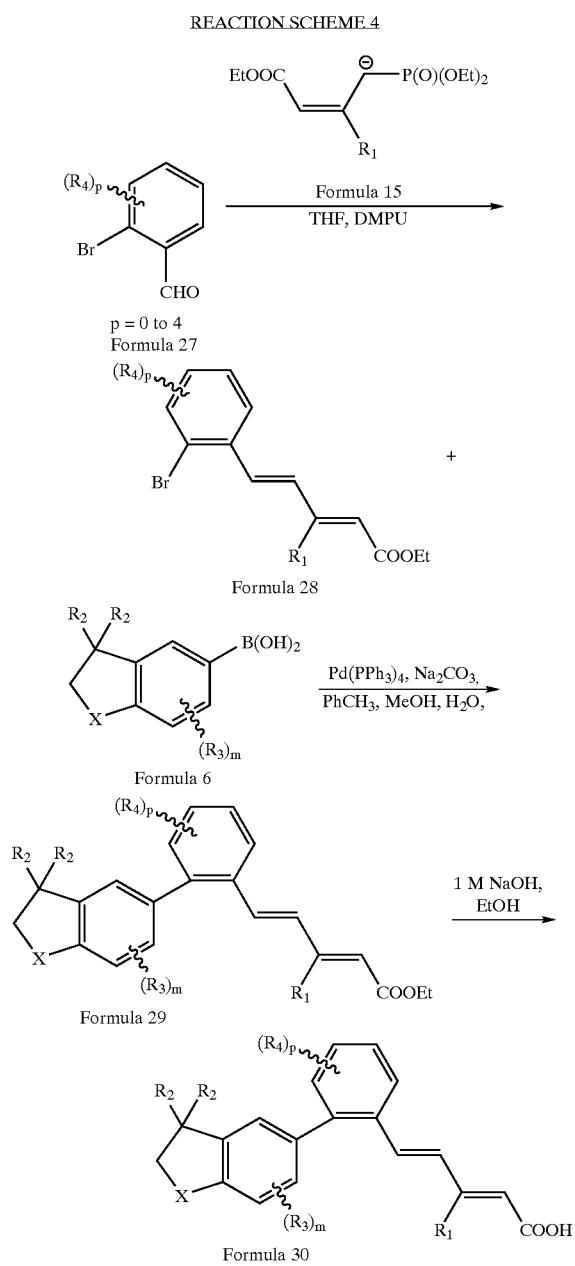

Reaction Scheme 4 discloses a general and nevertheless presently preferred synthetic route to a class of preferred compounds of the invention where the variable Y of Formula 1 represents a bivalent phenyl or a 5 or 6 heteroaryl radical and where the variable X is O or S (dihydrobenzofuran and dihydrobenzothiophen derivatives) and where the 2,2' position of dihydrobenzofuran or of dihydrobenzothiophen is unsubstituted. The aryl or heteroryl group is defined as in connection with Formula 1, although for the sake of simplifying the description in this scheme the formulas are drawn and the description is provided primarily with reference to the phenyl group only. Referring now to this scheme, the starting compound in this synthetic route is a compound of Formula 27 which is a bromo (or other halogeno) substituted aryl carbaldehyde (shown as benzaldehyde) which may have additional $R_4$ substituents ($R_4$ is defined as in connection with Formula 1). Such bromo (or other halogeno) substituted aryl carbaldehyde compounds can be obtained in accordance with the chemical patent and scientific literature or by such modifications of the literature procedures which are readily apparent to those skilled in the art. An example for a compound of Formula 27 is 2-bromobenzaldehyde which is available commercially Other examples for the reagent of Formula 27 are 3-bromopyridine-2-carboxaldehyde, 3-bromothiophene-2-carboxaldehyde, 3-bromofuran-2-carboxaldehyde, 2-bromopyridine-3-carboxaldehyde, 2-bromothiophene-3-carboxaldehyde and 2-bromofuran-3-carboxaldehyde.

The bromo-substituted aryl aldehyde of Formula 27 is reacted with the diethylphosphono reagent of Formula 15 in a Horner Emmons reaction to give a bromo substituted phenyl (or other aryl or heteroaryl) pentadioenoic acid ester of Formula 28. Reaction of the compound of Formula 28 with the 3,3-dialkyl-2,3-dihydro-benzofuran-5-boronic acid derivative (or corresponding dihydrobenzothienyl derivative) of Formula 6 in the presence of tetrakis (triphenylphosphine)palladium(0) ($Pd(PPh_3)_4$) and sodium carbonate in a mixture of methanol, toluene and water under an argon atmosphere provides the dihydrobenzofuranyl or dihydrobenzothienyl-phenyl (or heteroaryl) pentadienoic acid esters of Formula 29. The compounds of Formula 29 are within the scope of the present invention and can be saponified to provide the free pentadienoic acid derivatives (or their salts) of Formula 30 or can be converted into further derivatives within the scope of the invention, as is described in connection with Reaction Scheme 1.

Specific Embodiments

With reference to the symbol Y in Formula 1 the preferred compounds of the invention are those where Y is cyclopropyl. Compounds are also preferred where Y is a bivalent phenyl, naphthyl, pyridyl, thienyl or furyl radical, 5 or 6 membered cycloalkyl or 5 or 6 membered cycloalkenyl, substituted on adjacent carbons respectively with the pentadioenoic acid and the dihydrobenzofuranyl or dihydrobenzothienyl groups. In most of the presently preferred compounds of the invention the $R_4$ substituent on the cyclopropyl group is methyl, and there is only one methyl substituent on the cyclopropyl ring, however in some other preferred compounds the cyclopropyl group has no methyl substituent.

The compounds preferably are dihydrobenzofuran derivatives, so that the variable X is preferably oxygen (O).

The B group of the preferred compounds is COOH or $COOR_8$, where $R_8$ is defined as above. Even more preferably $R_8$ is alkyl of 1 to 6 carbons, most preferably ethyl, or the compound is a carboxylic acid, or a pharmaceutically acceptable salt thereof.

$R_1$ is preferably H or an alkyl group of 1 to 6 carbons. Even more preferably $R_1$ is H or methyl.

The $R_2$ groups are preferably H or alkyl of 1 to 6 carbons, more preferably alkyl. In the most preferred compounds of the invention both $R_2$ groups are methyl.

The $R'_2$ groups are also preferably H or alkyl of 1 to 6 carbons, most preferably H.

A great number of $R_3$ groups are preferred in the compounds of the invention, particularly when the $R_3$ group occupies the 7 position of the dihydrobenzofuran nucleus, as is shown in Table 1. Among the preferred $R_3$ groups are: H, halogen, particularly Br, alkyl of 1 to 10 carbons, cyclohexyl, hydroxyalkyl, and an alkyl group containing an oxo function, phenyl, phenyl substituted with halogen particularly with a fluoro group, phenyl substituted with one or two alkyl groups each having 1 to 10 carbons, phenyl substituted with an alkoxy group, or phenylmethyl. The presently most preferred compounds of the invention are shown as free carboxylic acids in Table 1, however it should be kept in mind that pharmaceutically acceptable salts and $C_{1-6}$ alkyl esters, particularly ethyl esters of these compounds are also preferred.

SPECIFIC EXAMPLES

4-Bromo-2-(2-chloro-1,1-dimethyl-ethyl)phenol (Intermediate 1)

To a stirred, cooled (ice bath) mixture of 4-bromophenol (0.512 g, 3 mmol) and 3-chloro-2-methylpropene (0.32 mL, 3.3 mmol), concentrated sulfuric acid (0.1 mL, 1.5 mmol) was added and the dark reaction mixture was stirred for 1 h. The reaction mixture was diluted with cold water and extracted with ether. The ethereal extract was washed with brine, dried over anhydrous sodium sulfate, filtered and evaporated to an oil. Flash column chromatography of the oil over silica gel (230–400 mesh) using 5% ethyl acetate in hexane as the eluent afforded the title compound as an oil (0.33 g, 42.6%). Some dialkylated product was also formed and some starting material was recovered.
$^1$H NMR (300 MHz, CDCl$_3$): δ 7.37 (d, 1H, J=2.4 Hz), 7.23 (dd, 1H, J=9.0, 2.2 Hz), 6.56 (dd, 1H, J=9.0, 1.0 Hz), 5.14 (s, 1H), 4.02 (s, 2H), 1.48 (s, 6H).

5-Bromo-3,3-dimethyl-2,3-dihydro-benzofuran (Intermediate 2)

To a stirred, cooled (ice bath) suspension of sodium hydride (60% dispersion in mineral oil, 0.024 g, 0.6 mmol) in 10 mL of anhydrous tetrahydrofuran under argon, a solution of 4-bromo-2-(2-chloro-1,1-dimethyl-ethyl)phenol (Intermediate 1, 0.13 g, 0.5 mmol) in 2 mL of anhydrous tetrahydrofuran was added. After 0.5 h, the excess sodium hydride was quenched with methanol and the reaction mixture was evaporated in vacuo. The residue was diluted with water, extracted with ether and the organic phase was washed with brine. The organic extract was dried over anhydrous sodium sulfate, filtered and evaporated to an oil. Flash column chromatography of the oil over silica gel (230–400 mesh) using 2.5% ethyl acetate in hexane as the eluent afforded the title compound as a pale yellow oil (0.085 g, 75.7%).
$^1$H NMR (300 MHz, CDCl$_3$): δ 7.20–7.24 (m, 2H), 6.68 (d, 1H, J=9.0 Hz), 4.24 (s, 2H), 1.34 (s, 6H).

General Procedure A: 3,3-Dimethyl-2,3-dihydro-benzofuran-5-boronic Acid (Intermediate 3)

A stirred, cooled (−78° C.) solution of 5-bromo-3,3-dimethyl-2,3-dihydro-benzofuran (Intermediate 2, 1.44 g, 6.2 mmol) in 18 mL of anhydrous ether and 5 mL of anhydrous tetrahydrofuran under argon, was treated with a 1.7M solution of t-butyllithium in n-pentane (7.65 mL, 13.02 mmol) and the resulting solution was stirred at the same temperature for 1 h. Trimethyl borate (1.6 mL, 13.02 mmol) was added and the reaction mixture was allowed warm from −78° C. to −30° C. over 2 h. The reaction was quenched with saturated aqueous ammonium chloride solution and extracted with ether. The combined organic extract was dried over anhydrous sodium sulfate, filtered and evaporated to a foamy solid. Flash column chromatography using 25–100% ethyl acetate in hexane as the eluent afforded 0.57 g, 47.8% of the title compound as a white solid.

General Procedure B: 3,3-Dimethyl-5-(3-hydroxy-1-methyl-prop-(1Z)-enyl-2,3-dihydro-benzofuran. (Intermediate 4)

A solution of 3,3-dimethyl-2,3-dihydro-benzofuran-5-boronic acid (Intermediate 3, 0.55 g, 2.86 mmol) and 3-iodo-but-2 (Z)-ene-ol (0.56 g, 2.86 mmol) in a mixture of methanol (4 mL), toluene (10 mL) and water (2 mL) was treated with sodium carbonate (0.6 g, 5.72 mmol) and tetrakis(triphenylphosphine)palladium(0)(85 mg), sparged with argon for 5 minutes and heated at 100° C. overnight. The reaction mixture was cooled to ambient temperature, the volatiles were distilled off in vacuo and the residue was diluted with water and extracted with ether. The combined organic extract was dried over anhydrous sodium sulfate and evaporated in vacuo to an oily residue which was purified by flash column chromatography over silica gel (230–400 mesh) using 22% ethyl acetate in hexane as the eluent to provide 0.57 g, 91% of the title compound as a brown oil.
$^1$H NMR (300 MHz, CDCl$_3$): δ 6.95–6.92 (m, 2H), 6.75 (d, 1H, J=7.1 Hz), 5.65 (dt, 1H, J=7.0, 1.3 Hz), 4.25 (s, 2H), 4.10 (d, 2H, J=7.0 Hz), 2.08 (s, 3H), 1.34 (s, 6H).

General Procedure C: 3,3-Dimethyl-5-F[(1S,2S)-3-hydroxy-1,2-methano-1-methyl-propyl]-2,3-dihydro-benzofuran (Intermediate 5)

To a stirred, cooled (-25° C.) solution of diethylzinc in anhydrous dichloromethane (30.5 mL of 1.1M solution, 33.6 mmol) under argon, 1,2-dimethoxyethane (3.5 mL, 33.6 mmol) was added over 2 minutes followed by diiodomethane (5.4 mL, 67.2 mmol) at such a rate that the temperature of the cooling bath did not increase above −20° C. After the addition was complete, the reaction mixture was stirred for 5 minutes and then cannulated into a cooled (-25° C.), stirred solution of 3,3-dimethyl-5-(3-hydroxy-1-methyl-prop-(1Z)-enyl)-2,3-dihydro-benzofuran (Intermediate 4, 0.57 g, 2.61 mmol), 4A$^0$ molecular sieves powder (1 g) and (4S-trans)-2-butyl-N,N,N',N'-tetramethyl[1,3,2] dioxaborolane-[4,5]dicarboxamide (2.0 g, 7 mmol) in 20 mL of anhydrous dichloromethane over 5 minutes. The slurry was stirred at −25° C. for 48 h and at ambient temperature for 2 h. The reaction was quenched with 20 mL of saturated, aqueous ammonium chloride solution and extracted with dichloromethane. The organic extract was dried over anhydrous sodium sulfate and evaporated to a residue which on purification by flash column chromatography on silica gel (230–400 mesh) using 28% ethyl acetate in hexane as the eluent provided 0.56 g, 92% of the title compound as a pale yellow, viscous oil.
$^1$H NMR (300 MHz, CDCl$_3$): δ 7.06 (dd, 1H, J=1.8, 8.6 Hz), 7.05 (d, 1H, J=1.8 Hz), 6.70 (d, 1H, J=8.6 Hz), 4.22 (s, 2H), 3.24 (d, 2H, J=7.2 Hz), 1.41 (m, 1H), 1.37 (s, 3H), 1.33 (s, 3H), 1.32 (s, 3H), 0.83 (t, 1H, J=5.0 Hz), 0.77 (dd, 1H, J=4.8, 8.4 Hz).

General Procedure D: (1S)-Camphanate Ester of 3,3-dimethyl-5-[(1S,2S)-3-hydroxy-1,2-methano-1-methyl-propyl]-2,3-dihydro-benzofuran (Intermediate 6)

A stirred, cooled (ice-bath) solution of 3,3-dimethyl-5-[(1S,2S)-3-hydroxy-1,2-methano-1-methyl-propyl]-2,3-dihydro-benzofuran (Intermediate 5, 0.56 g, 2.5 mmol) in anhydrous dichloromethane (12 mL) was treated with triethylamine (2.0 mL, 13.8 mmol) followed by (1S)-camphanic chloride (1.47 g, 6.8 mmol) under argon. The solution was allowed to warm to ambient temperature and stirred overnight. The reaction mixture was diluted with dichloromethane and washed with water. The organic phase was dried over anhydrous sodium sulfate and evaporated in vacuo to a viscous oil. Flash column chromatography on silica gel (230–400 mesh) using 10% ethyl acetate in hexane as the eluent provided the (1S)-camphanate ester (0.55 g, 53%, white solid, after preparative normal phase HPLC using 16% ethyl acetate in hexane as the mobile phase to eliminate the minor isomer formed during the cyclopropanation).
$^1$H NMR (300 MHz, CD$_3$COCD$_3$): δ 7.20 (d, 1H, J=1.8 Hz), 7.11 (dd, 1H, J=2.1, 8.2 Hz), 6.67 (d, 1H, J=8.1 Hz), 4.20 (s, 2H), 3.88 (dd, 1H, J=11.5, 7.4 Hz), 3.77 (dd, 1H, J=11.5, 7.8 Hz), 2.48–2.39 (m, 1H), 2.07–1.89 (m, 2H), 1.66–1.57 (m, 1H), 1.42–1.28 (m, 1H), 1.35 (s, 3H), 1.34 (s, 6H), 1.08 (s, 6H), 0.95 (s, 3H), 0.97–0.94 (m, 1H), 0.90–0.85 (m, 1H).

General Procedure E: 3,3-Dimethyl-5-[(1S,2S)-3-hydroxy-1,2-methano-1-methyl-propyl]-2,3-dihydro-benzofuran (Intermediate 5a)

A solution of the (1S)-camphanate ester of 3,3-dimethyl-5-[(1S,2S)-3-hydroxy-1,2-methano-1-methyl-propyl]-2,3-dihydro-benzofuran (Intermediate 6, 0.46 g, 1.04 mmol) in 10 mL of ethanol was treated with a 1M solution of sodium hydroxide and the resulting clear, homogenous solution was stirred at ambient temperature overnight. The volatiles were distilled off in vacuo and the residue was diluted with water and extracted with ether. The combined organic extract was washed with brine, dried over anhydrous sodium sulfate, filtered and evaporated to afford 0.27 g (100%) of 3,3-dimethyl-5-[(1S,2S)-3-hydroxy-1,2-methano-1-methyl-propyl]-2,3-dihydro-benzofuran as a colorless, viscous oil.

$^1$H NMR (300 MHz, CDCl$_3$): δ 7.06 (dd, 1H, J=1.8, 8.6 Hz), 7.05 (d, 1H, J=1.8 Hz), 6.70 (d, 1H, J=8.6 Hz), 4.22 (s, 2H), 3.24 (d, 2H, J=7.2 Hz), 1.41 (m, 11H), 1.37 (s, 3H), 1.33 (s, 3H), 1.32 (s, 3H), 0.83 (t, 1H, J=5.0 Hz), 0.77 (dd, 1H, J=4.8, 8.4 Hz).

General Procedure F: 3,3-Dimethyl-5-[(1S,2S)-1,2-methano-1-methyl-3-oxo-propyl]-2,3-dihydro-benzofuran (Intermediate 7)

A solution of 3,3-dimethyl-5-[(1S,2S)-3-hydroxy-1,2-methano-1-methyl-propyl]-2,3-dihydro-benzofuran (Intermediate 5a, 0.27 g, 1.04 mmol) in dichloromethane (12 mL) and acetonitrile (2 mL) was treated sequentially with 4A° molecular sieves powder (0.82 g), tetra-n-propylammoniumperruthenate (0.025 g) and N-methylmorpholine-N-oxide (0.31 g, 2.64 mmol) and the resulting slurry was stirred at ambient temperature for 0.75 h. The reaction mixture was diluted with 10 mL of hexane and subjected to flash column chromatography on silica gel using 10% ethyl acetate in hexane as the eluent to afford the title compound (0.22 g, 83%) as a colorless oil.

$^1$H NMR (300 MHz, CDCl$_3$): δ 8.42 (d, 1H, J=7.0 Hz), 7.07 (dd, 1H, J=1.9, 8.2 Hz), 7.04 (d, 1H, J=1.9 Hz), 6.70 (d, 1H, J=8.2 Hz), 4.22 (s, 2H), 1.93–1.83 (m, 2H), 1.44 (s, 3H), 1.40 (dd, 1H, J=5.0, 7.9 Hz), 1.32 (s, 3H), 1.30 (s, 3H).

General Procedure G: (6S,7S)-7-[5-(3,3-Dimethyl-2,3-dihydro-benzofuranyl)]-6,7-methano-3-methyl-octa-2E,4E-dienoic Acid Ethyl Ester (Compound 1)

A stirred, cooled (-78° C.) solution of methyl-3-methyl-4-diethylphosphonocrotonate (3.27 g, 12.4 mmol) in 22 mL of anhydrous tetrahydrofuran and 3 mL of 1,3-dimethyl-3,4,5,6-tetrahydro-2 (1H)-pyrimidinone (DMPU) was treated with 1.6 M solution of n-butyllithium in hexanes (7.74 mL, 12.4 mmol). After 10 minutes, a solution of 3,3-dimethyl-5-[(1S,2S)-1,2-methano-1-methyl-3-oxo-propyl]-2,3-dihydro-benzofuran (Intermediate 7, 0.22 g, 0.88 mmol) in tetrahydrofuran (3 mL) was cannulated into the reaction mixture and the reaction mixture was allowed to warm to −20° C. over 1 h. It was then quenched with saturated, aqueous solution of ammonium chloride and extracted with ether and the organic extract was dried over anhydrous sodium sulfate and evaporated in vacuo to a pale yellow oil. Flash column chromatography on silica gel (230–400 mesh) using 4% ethyl acetate in hexane as the eluent afforded an oil contaminated with 4% of the 2Z isomer. Preparative normal phase HPLC using 4% ethyl acetate in hexane as the mobile phase afforded the title compound (0.155 g, 48%).

$^1$H NMR (300 MHz, CDCl$_3$): δ 7.02 (dd, 1H, J=1.9, 8.2 Hz), 6.96 (d, 1H, J=1.9 Hz), 6.70 (d, 1H, J=1.9 Hz), 6.19 (d, 1H, J=15.5 Hz), 5.64 (s, 1H), 5.22 (dd, 1H, J=15.5, 10.0 Hz), 4.22 (s, 2H), 4.14 (q, 2H, J=7.1 Hz), 1.99 (s, 3H), 1.73–1.67 (m, 1H), 1.40 (s, 3H), 1.33 (s, 3H), 1.28 (s, 3H), 1.27 (t, 3H, J=7.1 Hz), 1.18 (dd, 1H, J=4.7, 8.2 Hz), 1.09 (t, 1H, J=4.9 Hz).

General Procedure H: (6S,7S)-7-[5-(3,3-Dimethyl-2,3-dihydro-benzofuranyl)]-6,7-methano-3-methyl-octa-2E,4E-dienoic Acid (Compound 2)

A solution of (6S,7S)-7-[5-(3,3-dimethyl-2,3-dihydro-benzofuranyl)]-6,7-methano-3-methyl-octa-2E,4E-dienoic acid ethyl ester (Compound 1, 0.15 g, 0.42 mmol) in ethanol was treated with 1M aqueous sodium hydroxide and the resulting clear, homogenous solution was heated at 55° C. overnight The reaction mixture was cooled to room temperature and the volatiles were distilled off in vacuo. The residue was diluted with water, neutralized with dilute hydrochloric acid and extracted with ether. The combined organic extract was dried over anhydrous sodium sulfate and evaporated in vacuo to an oily residue which was subjected to flash column chromatography and then purified by recrystallization from hexanes to afford the title compound (075 g, 50%) as a white solid.

$^1$H NMR (300 MHz, CDCl$_3$): δ 7.02 (dd, 1H, J=1.7, 8.2 Hz), 6.96 (d, 1H, J=1.7 Hz), 6.71 (d, 1H, J=8.1 Hz), 6.23 (d, 1H, J=15.5 Hz), 5.65 (s, 1H), 5.27 (dd, 1H, J=15.4, 10.0 Hz), 4.23 (s, 2H), 1.99 (s, 3H), 1.76–1.69 (m, 1H), 1.41 (s, 3H), 1.34 (s, 3H), 1.28 (s, 3H), 1.27–1.81 (m, 1H), 1.12 (t, 1H, J=4.8 Hz).

3,3,7-Trimethyl-2,3-dihydro-benzofuran-5-boronic Acid (Intermediate 8)

Following General Procedure A and using 5-bromo-3,3,7-trimethyl-2,3-dihydro-benzofuran (1.2 g, 5 mmol), 12 mL of anhydrous tetrahydrofuran, 1.7M solution of t-butyllithium in n-pentane (6.17 mL, 10.5 mmol) and trimethyl borate (1.2 mL, 10.5 mmol) the title compound was obtained as a foam that was used as such for the next step without purification and characterization. 5-Bromo-3,3,7-trimethyl-2,3-dihydro-benzofuran can be prepared as described in U.S. Pat. No. 6,093,838, incorporated herein by reference.

3,3,7-Trimethyl-5-(3-hydroxy-1-methyl-prop-(1Z)-enyl)-2.3-dihydro-benzofuran (Intermediate 9)

Following General Procedure B and using 3,3,7-trimethyl-2,3-dihydro-benzofuran-5-boronic acid (crude Intermediate 8, obtained from the previous step, ~5 mmol), 3-iodo-but-2 (Z)-ene-ol (0.6 g, 3 mmol), methanol (15 mL), toluene (30 mL), water (4 mL), sodium carbonate (1.05 g, 10 mmol) and tetrakis(triphenylphosphine)palladium(0)(80 mg), followed by flash column chromatography over silica gel (230–400 mesh) using 13% ethyl acetate in hexane as the eluent, the title compound was obtained (0.62 g, 53% over two steps).

$^1$H NMR (300 MHz, CDCl$_3$): δ 6.77 (s, 1H), 6.76 (s, 1H), 5.64 (dt, 1H, J=1.2, 6.6 Hz), 4.25 (s, 2H), 4.11 (d, 2H, J=7.0 Hz), 2.21 (s, 3H), 2.07 (s, 3H), 1.33 (s, 6H).

3,3,7-Trimethyl-5-[(1 S,2S)-3-hydroxy-1,2-methano-1-methyl-propyl]-2,3-dihydro-benzofuran (Intermediate 10)

Following General Procedure C and using diethylzinc in anhydrous dichloromethane (overall 29 mL of 1.1 SM solution, 33.3 mmol), 1,2-dimethoxyethane (3.46 mL, 33.3 mmol), diiodomethane (5.37 mL, 66.6 mmol), 3,3,7-trimethyl-5-(3-hydroxy-1-methyl-prop-(1Z)-enyl)-2,3-dihydro-benzofuran (Intermediate 9, 0.62 g, 2.8 mmol), 4A° molecular sieves powder (0.64 g) and (4S-trans)-2-butyl-N, N,N',N'-tetramethyl[1,3,2]dioxaborolane-[4,5] dicarboxamide (1.57 g, 5.83 mmol) in 15 mL of anhydrous dichloromethane followed by flash column chromatography on silica gel (230–400 mesh) using 15% ethyl acetate in hexane as the eluent, the title compound was obtained as a pale yellow viscous oil which was used as such for the next step (0.645 g, 94%).

(1S)-Camphanate ester of 337-trimethyl-5-[(1S,2 S)-3-hydroxy-1,2-methano-1-methyl-propyl]-2,3-dihydro-benzofuran (Intermediate 11)

Following General Procedure D and using 3,3,7-trimethyl-5-[(1S,2S)-3-hydroxy-1,2-methano-1-methyl-propyl]-2,3-dihydro-benzofuran (Intermediate 10, 0.64 g, 2.62 mmol), anhydrous dichloromethane (10 mL), triethylamine (2 mL, 13.9 mmol) and (1S)-camphanic chloride (1.5 g, 7.04 mmol) followed by flash column chromatography on silica gel (230–400 mesh) using 12% ethyl acetate in hexane as the eluent, the title compound was obtained (0.66 g, 59%, white solid after preparative normal phase HPLC using 10% ethyl acetate in hexane as the mobile phase to eliminate the minor isomer formed during the cyclopropanation).

$^1$H NMR (300 MHz, C$_6$D$_6$): δ 6.95 (d, 1H, J=1.7 Hz), 6.93 (d, 1H, J=1.7 Hz), 4.05 (dd, 1H, J=11.2, 7.0 Hz), 3.96 (s, 2H), 3.78 (dd, 1H, J=11.2, 7.2 Hz), 2.32 (s, 3H), 2.18–2.07 (m, 2H), 1.79–1.69 (m, 2H), 1.28–1.22 (m, 1H), 1.25 (s, 3H), 1.16 (s, 3H), 1.13 (s, 3H), 0.89 (s, 3H), 0.86 (s, 3H), 0.75–0.71 (m, 1H), 0.71 (s, 3H), 0.625–0.61 (m, 1H).

3,3,7-Trimethyl-5-[(1S,2S)-3-hydroxy-1,2-methano-1-methyl-propyl]-2,3-dihydro-benzofuran (Intermediate 10a)

Following General Procedure E and using the (1S)-Camphanate ester of 3,3,7-trimethyl-5-[(1S,2S)-3-hydroxy-1,2-methano-1-methyl-propyl]-2,3-dihydro-benzofuran (Intermediate 11, 0.66 g), 10 mL of ethanol and a SM solution of sodium hydroxide(3 mL), the title compound was obtained (0.47 g, 70% over 2 steps) as a colorless, viscous oil.

$^1$H NMR (300 MHz, CDCl$_3$): δ 6.90 (s, 1H), 6.88 (s, 1H), 4.22 (s, 2H), 3.28 (dd, 1H, J=11.2, 7.4 Hz), 3.22 (dd, 1H, J=11.2, 7.4 Hz), 2.18 (s, 3H), 1.37 (s, 3H), 1.314 (s, 3H), 1.309 (s, 3H), 1.29–1.22 (m, 1H), 0.88–0.82 (m, 1H), 0.717–0.723 (m, 1H). 3,3,7-Trimethyl-5-[(1S,2S)-12-methano-1-methyl-3-oxo-propyl]-2,3-dihydro-benzofuran (Intermediate 12)

Following General Procedure F and using 3,3,7-trimethyl-5-[(1S,2S)-3-hydroxy-1,2-methano-1-methyl-propyl]-2,3-dihydro-benzofuran (Intermediate 10a, 0.47 g, 1.93 mmol), dichloromethane (12 mL), acetonitrile (2 mL), 4A° molecular sieves powder (0.7 g), tetra-n-propylammoniumperruthenate (0.025 g) and N-methylmorpholine-N-oxide (0.57 g, 4.87 mmol) followed by flash column chromatography on silica gel (230–400 mesh) using 10% ethyl acetate in hexane as the eluent, the title compound was obtained (0.37 g, 79%) as a colorless oil.

$^1$H NMR (300 MHz, CDCl$_3$): δ 8.43 (d, 1H, J=7.0 Hz), 6.91 (s, 1H), 6.88 (s, 1H), 4.21 (s, 2H), 2.18 (s, 3H), 1.91–1.83 (m, 2H), 1.43 (s, 3H), 1.40–1.36 (m, 1H), 1.31 (s, 3H), 1.29 (s, 3H).

(6S,7S)-7-[5-(3,3,7-Trimethyl-2,3-dihydro-benzofuranyl)]-6,7-methano-3-methyl-octa-2E,4E-dienoic Acid Ethyl Ester (Compound 3)

Following General Procedure G and using methyl-3-methyl-4-diethylphosphonocrotonate (5.7 g, 21.6 mmol), 30 mL of anhydrous tetrahydrofuran, 4 mL of 1,3-dimethyl-3, 4,5,6-tetrahydro-2 (1H)-pyrimidinone (DMPU), 1.6M solution of n-butyllithium in hexanes (13.5 mL, 21.6 mmol), and 3,3,7-trimethyl-5-[(1S,2S)-1,2-methano-1-methyl-3-oxo-propyl]-2,3-dihydro-benzofuran (Intermediate 12, 0.37 g, 1.54 mmol) in tetrahydrofuran (3 mL), the title compound was obtained (0.29 g, 50%).

$^1$H NMR (300 MHz, CDCl$_3$): δ 6.86 (s, 1H), 6.78 (s, 1H), 6.18 (d, 1H, J=15.5 Hz), 5.63 (s, 1H), 5.24 (dd, 1H, J=15.5, 10.1 Hz), 4.22 (s, 2H), 4.14 (q, 2H, J=7.1 Hz), 2.19 (s, 3H), 2.00 (s, 3H), 1.73–1.65 (m, 1H), 1.39 (s, 3H), 1.32 (s, 3H), 1.26 (s, 3H), 1.26 (t, 3H, J=7.1 Hz) 1.18–1.14 (m, 1H), 1.10–1.06 (m,1H).

(6S,7S)-7-[5-(3,3,7-Trimethyl-2,3-dihydro-benzofuranyl)]-6,7-methano-3-methyl-octa-2E,4E-dienoic acid (Compound 4)

Following General Procedure H and using (6S,7S)-7-[5-(3,3,7-trimethyl-2,3-dihydro-benzofuranyl)]-6,7-methano-3-methyl-octa-2E,4E-dienoic acid ethyl ester (Compound 3, 0.24 g, 0.62 mmol), ethanol (15 mL) and 2M aqueous potassium hydroxide followed by flash column chromatography using 20% ethyl acetate in hexane as the eluent and recrystallization from hexanes, the title compound was obtained (0.085 g, 38%) as a white solid.

$^1$H NMR (300 MHz, CDCl$_3$): δ 6.86 (s, 1H), 6.78 (s, 1H), 6.22 (d, 1H, J=15.4 Hz), 5.65 (s, 1H), 5.30 (dd, 1H, J=15.4, 9.9 Hz), 4.22 (s, 2H), 2.19 (s, 3H), 2.00 (s, 3H), 1.74–1.66 (m, 1H), 1.39 (s, 3H), 1.32 (s, 3H), 1.26 (s, 3H), 1.20–1.16 (m, 1H), 1.12–1.10 (m, 1H).

General Procedure I: 7-Acetyl-5-bromo-3,3-dimethyl-2,3-dihydro-benzofuran (Intermediate 13)

A stirred, cooled (ice-bath) suspension of aluminum chloride (0.25 g, 1.7 mmol) in 3 mL of anhydrous dichloromethane was treated with acetyl chloride (0.2 mL, 2.6 mmol) under argon. A solution of 5-bromo-3,3-dimethyl-2, 3-dihydro-benzofuran (Intermediate 2, 0.22 g) in 1.5 mL of anhydrous dichloromethane was cannulated into the clear solution, and the resulting deep red solution was allowed to warm to ambient temperature over 1 h. The reaction mixture was poured onto iced water and extracted with dichloromethane. The combined organic extract was dried over anhydrous sodium sulfate, filtered and evaporated to a dirty white solid. Flash column chromatography on silica gel (230–400 mesh) using 6% ethyl acetate in hexane as the eluent afforded the title compound as a white solid (0.177 g, 67%).

$^1$H NMR (300 MHz, CDCl$_3$): δ 7.79 (d, 1H, J=2.2 Hz), 7.31 (d, 1H, J=2.2 Hz), 4.37 (S, 2H), 2.59 (s, 3H), 1.35 (s, 6H).

General Procedure J: 5-Bromo-3.3-dimethyl-7-ethyl-2.3-dihydro-benzofuran (Intermediate 14)

A solution of 7-acetyl-5-bromo-3,3-dimethyl-2,3-dihydro-benzofuran (Intermediate 13, 0.125 g, 0.5 mmol) in 3 mL of trifluoroacetic acid was treated with triethyl silane (0.9 mL, 11.3 mmol) and the resulting clear, colorless solution was heated at 55° C. for 2 h. The reaction mixture was cooled, treated with 6 mL each of methanol and water, neutralized cautiously with saturated sodium bicarbonate solution and extracted with hexanes. The organic extract was dried over anhydrous sodium sulfate, filtered and evaporated to an oil. Flash column chromatography using 2% ethyl acetate in hexane as the eluent afforded the title compound (0.11 g, 93%) as an oil.

$^1$H NMR (300 MHz, CDCl$_3$): δ 7.08 (d, 1H, J=2.2 Hz), 7.03 (d, 1H, J=2.2 Hz), 4.23 (s, 2H), 2.56 (q, 2H, J=7.5 Hz), 1.32 (s, 6H), 1.20 (t, 3H, J=7.5 Hz).

3,3-Dimethyl-7-ethyl-2,3-dihydro-benzofuran-5-boronic acid (Intermediate 15)

Following General Procedure A and using 5-bromo-3,3-dimethyl-7-ethyl-2,3-dihydro-benzofuran (Intermediate 14, 0.76 g, 3 mmol), 15 mL of anhydrous tetrahydrofuran, 1.7M solution of t-butyllithium in n-pentane (3.53 mL, 6 mmol) and trimethyl borate (0.75 mL, 7 mmol), the title compound was obtained as a foam that was used as such for the next step without purification and characterization.

3,3-Dimethyl-7-ethyl-5-(3-hydroxy-1-methyl-prop-(1Z)-enyl)-2,3-dihydro-benzofuran (Intermediate 16)

Following General Procedure B and using 3,3-dimethyl-7-ethyl-2,3-dihydro-benzofuran-5-boronic acid (crude Intermediate 15, obtained from the previous step, 3 mmol), 3-iodo-but-2 (Z)-ene-ol (0.53 g, 2.7 mmol), methanol (3 mL), toluene (20 mL), water (2 mL), potassium carbonate (0.83 g, 6 mmol) and tetrakis(triphenylphosphine)palladium (0)(80 mg), followed by flash column chromatography over silica gel (230–400 mesh) using 15% ethyl acetate in hexane as the eluent, the title compound was obtained (0.38 g, 52% over two steps).

$^1$H NMR (300 MHz, CDCl$_3$): δ 6.77 (d, 1H, J=1.8 Hz), 6.76 (d, 1H, J=1.8 Hz), 5.63 (dt, 1H, J=1.5, 6.9 Hz), 4.24 (s, 2H), 4.11 (d, 2H, J=5.1 Hz), 2.59 (q, 2H, J=7.5 Hz), 2.08 (s, 3H), 1.33 (s, 6H), 1.22 (t, 3H, J=7.5 Hz).

3,3-Dimethyl-7-ethyl-5-[(1S,2S)-3-hydroxy-1,2-methano-1-methyl-propyl]-2,3-dihydro-benzofuran (Intermediate 17)

Following General Procedure C and using diethylzinc in anhydrous dichloromethane (overall 18.8 mL of 0.99M solution, 18.7 mmol), 1,2-dimethoxyethane (1.94 mL, 18.7 mmol), diiodomethane (3 mL, 37 mmol), 3,3-dimethyl-7-ethyl-5-(3-hydroxy-1-methyl-prop-(1 Z)-enyl)-2,3-dihydro-benzofuran (Intermediate 16, 0.38 g, 1.55 mmol), 4A° molecular sieves powder (0.57 g) and (4S-trans)-2-butyl-N, N,',N',N-tetramethyl[1,3,2]dioxaborolane-[4,5] dicarboxamide (0.88 g, 3.3 mmol) in 8 mL of anhydrous dichloromethane followed by flash column chromatography on silica gel (230–400 mesh) using 13% ethyl acetate in hexane as the eluent, the title compound was obtained as a pale yellow viscous oil (0.323 g, 80%).

$^1$H NMR (300 MHz, CDCl$_3$): δ 6.92 (d, 1H, J=1.9 Hz), 6.88 (d, 1H, J=1.9 Hz), 4.21 (s, 2H), 3.24 (d, 2H, J=5.2 Hz), 2.58 (q, 2H, J=7.5 Hz), 1.37 (s, 3H), 1.31 (s, 6H), 1.30–1.22 (m, 1H), 1.21 (t, 3H, J=7.5 Hz), 0.85–0.82 (m, 1H), 0.77–0.73 (m, 1H).

(1S)-Camphanate Ester of 3,3-dimethyl-7-ethyl-5-[(1S,2S)-3-hydroxy-1,2-methano-1-methyl-propyl]-2,3-dihydro-benzofuran (Intermediate 18)

Following General Procedure D and using 3,3-dimethyl-7-ethyl-5-[(1S,2S)-3-hydroxy-1,2-methano-1-methyl-propyl]-2,3-dihydro-benzofuran (Intermediate 17, 0.32 g, 1.22 mmol), anhydrous dichloromethane (10 mL), triethylamine (0.7 mL, 4.9 mmol) and (1S)-camphanic chloride (0.52 g, 2.44 mmol) followed by flash column chromatography on silica gel (230–400 mesh) using 10% ethyl acetate in hexane as the eluent, the title compound was obtained (0.464 g, 86%, of white solid after preparative normal phase HPLC using 8% ethyl acetate in hexane as the mobile phase to eliminate the minor isomer formed during the cyclopropanation).

$^1$H NMR (300 MHz, C$_6$D$_6$): δ 6.89 (d, 1H, J=1.8 Hz), 6.87 (d, 1H, J=1.8 Hz), 4.21 (s, 2H), 3.91 (dd, 1H, J=11.4, 7.5 Hz), 3.81 (dd, 1H, J=11.4, 7.4 Hz), 2.57 (q, 2H, J=7.6 Hz), 2.45–2.36 (m, 1H), 2.05–1.85 (m, 2H), 1.72–1.62 (m, 1H), 1.35 (s, 3H), 1.32 (s, 3H), 1.31 (s, 3H), 1.27–1.17 (m, 1H), 1.21 (t, 3H, J=7.6 Hz), 1.12 (s, 3H), 1.04 (s, 3H), 0.98 (s, 3H), 0.90–0.80 (m, 2H).

3,3-Dimethyl-7-ethyl-5-[(1S,2S)-3-hydroxy-1,2-methano-1-methyl-propyl]-2,3-dihydro-benzofuran (Intermediate 17a)

Following General Procedure E and using the (1S)-Camphanate ester of 3,3-dimethyl-7-ethyl-5-[(1S,2S)-3-hydroxy-1,2-methano-1-methyl-propyl]-2,3-dihydro-benzofuran (Intermediate 18, 0.46 g, 1.04 mmol), 10 mL of ethanol and a 1M solution of sodium hydroxide, the title compound was obtained (0.27 g, 100%) as a colorless, viscous oil.

$^1$H NMR (300 MHz, CDCl$_3$): δ 6.92 (d, 1H, J=1.9 Hz), 6.88 (d, 1H, J=1.9 Hz), 4.21 (s, 2H), 3.24 (d, 2H, J=5.2 Hz), 2.58 (q, 2H, J=7.5 Hz), 1.37 (s, 3H), 1.31 (s, 6H), 1.30–1.22 (m, 1H), 1.21 (t, 3H, J=7.5 Hz), 0.85–0.82 (m, 1H), 0.77–0.73 (m, 1H).

3,3-Dimethyl-7-ethyl-5-[(1S,2S)-1,2-methano-1-methyl-3-oxo-propyl]-2,3-dihydro-benzofuran (Intermediate 19)

Following General Procedure F and using 3,3-dimethyl-7-ethyl-5-[(1S,2S)-3-hydroxy-1,2-methano-1-methyl-propyl]-2,3-dihydro-benzofuran (Intermediate 17a, 0.27 g, 1.04 mmol), dichloromethane (12 mL), acetonitrile (2 mL), 4A° molecular sieves powder (0.82 g), tetra-n-propylammoniumperruthenate (0.025 g) and N-methylmorpholine-N-oxide (0.31 g, 2.64 mmol) followed by flash column chromatography on silica gel (230–400 mesh) using 10% ethyl acetate in hexane as the eluent the title compound was obtained (0.22 g, 83%) as a colorless oil.

$^1$H NMR (300 MHz, CDCl$_3$): δ 8.41 (d, 1H, J=7.0 Hz), 6.93 (d, 1H, J=1.8 Hz), 6.88 (d, 1H, J=1.8 Hz), 4.22 (s, 2H), 2.57 (q, 2H, J=7.6 Hz), 1.90–1.80 (m, 2H), 1.44 (s, 3H), 1.43–1.33 (m, 1H), 1.32 (s, 3H), 1.30 (s, 3H), 1.21 (t, 3H, J=7.5 Hz).

(6S,7S)-7-[5-(3,3-Dimethyl-7-ethyl-2,3-dihydro-benzofuranyl)]-6,7-methano-3-methyl-octa-2E,4E-dienoic Acid Ethyl Ester (Compound 5)

Following General Procedure G and using methyl-3-methyl-4-diethylphosphonocrotonate (3.27 g, 12.4 mmol), 22 mL of anhydrous tetrahydrofuran, 3 mL of 1,3-dimethyl-3,4,5,6-tetrahydro-2 (1H)-pyrimidinone (DMPU), 1.6M solution of n-butyllithium in hexanes (7.74 mL, 12.4 mmol), and 3,3-dimethyl-7-ethyl-5-[(1S,2S)-1,2-methano-1-methyl-3-oxo-propyl]-2,3-dihydro-benzofuran (Intermediate 19, 0.22 g, 0.88 mmol) in tetrahydrofuran (3 mL), the title compound contaminated with 4% of the 2Z isomer was obtained. Preparative normal phase HPLC using 4% ethyl acetate in hexane as the mobile phase afforded the title compound (0.155 g, 48%).

$^1$H NMR (300 MHz, CDCl$_3$): δ 6.87 (d, 1H, J=1.8 Hz), 6.80 (d, 1H, J=1.8 Hz), 6.19 (d, 1H, J=15.5 Hz), 5.64 (s, 1H), 5.25 (dd, 1H, J=15.5, 10.0 Hz), 4.22 (s, 2H), 4.14 (q, 2H, J=7.1 Hz), 2.58 (m, 2H), 2.01 (s, 3H), 1.75–1.66 (m, 1H), 1.40 (s, 3H), 1.32 (s, 3H), 1.27 (s, 3H), 1.27 (t, 3H, J=7.1 Hz), 1.27 (s, 3H), 1.20 (t, 3H, J=5.7 Hz), 1.20–1.15 (m, 1H), 1.10–1.07 (m, 1H).

(6S,7S)-7-[5-(3,3-Dimethyl-7-ethyl-2,3-dihydro-benzofuranyl]-6,7-methano-3-methyl-octa-2E,4E-dienoic Acid (Compound 6)

Following General Procedure H and using (6S,7S)-7-[5-(3,3-dimethyl-7-ethyl-2,3-dihydro-benzofuranyl)]-6,7-methano-3-methyl-octa-2E,4E-dienoic acid ethyl ester (Compound 5, 0.15 g, 0.42 mmol), ethanol and 1M aqueous sodium hydroxide followed by flash column chromatography and recrystallization from hexanes, the title compound was obtained (0.075 g, 50%) as a white solid.

$^1$H NMR (300 MHz, CDCl$_3$): δ 6.87 (d, 1H, J=1.6 Hz), 6.79 (d, 1H, J=1.6 Hz), 6.22 (d, 1H, J=15.5 Hz), 5.65 (s, 1H), 5.31 (dd, 1H, J=15.5, 10.0 Hz), 4.22 (s, 2H), 2.68–2.48 (m, 2H), 2.00 (s, 3H), 1.75–1.66 (m, 1H), 1.40 (s, 3H), 1.32 (s, 3H), 1.27 (s, 3H), 1.20 (t, 3H, J=7.6 Hz), 1.27–1.17 (m, 1H), 1.12–1.10 (m, 1H).

3,3-Dimethyl-7-iso-propyl-2,3-dihydro-benzofuran-5-boronic acid (Intermediate 20)

Following General Procedure A and using 5-bromo-3,3-dimethyl-7-iso-propyl-2,3-dihydro-benzofuran (0.8 g, 3 mmol), 15 mL of anhydrous tetrahydrofuran, 1.7M solution of t-butyllithium in n-pentane (3.53 mL, 6 mmol) and trimethyl borate (0.75 mL, 6 mmol), the title compound was obtained as a foam that was used as such for the next step without purification and characterization. 5-Bromo-3,3-dimethyl-7-iso-propyl-2,3-dihydro-benzofuran can be prepared as described in U.S. Pat. No. 6,093,838.

3,3-Dimethyl-7-iso-propyl-5-(3-hydroxy-1-methyl-prop-(1 Z)-enyl)-2,3-dihydro-benzofuran (Intermediate 21)

Following General Procedure B and using 3,3-dimethyl-7-iso-propyl-2,3-dihydro-benzofuran-5-boronic acid (crude Intermediate 20, obtained from the previous step, 3 mmol), 3-iodo-but-2 (Z)-ene-ol (0.53 g, 2.7 mmol), methanol (3 mL), toluene (20 mL), water (2 mL), potassium carbonate (0.83 g, 6 mmol) and tetrakis(triphenylphosphine)palladium (0)(100 mg), followed by flash column chromatography over silica gel (230–400 mesh) using 13% ethyl acetate in hexane as the eluent the title compound was obtained (0.31 g, 40% over two steps).

$^1$H NMR (300 MHz, CDCl$_3$): δ 6.82 (d, 1H, J=1.8 Hz), 6.76 (d, 1H, J=1.8 Hz), 5.64 (dt, 1H, J=1.4, 6.9 Hz), 4.24 (s, 2H), 4.12 (dd, 2H, J=5.5, 5.6 Hz), 3.09 (heptet, 1H, J=6.9 Hz), 2.08 (s, 3H), 1.33 (s, 6H), 1.24 (d, 6H, J=6.9 Hz).

3,3-Dimethyl-7-iso-propyl-5-[(1S,2S)-3-hydroxy-1,2-methano-1-methyl-propyl]-2,3-dihydro-benzofuran (Intermediate 22)

Following General Procedure C and using diethylzinc in anhydrous dichloromethane (overall 14.65 mL of 0.99M solution, 14.5 mmol), 1,2-dimethoxyethane (1.51 mL, 14.5 mmol), diiodomethane (2.34 mL, 29 mmol), 3,3-dimethyl-7-iso-propyl-5-(3-hydroxy-1-methyl-prop-(1Z)-enyl)-2,3-dihydro-benzofuran (Intermediate 21, 0.31 g, 1.21 mmol), 4A° molecular sieves powder (0.47 g) and (4S-trans)-2-butyl-N,N,N',N'-tetramethyl[1,3,2]dioxaborolane-[4,5] dicarboxamide (0.69 g, 2.54 mmol) in 8 mL of anhydrous dichloromethane followed by flash column chromatography on silica gel (230–400 mesh) using 13% ethyl acetate in hexane as the eluent the title compound was obtained as a pale yellow viscous oil (0.3 g, 91%).

$^1$H NMR (300 MHz, CDCl$_3$): δ 6.96 (d, 1H, J=1.8 Hz), 6.88 (d, 1H, J=1.9 Hz), 4.21 (s, 2H), 3.28 (dd, 1H, J=6.5, 11.6 Hz), 3.20 (dd, 1H, J=7.7, 11.5 Hz), 3.06 (heptet, 1H, J=6.9 Hz), 1.38 (s, 3H), 1.32 (s, 3H), 1.31 (s, 3H), 1.29–1.22 (m, 1H), 1.23 (d, 6H, J=6.9 Hz), 0.85–0.82 (m, 1H), 0.78–0.77 (m, 1H).

(1S)-Camphanate ester of 3,3-dimethyl-7-iso-propyl-5-[(1S,2S)-3-hydroxy-1,2-methano-1-methyl-propyl]-2,3-dihydro-benzofuran (Intermediate 23)

Following General Procedure D and using 3,3-dimethyl-7-iso-propyl-5-[(1S,2S)-3-hydroxy-1,2-methano-1-methyl-propyl]-2,3-dihydro-benzofuran (Intermediate 22, 0.3 g, 1.1 mmol), anhydrous dichloromethane (10 mL), triethylamine (0.64 mL, 4.5 mmol) and (1S)-camphanic chloride (0.48 g, 2.21 mmol) followed by flash column chromatography on silica gel (230–400 mesh) using 10% ethyl acetate in hexane as the eluent the title compound was obtained (0.41 g, 81%, after preparative normal phase HPLC using 8% ethyl acetate in hexane as the mobile phase to eliminate the minor isomer formed during the cyclopropanation).

$^1$H NMR (300 MHz, CDCl$_3$): δ 6.85 (d, 1H, J=1.8 Hz), 6.80 (d, 1H, J=1.8 Hz), 4.14 (s, 2H), 3.88 (dd, 1H, J=11.4, 7.3 Hz), 3.71 (dd, 1H, J=11.4, 7.5 Hz), 3.0 (heptet, 1H, J=6.9 Hz), 2.39–2.28 (m, 1H), 1.95–1.80 (m, 2H), 1.65–1.58 (m, 1H), 1.29 (s, 3H), 1.26 (s, 3H), 1.24 (s, 3H), 1.27–1.17 (m, 1H),1.17 (d, 6H, J=6.9 Hz), 1.05 (s, 3H), 0.98 (s, 3H), 0.92 (s, 3H), 0.83–0.76 (m, 2H).

3,3-Dimethyl-7-iso-propyl-5-[(1S,2S)-3-hydroxy-1,2-methano-1-methyl-propyl]-2,3-dihydro-benzofuran (Intermediate 22a)

Following General Procedure E and using the (1S)-Camphanate ester of 3,3-dimethyl-7-iso-propyl-5-[(1S,2S)-3-hydroxy-1,2-methano-1-methyl-propyl]-2,3-dihydro-benzofuran (Intermediate 23, 0.35 g, 0.77 mmol), 10 mL of ethanol and a 1M solution of sodium hydroxide (4 mL), the title compound was obtained (0.209 g, 99%) as a colorless, viscous oil.

$^1$H NMR (300 MHz, CDCl$_3$): δ 6.96 (d, 1H, J=1.8 Hz), 6.88 (d, 1H, J=1.9 Hz), 4.21 (s, 2H), 3.28 (dd, 1H, J=6.5, 11.6 Hz), 3.20 (dd, 1H, J=7.7, 11.5 Hz), 3.06 (heptet, 1H, J=6.9 Hz), 1.38 (s, 3H), 1.32 (s, 3H), 1.31 (s, 3H), 1.29–1.22 (m, 1H), 1.23 (d, 6H, J=6.9 Hz), 0.85–0.82 (m, 1H), 0.78–0.77 (m, 1H).

3,3-Dimethyl-7-iso-propyl-5-[(1S,2S)-1,2-methano-1-methyl-3-oxo-propyl]-2,3-dihydro-benzofuran (Intermediate 24)

Following General Procedure F and using 3,3-dimethyl-7-iso-propyl-5-[(1S,2S)-3-hydroxy-1,2-methano-1-methyl-propyl]-2,3-dihydro-benzofuran (Intermediate 22a, 0.21 g, 0.8 mmol), dichloromethane (12 mL), acetonitrile (2 mL), 4A° molecular sieves powder (0.62 g), tetra-n-propylammoniumperruthenate (0.025 g) and N-methylmorpholine-N-oxide (0.23 g, 2 mmol) followed by flash column chromatography on silica gel (230–400 mesh) using 10% ethyl acetate in hexane as the eluent, the title compound was obtained (0.2 g, 96%) as a colorless oil.

$^1$H NMR (300 MHz, CDCl$_3$): δ 8.41 (d, 1H, J=7.0 Hz), 6.96 (d, 1H, J=1.8 Hz), 6.89 (d, 1H, J=1.8 Hz), 4.21 (s, 2H), 3.05 (heptet, 1H, J=6.9 Hz), 1.92–1.84 (m, 2H), 1.45 (s, 3H), 1.43–1.34 (m, 1H), 1.32 (s, 3H), 1.30 (s, 3H), 1.23 (d, 3H, J=6.9 Hz), 1.22 (d, 3H, J=6.9 Hz).

(6S,7S)-7-[5-(3,3-Dimethyl-7-iso-propyl-2,3-dihydro-benzofuranyl)]-6,7-methano-3-methyl-octa-2E,4E-dienoic Acid Ethyl Ester (Compound 7)

Following General Procedure G and using methyl-3-methyl-4-diethylphosphonocrotonate (2.84 g, 10.8 mmol), 25 mL of anhydrous tetrahydrofuran, 2.5 mL of 1,3-dimethyl-3,4,5,6-tetrahydro-2 (1H)-pyrimidinone (DMPU), 1.6M solution of n-butyllithium in hexanes (6.73 mL, 10.8 mmol), and 3,3-dimethyl-7-iso-propyl-5-[(1S,2S)-1,2-methano-1-methyl-3-oxo-propyl]-2,3-dihydro-benzofuran (Intermediate 24, 0.2 g, 0.77 mmol) in tetrahydrofuran (3 mL), the title compound contaminated with the 2Z isomer was obtained. Preparative normal phase HPLC using 3% ethyl acetate in hexane as the mobile phase afforded the title compound (0.133 g, 45% after HPLC).

$^1$H NMR (300 MHz, CDCl$_3$): δ 6.89 (d, 1H, J=1.7 Hz), 6.80 (d, 1H, J=1.8 Hz), 6.19 (d, 1H, J=15.5 Hz), 5.63 (s, 1H), 5.25 (dd, 1H, J=15.5, 10.1 Hz), 4.21 (s, 2H), 4.14 (q, 2H, J=7.1 Hz), 3.06 (heptet, 1H, J=7.0 Hz), 2.01 (s, 3H), 1.73–1.64 (m, 1H), 1.40 (s, 3H), 1.32 (s, 3H), 1.27 (s, 3H), 1.27 (t, 3H, J=7.5 Hz), 1.22 (d, 6H, J=7.2 Hz), 1.27–1.14 (m, 1H), 1.09–1.06 (m, 1H).

(6S,7S)-7-[5-(3,3-Dimethyl-7-iso-propyl-2,3-dihydro-benzofuranyl)]-6,7-methano-3-methyl-octa-2E,4E-dienoic Acid (Compound 8)

Following General Procedure H and using (6S,7S)-7-[5-(3,3-dimethyl-7-iso-propyl-2,3-dihydro-benzofuranyl)]-6,7-methano-3-methyl-octa-2E,4E-dienoic acid ethyl ester (Compound 7, 0.128 g, 0.33 mmol), ethanol (15 mL) and 5M aqueous potassium hydroxide (2 mL) followed by flash column chromatography using 15% ethyl acetate in hexane as the eluent, the title compound was obtained (0.097 g, 77%) as a white solid.

$^1$H NMR (300 MHz, CDCl$_3$): δ 6.88 (d, 1H, J=1.6 Hz), 6.80 (d, 1H, J=1.6 Hz), 6.21 (d, 1H, J=15.6 Hz), 5.65 (s, 1H), 5.31 (dd, 1H, J=15.6, 10.0 Hz), 4.21 (s, 2H), 3.06 (heptet, 1H, J=6.9 Hz), 2.00 (s, 3H), 1.75–1.66 (m, 1H), 1.40 (s, 3H), 1.32 (s, 3H), 1.27 (s, 3H), 1.21 (d, 6H, J=7.3 Hz), 1.27–1.17 (m, 1H), 1.11–1.08 (m, 1H).

3,3-Dimethyl-7-t-butyl-2,3-dihydro-benzofuran-5-boronic Acid (Intermediate 25)

Following General Procedure A and using 5-bromo-3,3-dimethyl-7-t-butyl-2,3-dihydro-benzofuran (1.42 g, 7 mmol), 15 mL of anhydrous tetrahydrofuran, 1.7M solution of t-butyllithium in n-pentane (8.25 mL, 14 mmol) and trimethyl borate (1.5 mL, 14 mmol), the title compound was obtained as a foam that was used as such for the next step without purification and characterization. 5-Bromo-3,3-dimethyl-7-t-butyl-2,3-dihydro-benzofuran can be prepared as described by Janusz et al. in J. Med. Chem. 1998, 41, 1124–1137.

3,3-Dimethyl-7-t-butyl-5-(3-hydroxy-1-methyl-prop-(1Z)-enyl)-2,3-dihydro-benzofuran (Intermediate 26)

Following General Procedure B and using 3,3-dimethyl-7-t-butyl-2,3-dihydro-benzofuran-5-boronic acid (Intermediate 25, 0.57 g, 2.3 mmol), 3-iodo-but-2 (Z)-ene-ol (0.4 g, 2 mmol), methanol (7.5 mL), toluene (15 mL), water (2 mL), sodium carbonate (0.5 g, 4.9 mmol) and tetrakis (triphenylphosphine)palladium(0)(60 mg), followed by flash column chromatography over silica gel (230–400 mesh) using 15% ethyl acetate in hexane as the eluent, the title compound was obtained (0.47 g, 57% over two steps).
$^1$H NMR (300 MHz, CDCl$_3$): δ 6.92 (d, 11H, J=1.9 Hz), 6.83 (d, 1H, J=1.9 Hz), 5.67 (dt, 1H, J=1.4, 6.6 Hz), 4.24 (s, 2H), 4.17 (d, 2H, J=6.6 Hz), 2.33 (br s, 1H), 2.12 (s, 3H), 1.40 (s, 9H), 1.36 (s, 6H).

3,3-Dimethyl-7-t-butyl-5-[(1S,2S)-3-hydroxyl-1,2-methano-1-methyl-propyl]-2,3-dihydro-benzofuran (Intermediate 27)

Following General Procedure C and using diethylzinc in anhydrous dichloromethane (overall 20.4 mL of 1M solution, 20.4 mmol), 1,2-dimethoxyethane (2.12 mL, 20.4 mmol), diiodomethane (3.28 mL, 41 mmol), 3,3-dimethyl-7-t-butyl-5-(3-hydroxy-1-methyl-prop-(1Z)-enyl)-2,3-dihydro-benzofuran (Intermediate 26, 0.47 g, 1.7 mmol), 4A° molecular sieves powder (0.7 g) and (4S-trans)-2-butyl-N,N,N',N'-tetramethyl[1,3,2]dioxaborolane-[4,5]dicarboxamide (0.97 g, 3.6 mmol) in 5 mL of anhydrous dichloromethane followed by flash column chromatography on silica gel (230–400 mesh) using 25% ethyl acetate in hexane as the eluent the title compound was obtained as a pale yellow viscous oil (0.44 g, 91%).
$^1$H NMR (300 MHz, CDCl$_3$): δ 7.00 (d, 1H, J=1.9 Hz), 6.89 (d, 1H, J=1.7 Hz), 4.19 (s, 2H), 3.24 (d, 2H, J=7.1 Hz), 1.37 (s, 3H), 1.34 (s, 9H), 1.30 (s, 3H), 1.30–1.20 (m, 1H), 1.30 (s, 3H), 0.88–0.73 (m, 2H).

1S)-Camphanate Ester of 33-dimethyl-7-t-butyl-5-[(1S,2S)-3-hydroxy-1,2-methano-1-methyl-propyl]-2,3-dihydro-benzofuran (Intermediate 28)

Following General Procedure D and using 3,3-dimethyl-7-t-butyl-5-[(1S,2S)-3-hydroxy-1,2-methano-1-methyl-propyl]-2,3-dihydro-benzofuran (Intermediate 27, 0.44 g, 1.54 mmol), anhydrous dichloromethane (10 mL), triethylamine (0.86 mL, 6.2 mmol) and (1S)-camphanic chloride (0.67 g, 3.1 mmol) followed by flash column chromatography on silica gel (230–400 mesh) using 20% ethyl acetate in hexane, as the eluent the title compound was obtained (0.47 g, 75% after recrystallization from hexane and pentane to eliminate the minor isomer formed during the cyclopropanation).
$^1$H NNMR (300 MHz, CDCl$_3$): δ 6.96 (d, 1H, J=1.7 Hz), 6.88 (d, 1H, J=1.7 Hz), 4.19 (s, 2H), 3.99 (dd, 1H, J=11.4, 7.1 Hz), 3.75 (dd, 1H, J=11.5, 7.7 Hz), 2.45–2.35 (m, 1H), 2.03–1.87 (m, 2H), 1.71–1.61 (m, 1H), 1.36 (s, 3H), 1.35–1.24 (m, 1H), 1.34 (s, 9H), 1.32 (s, 3H), 1.30 (s, 3H), 1.28 (s, 3H), 1.27 (s, 3H), 1.26 (s, 3H), 0.90–0.82 (m, 2H).

3,3-Dimethyl-7-t-butyl-5-[(1S,2S)-3-hydroxy-1,2-methano-1-methyl-propyl]-2,3-dihydro-benzofuran (Intermediate 27a)

Following General Procedure E and using the (1S)-camphanate ester of 3,3-dimethyl-7-t-butyl-5-[(1S,2S)-3-hydroxy-1,2-methano-1-methyl-propyl]-2,3-dihydro-benzofuran (Intermediate 28, 0.47 g, 1.16 mmol), 10 mL of ethanol, 5 mL of tetrahydrofuran and a 5M solution of sodium hydroxide (2 mL), the title compound was obtained (0.26 g, 59%) as a yellow oil after flash column chromatography using 15% ethyl acetate in hexane as the eluent.
$^1$H NMR (300 MHz, CDCl$_3$): δ 7.00 (d, 1H, J=1.9 Hz), 6.89 (d, 1H, J=1.7 Hz), 4.19 (s, 2H), 3.24 (d, 2H, J=7.1 Hz), 1.37 (s, 3H), 1.34 (s, 9H), 1.30 (s, 3H), 1.30–1.20 (m, 1H), 1.30 (s, 3H), 0.88–0.73 (m, 2H).

3,3-Dimethyl-7-t-butyl-5-[(1S,2S)-1,2-methano-1-methyl-3-oxo-propyl]-2,3-dihydro-benzofuran (Intermediate 29)

Following General Procedure F and using 3,3-dimethyl-7-t-butyl-5-[(1S,2S)-3-hydroxy-1,2-methano-1-methyl-propyl]-2,3-dihydro-benzofuran (Intermediate 27a, 0.26 g, 0.91 mmol), dichloromethane (15 mL), acetonitrile (2.5 mL), 4A° molecular sieves powder (0.4 g), tetra-n-propylammoniumperruthenate (0.03 g) and N-methylmorpholine-N-oxide (0.21 g, 1.82 mmol) followed by flash column chromatography on silica gel (230–400 mesh) using 10% ethyl acetate in hexane as the eluent, the title compound was obtained (0.26 g, 99%) as a colorless oil.
$^1$H NMR (300 MHz, CDCl$_3$): δ 8.40 (d, 1H, J=7.0 Hz), 7.01 (d, 1H, J=1.9 Hz), 6.90 (d, 1H, J=1.7 Hz), 4.20 (s, 2H), 1.92–1.82 (m, 2H), 1.45 (s, 3H), 1.44–1.35 (m, 1H), 1.34 (s, 9H), 1.31 (s, 3H), 1.39 (s, 3H).

(6S,7S)-7-[5-(3,3-Dimethyl-7-t-butyl-2,3-dihydro-benzofuranyl)]-6,7-methano-3-methyl-octa-2E,4E-dienoic Acid Ethyl Ester (Compound 9)

Following General Procedure G and using methyl-3-methyl-4-diethylphosphonocrotonate (3.11 g, 11.8 mmol), 15 mL of anhydrous tetrahydrofuran, 2 mL of 1,3-dimethyl-3,4,5,6-tetrahydro-2 (1H)-pyrimidinone (DMPU), 1.6M solution of n-butyllithium in hexanes (7.36 mL, 11.8 mmol), and 3,3-dimethyl-7-t-butyl-5-[(1S,2S)-1,2-methano-1-methyl-3-oxo-propyl]-2,3-dihydro-benzofuran (Intermediate 29, 0.26 g, 0.91 mmol) in tetrahydrofuran (3 mL), the title compound was obtained. Preparative reverse phase HPLC using 12% water in acetonitrile as the mobile phase afforded the title compound in good purity (0.347 g, 97% after HPLC).
$^1$H NMR (300 MHz, CDCl$_3$): δ 6.93 (d, 1H, J=1.7 Hz), 6.82 (d, 1H, J=1.8 Hz), 6.19 (d, 1H, J=15.5 Hz), 5.64 (s, 1H), 5.25 (dd, 1H, J=15.5, 10.0 Hz), 4.21 (s, 2H), 4.14 (q, 2H, J=7.1 Hz), 2.02 (s, 3H), 1.71–1.63 (m, 1H), 1.40 (s, 3H), 1.33 (s, 9H), 1.31 (s, 3H), 1.27 (s, 3H), 1.27 (t, 3H, J=7.1 Hz) 1.29–1.15 (m, 1H), 1.08–1.05 (m, 1H).

(6S,7S)-7-[5-(3,3-Dimethyl-7-t-butyl-2,3-dihydro-benzofuranyl)]-6,7-methano-3-methyl-octa-2E,4E-dienoic acid (Compound 10)

Following General Procedure H and using (6S,7S)-7-[5-(3,3-dimethyl-7-t-butyl-2,3-dihydro-benzofuranyl)]-6,7-methano-3-methyl-octa-2E,4E-dienoic acid ethyl ester (Compound 9, 0.306 g, 0.77 mmol), ethanol (20 mL) and 1M aqueous sodium hydroxide (2 mL) followed by flash column chromatography using 20% ethyl acetate in hexane as the eluent, the title compound was obtained (0.163 g, 57%) as a white solid.
$^1$H NMR (300 MHz, CDCl$_3$): δ 6.93 (s, 11H), 6.82 (s, 1H), 6.22 (d, 1H, J=15.4 Hz), 5.65 (s, 1H), 5.31 (dd, 1H, J=15.4, 10.1 Hz), 4.20 (s, 2H), 2.01 (s, 3H), 1.73–1.65 (m, 1H), 1.40 (s, 3H), 1.32 (s, 9H), 1.31 (s, 3H), 1.26 (s, 3H), 1.29–1.19 (m, 1H), 1.17–1.07 (m, 1H).

5-Bromo-3,3-dimethyl-2,3-dihydrobenzofuran-7-carbaldehyde (Intermediate 30)

To a stirred, cooled (ice-bath) solution of 5-bromo-3,3-dimethyl-2,3-dihydrobenzofuran (Intermediate 2, 0.4 g, 1.57 mmol) in anhydrous dichloromethane(4 mL), titanium tetrachloride (0.172 mL, 1.57 mmol) was added followed by dichloromethyl ether (0.14 mL, 1.57 mmol). The reaction mixture was allowed to warm to room temperature and at the end of 3 hr, the reaction mixture was poured into iced water and extracted with diethyl ether. The organic phase was washed with brine, dried over anhydrous sodium sulfate, filtered and evaporated to a residue that on flash column chromatography using 2.5% ethyl acetate in hexane as the eluent afforded the title compound (0.25 g, 63%).

$^1$H NMR (300 MHz, CDCl$_3$): δ 10.13 (s, 1H), 7.71 (d, 1H, J=2.0 Hz), 7.38 (d, 1H, J=2.1 Hz), 4.42 (s, 2H), 1.38 (s, 6H).

General Procedure K: 1-(5-Bromo-3,3-dimethyl-2,3-dihydro-benzofuran-7-yl)-2,2-dimethyl-propan-1-ol (Intermediate 31)

A stirred, cooled (ice-bath) solution of 5-bromo-3,3-dimethyl-2,3-dihydrobenzofuran-7-carbaldehyde (Intermediate 30, 1.72 g, 6.74 mmol) in 15 mL of anhydrous tetrahydrofuran was treated with a 1M solution of tert-butyl magnesium chloride solution in ether (6.74 mL, 6.74 mmol). The reaction mixture was then allowed to warm to room temperature and stirred overnight. The reaction mixture was diluted with ethyl acetate and washed with brine. The organic phase was dried over anhydrous sodium sulfate, filtered and evaporated to an oil that on flash column chromatography using 5% ethyl acetate in hexane as the eluent afforded the title compound (0.95 g, 45%).

$^1$H NMR (300 MHz, CDCl$_3$): δ 7.21 (d, 11H, J=2.0 Hz), 7.09 (d, 1H, J=2.0 Hz), 4.47 (d, 1H, J=5.7 Hz), 4.21 (d, 1H, J=8.3 Hz), 4.17 (d, 1H, J=8.7 Hz), 2.66 (d, 1H, J=5.7 Hz), 1.31 (s, 6H), 0.92 (s, 9H).

5-Bromo-3,3-dimethyl-7-(2,2-dimethyl-propyl)-2,3-dihydrobenzofuran (Intermediate 32)

Following General Procedure J and using 1-(5-bromo-3,3-dimethyl-2,3-dihydro-benzofuran-7-yl)-2,2-dimethyl-propan-1-ol. (Intermediate 31, 0.951 g, 3.05 mmol), anhydrous dichloromethane (7 mL), triethyl silane (4 mL, 12.2 mmol) and trifluoroacetic acid (2 mL, 12.2 mmol) followed by flash column chromatography using 1% ethyl acetate in hexane as the eluent, the title compound was obtained (0.7 g, 78%).

$^1$HNMR (300 MHz, CDCl$_3$): δ 7.04 (d, 1H, J=2.1 Hz), 7.00 (d, 1H, J=2.1 Hz), 4.14 (s, 2H), 2.42 (s, 2H). 1.29 (s, 6H), 0.91 (s, 9H).

3,3-Dimethyl-7-(2,2-dimethyl-propyl)-2,3-dihydro-benzofuran-5-boronic Acid (Intermediate 33)

Following General Procedure A and using 5-bromo-3,3-dimethyl-7-(2,2-dimethyl-propyl)-2,3-dihydro-benzofuran (Intermediate 32, 0.7 g, 2.37 mmol), 15 mL of anhydrous tetrahydrofuran, 1.7M solution of t-butyllithium in n-pentane (3.53 mL, 6 mmol) and trimethyl borate (0.75 mL, 6 mmol) the title compound was obtained as a foam that was used as such for the next step without purification and characterization.

3,3-Dimethyl-7-(2,2-dimethyl-propyl)-5-(3-hydroxy-1-methyl-prop-(1 Z)-enyl)-2,3-dihydro-benzofuran (Intermediate 34)

Following General Procedure B and using 3,3-dimethyl-7-(2,2-dimethyl-propyl)-2,3-dihydro-benzofuran-5-boronic acid (Intermediate 33, crude, obtained from the previous step, 2.37 mmol), 3-iodo-but-2 (Z)-ene-ol (0.47 g, 2.37 mmol), methanol (5 mL), toluene (15 mL), water (1.5 mL), potassium carbonate (0.65 g, 4.75 mmol) and tetrakis (triphenylphosphine)palladium(0)(50 mg), followed by flash column chromatography over silica gel (230–400 mesh) using 15% ethyl acetate in hexane as the eluent the title compound was obtained (0.38 g, 56% over two steps).

$^1$H NMR (300 MHz, CDCl$_3$): δ 6.79 (d, 1H, J=1.8 Hz), 6.71 (d, 1H, J-1.8 Hz), 5.63 (dt, 1H, J=1.4, 6.8 Hz), 4.18 (s, 2H), 4.13 (d, 2H, J=6.6 Hz), 2.48 (s, 2H), 2.08 (s, 3H), 1.32 (s, 6H), 0.94 (s, 9H).

3,3-Dimethyl-7-(2,2-dimethyl-propyl)-5-[(1S,2S)-3-hydroxy-1.2-methano-1-methyl-propyl]-2,3-dihydro-benzofuran (Intermediate 35)

Following General Procedure C and using 1M diethylzinc in anhydrous dichloromethane (16 mL, 16 mmol), 1,2-dimethoxyethane (1.66 mL, 16 mmol), diiodomethane (2.58 mL, 32 mmol), 3,3-dimethyl-7-(2,2-dimethyl-propyl)-5-(3-hydroxy-1-methyl-prop-(1Z)-enyl)-2,3-dihydro-benzofuran (Intermediate 34, 0.38 g, 1.33 mmol), 4A° molecular sieves powder (0.57 g) and (4S-trans)-2-butyl-N,N,N',N'-tetramethyl[1,3,2]dioxaborolane-[4,5]dicarboxamide (0.76 g, 2.8 mmol) in 3 mL of anhydrous dichloromethane followed by flash column chromatography the title compound was obtained as a pale yellow viscous oil (0.39 g, 100%).

$^1$H NMR (300 MHz, CDCl$_3$): δ 6.88 (δ, 1H, Θ=1.9Hζ), 6.82 (δ, 1H, Θ=1.9Hζ), 4.14 (σ, 2H), 3.32–3.18 (μ, 2H), 2.47 (σ, 2H), 1.37 (σ, 3H), 1.30 (σ, 6H), 1.25–1.18 (μ, 1H), 0.90 (σ, 9H), 0.71–0.85 (μ, 2H).

(1S)-Camphanate ester of 3,3-dimethyl-7-(2,2-dimethyl-propyl)-5-[(1S,2S)-3-hydroxy-1,2-methano-1-methyl-propyl]-2,3-dihydro-benzofuran (Intermediate 36)

Following General Procedure D and using 3,3-dimethyl-7-(2,2-dimethyl-propyl)-5-[(1S,2S)-3-hydroxy-1,2-methano-1-methyl-propyl]-2,3-dihydro-benzofuran (Intermediate 35, 0.39 g, 1.33 mmol),anhydrous dichloromethane (5 mL), triethylamine (0.74 mL, 5.33 mmol) and (1S)-camphanic chloride (0.58 g, 2.66 mmol) followed by flash column chromatography on silica gel (230–400 mesh) using 10% ethyl acetate in hexane as the eluent the title compound was obtained (white solid, after preparative normal phase HPLC to eliminate the minor isomer formed during the cyclopropanation).

$^1$H NMP (300 MHζ, X$_6$Δ$_6$): δ 7.00 (d, 1H, J=1.9 Hz), 6.95 (d, 1H, J=1.9 Hz), 4.05 (dd, 1H, J=11.3, 7.0 Hz), 3.91 (s, 2H), 3.81 (dd, 1H, J=11.3, 7.9 Hz), 2.69 (s, 2H), 2.16–2.07 (m, 2H), 1.76–1.66 (m, 2H), 1.30–1.22 (m, 1H), 1.24 (s, 3H), 1.16 (s, 3H), 1.13 (s, 3H), 1.06 (s, 9H), 0.89 (s, 3H), 0.85 (s, 3H), 0.80–0.77 (m, 1H), 0.71 (s, 3H), 0.65–0.61 (m, 1H).

3,3-Dimethyl-7-(2,2-dimethyl-propyl)-5-[(1S,2S)-3-hydroxy-1,2-methano-1-methyl-propyl]-2,3-dihydro-benzofuran (Intermediate 35a)

Following General Procedure E and the using the (1S)-camphanate ester of 3,3-dimethyl-7-(2,2-dimethyl-propyl)-5-[(1S,2S)-3-hydroxy-1,2-methano-1-methyl-propyl]-2,3-dihydro-benzofuran (as obtained from previous step, Intermediate 36, 1.33 mmol), 10 mL of ethanol, a SM solution of sodium hydroxide(3 mL), the title compound was obtained (0.28 g, 73% for 2 steps) as a pale yellow oil.

$^1$H NMR (300 MHz, CDCl$_3$): δ 6.88 (d, 1H, J=1.9 Hz), 6.82 (d, 1H, J=1.9 Hz), 4.14 (s, 2H), 3.32–3.18 (m, 2H), 2.47 (s, 2H), 1.37 (s, 3H), 1.30 (s, 6H), 1.25–1.18 (m, 1H), 0.90 (s, 9H), 0.71–0.85 (m, 2H).

3,3-Dimethyl-7-(2,2-dimethyl-propyl)-5-[(1S,2S)-1,2-methano-1-methyl-3-oxo-propyl]-2,3-dihydro-benzofuran (Intermediate 37)

Following General Procedure F and using 3,3-dimethyl-7-(2,2-dimethyl-propyl)-5-[(1S,2S)-3-hydroxy-1,2-methano-1-methyl-propyl]-2,3-dihydro-benzofuran (Intermediate 35a, 0.28 g, 0.92 mmol), dichloromethane (12 mL), acetonitrile (2 mL), 4A° molecular sieves powder (0.4 g), tetra-n-propylammoniumperruthenate (0.03 g) and N-methylmorpholine-N-oxide (0.22 g, 1.85 mmol) followed by flash column chromatography on silica gel (230–400 mesh) using 10% ethyl acetate in hexane as the eluent the title compound was obtained (0.24 g, 87%) as a colorless oil.
$^1$H NMR (300 MHz, CCl$_3$): δ 8.41 (d, 1H, J=7.0 Hz), 6.90 (d, 1H, J=1.8 Hz), 6.84 (d, 1H, J=1.8 Hz), 4.15 (s, 2H), 2.45 (s, 2H), 1.91–1.80 (m, 2H), 1.44 (s, 3H), 1.40–1.21 (m, 1H), 1.31 (s, 3H), 1.29 (s, 3H), 0.90 (s, 9H).

5-{(1S,2S)-2-[7-(2,2-Dimethyl-propyl)-3,3-dimethyl-2,3-dihydro-benzofuran-5-yl]-2-methyl-cyclopropyl}-3-methyl-penta-2E,4E-dienoic Acid Ethyl Ester (Compound 11)

Following General Procedure G and using methyl-3-methyl-4-diethylphosphonocrotonate (2.44 g, 9.22 mmol), 15 mL of anhydrous tetrahydrofuran, 2 mL of 1,3-dimethyl-3,4,5,6-tetrahydro-2 (1H)-pyrimidinone (DMPU), 1.6M solution of n-butyllithium in hexanes (5.77 mL, 9.2 mmol), and 3,3-dimethyl-7-(2,2-dimethyl-propyl)-5-[(1S,2S)-1,2-methano-1-methyl-3-oxo-propyl]-2,3-dihydro-benzofuran (Intermediate 37, 0.24 g, 0.8 mmol) in tetrahydrofuran (3 mL) the title compound contaminated with the 4Z isomer was obtained. Preparative normal phase HPLC using 1.5% ethyl acetate in hexane as the mobile phase afforded the title compound (0.177 g, 54%).
$^1$H NMR (300 MHz, CDCl$_3$): δ 6.81 (d, 1H, J=1.8 Hz), 6.78 (d, 1H, J=1.8 Hz), 6.16 (d, 1H, J=15.6 Hz), 5.61 (s, 1H), 5.25 (dd, 1H, J=15.5, 9.9 Hz), 4.15 (s, 2H), 4.13 (q, 2H, J=7.1 Hz), 2.49 (d, 1H, J=12.8 Hz), 2.40 (d, 1H, J=12.9 Hz), 1.98 (s, 3H), 1.75–1.65 (m, 1H), 1.40 (s, 3H), 1.31 (s, 3H), 1.26 (s, 3H), 1.26 (t, 3H, J=7.1 Hz), 1.19–1.08 (m, 2H), 0.89 (s, 9H).

5-{(1S,2S) 2-[7-(2,2-Dimethyl-propyl)-3,3-dimethyl-2,3-dihydro-benzofuran-5-yl]-2-methyl-cyclopropyl}-3-methyl-penta-2E,4E-dienoic Acid (Compound 12)

Following General Procedure H and using 5-{(1S, 2S) 2-[7-(2,2-dimethyl-propyl)-3,3-dimethyl-2,3-dihydro-benzofuran-5-yl]-2-methyl-cyclopropyl}-3-methyl-penta-2E,4E-dienoic acid ethyl ester (Compound 11, 0.132 g, 0.32 mmol), 15 mL of methanol and 5M aqueous sodium hydroxide (2 mL) followed by flash column chromatography using 25% ethyl acetate in hexane as the eluent and preparative reverse phase HPLC using 12% water in acetonitrile as the mobile phase, the title compound was obtained (0.098 g, 75%) as a white solid.
$^1$H NMR (300 MHz, CDCl$_3$): δ 10.68 (br, 1H), 6.81 (d, 1H, J=1.5 Hz), 6.78 (d, 1H, J=1.5 Hz), 6.19 (d, 1H, J=15.4 Hz), 5.62 (s, 1H), 5.27 (dd, 1H, J=15.5, 9.9 Hz), 4.15 (s, 2H), 2.49 (d, 1H, J=12.8 Hz), 2.39 (d, 1H, J=12.8 Hz), 1.97 (s, 3H), 1.75–1.65 (m, 1H), 1.40 (s, 3H), 1.31 (s, 3H), 1.26 (s, 3H), 1.18–1.08 (m, 2H) 0.88 (s, 9H).

7-Benzoyl-5-bromo-3,3-dimethyl-2,3-dihydro-benzofuran (Intermediate 38)

Following General Procedure I and using aluminum chloride (1.76 g, 13.2 mmol), 20 mL of anhydrous dichloromethane, 5-bromo-3,3-dimethyl-2,3-dihydro-benzofuran (Intermediate 2, 1.5 g, 6.61 mmol) and benzoyl chloride (1.53 mL, 13.2 mmol) followed by flash column chromatography on silica gel (230–1400 mesh) using 7% ethyl acetate in hexane as the eluent, the title compound was obtained (2.15 g, 99%).
$^1$H NMR (300 MHz, CDCl$_3$): δ 7.81 (d, 2H, J=6.7 Hz), 7.49 (d, 11H, J=2.1 Hz), 7.48–7.42 (m, 3H), 7.35 (d, 1H, J=2.1 Hz), 4.26 (s, 2H), 1.36 (s, 6H).

7-Benzyl-5-bromo-3,3-dimethyl-2,3-dihydro-benzofuran (Intermediate 39)

Following General Procedure J and using 7-benzoyl-5-bromo-3,3-dimethyl-2,3-dihydrobenzofuran (Intermediate 38, 2.15 g, 6.53 mmol), anhydrous dichloromethane (10 mL), trifluoroacetic acid (4.12 mL, 53.5 mmol) and triethyl silane (8.4 mL, 52 mmol) followed by flash column chromatography, the title compound was obtained (1.57 g, 76%). $^1$H NMR (300 MHz, CDCl$_3$): δ 7.23–7.14 (m, 5H), 7.02 (d, 1H, J=1.9 Hz), 6.97 (d, 1H, J=1.9 Hz), 4.17 (s, 2H), 3.85 (s, 2H), 1.36 (s, 6H).

7-Benzyl-3,3-dimethyl-2,3-dihydro-benzofuran-5-boronic Acid (Intermediate 40)

Following General Procedure A and using 7-benzyl-5-bromo-3,3-dimethyl-2,3-dihydro-benzofuran (Intermediate 39, 1.57 g, 4.81 mmol), 15 mL of anhydrous tetrahydrofuran, 1.7M solution of t-butyllithium in n-pentane (5.64 mL, 9.6 mmol) and trimethyl borate (1.02 mL, 9.6 mmol), the title compound was obtained as a foam that was used as such for the next step without purification and characterization.

7-Benzyl-3,3-dimethyl-5-(3-hydroxy-1-methyl-prop-(1Z)-enyl)-2,3-dihydro-benzofuran (Intermediate 41)

Following General Procedure B and using 7-benzyl-3,3-dimethyl-2,3-dihydro-benzofuran-5-boronic acid (Intermediate 40, crude, obtained from the previous step, 4.81 mmol), 3-iodo-but-2 (Z)-ene-ol (0.88 g, 4.47 mmol), methanol (5 mL), toluene (25 mL), water (2 mL), potassium carbonate (1.23 g, 8.94 mmol) and tetrakis (triphenylphosphine)palladium(0)(50 mg), followed by flash column chromatography over silica gel (230–400 mesh) using 30% ethyl acetate in hexane as the eluent the title compound was obtained (0.91 g, 59% over two steps).
$^1$H NMR (300 MHz, CDCl$_3$): δ 7.30–7.12 (m, 5H), 6.78 (d, 1H, J=1.7 Hz), 6.67 (d, 1H, J=1.7 Hz), 5.58 (dt, 1H, J=6.7, 1.3 Hz), 4.24 (s, 2H), 4.02 (d, 2H, J=7.2 Hz), 3.92 (s, 2H), 2.02 (s, 3H), 1.33 (s, 6H).

7-benzyl-3,3-dimethyl-5-[(1S,2S)-3-hydroxy-1.2-methano-1-methyl-propyl]-2,3-dihydro-benzofuran (Intermediate 42)

Following General Procedure C and using 1M diethylzinc in anhydrous dichloromethane (35.4 mL, 35.4 mmol), 1,2-dimethoxyethane (3.68 mL, 35.4 mmol), diiodomethane (5.71 mL, 71 mmol), 7-benzyl-3,3-dimethyl-5-(3-hydroxy-1-methyl-prop-(1Z)-enyl)-2,3-dihydro-benzofuran (Intermediate 41, 0.91 g, 2.95 mmol), 4A° molecular sieves powder (1.36 g) and (4S-trans)-2-butyl-N,N,N',N'-tetramethyl[1,3,2]dioxaborolane-[4,5]dicarboxamide (1.67 g, 6.2 mmol) in 5 mL of anhydrous dichloromethane followed by flash column chromatography the title compound was obtained as a brown oil (0.92 g,100%).
$^1$H NMR (300 MHz, CDCl$_3$): δ 7.34–7.19 (μ, 5H), 6.94 (δ, 1H, Θ=1.8 Hζ), 6.87 (δ, 1H, Θ=1.8 Hζ), 4.26 (σ, 2H), 3.99 (δ, 1H, Θ=5.3 Hζ), 3.90 (δ, 1H, Θ=5.3 Hζ), 3.25 (δδ, 1H, Θ=11.5, 6.6 Hζ), 3.17 (δδ, 1H, Θ=11.5, 7.7 Hζ), 1.35 (σ, 9H), 1.35–1.20 (μ, 1H), 0.79–0.72 (μ, 2H).

(1S)-Camphanate Ester of 7-benzyl-3,3-dimethyl-5-[(1S, 2S)-3-hydroxy-1.2-methano-1-methyl-propyl]-2,3-dihydro-benzofuran (Intermediate 43)

Following General Procedure D and using 7-benzyl-3,3-dimethyl-5-[(1S,2S)-3-hydroxy-1,2-methano-1-methyl-propyl]-2,3-dihydro-benzofuran (Intermediate 42, 0.92 g, 2.95 mmol), anhydrous dichloromethane (10 mL), triethylamine (1.64 mL, 11.8 mmol) and (1S)-camphanic chloride (1.27 g, 5.9 mmol) followed by flash column chromatography and preparative normal phase HPLC to eliminate the minor isomer formed during the cyclopropanation, the title compound was obtained.

¹H NMR (300 MHz, d₆-Acetone): δ 7.29–7.12 (m, 5H), 7.06 (d, 1H, J=1.9 Hz), 6.99 (d, 1H, J=1.9 Hz), 4.22 (s, 2H), 3.92 (s, 2H), 3.87 (dd, 1H, J=11.5, 7.7 Hz), 3.78 (dd, 1H, J=11.5, 7.7 Hz), 2.44–3.35 (m, 1H), 2.05–1.85 (m, 2H), 1.64–1.55 (m, 1H), 1.36–1.27 (m, 1H), 1.32 (s, 6H), 1.31 (s, 3H), 1.07 (s, 3H) 1.04 (s, 3H) 0.94 (s, 3H) 0.94–0.90 (m, 1H), 0.86–0.82 (m, 1H).

7-benzyl-3,3-dimethyl-5-[(1S,2S)-3-hydroxy-1,2-methano-1-methyl-propyl]-2,3-dihydro-benzofuran (Intermediate 42a)

Following General Procedure E and the using the (1S)-camphanate ester of 7-benzyl-3,3-dimethyl-5-[(1S,2S)-3-hydroxy-1,2-methano-1-methyl-propyl]-2,3-dihydro-benzofuran (Intermediate 43, as obtained from previous step, 2.95 mmol), 10 mL of ethanol, a 5M solution of sodium hydroxide (3 mL), the title compound was obtained (0.404 g, 44% for 2 steps) as a pale yellow oil.

¹H NMR (300 MHz, CDCl₃): δ 7.34–7.19 (m, 5H), 6.94 (d, 1H, J=1.8 Hz), 6.87 (d, 1H, J=1.8 Hz), 4.26 (s, 2H), 3.99 (d, 1H, J=5.3 Hz), 3.90 (d, 1H, J=5.3 Hz), 3.25 (dd, 1H, J=11.5, 6.6 Hz), 3.17 (dd, 1H, J=11.5, 7.7 Hz), 1.35 (s, 9H), 1.35–1.20 (m, 1H), 0.79–0.72 (m, 2H).

7-Benzyl-3,3-dimethyl-5-r[(1S,2S)-1,2-methano-1-methyl-3-oxo-propyl]-2,3-dihydro-benzofuran (Intermediate 44)

Following General Procedure F and using 7-benzyl-3,3-dimethyl-5-[(1S,2S)-3-hydroxy-1,2-methano-1-methyl-propyl]-2,3-dihydro-benzofuran (Intermediate 42a, 0.404 g, 1.25 mmol), dichloromethane (12 mL), acetonitrile (2 mL), 4A° molecular sieves powder (0.3 g), tetra-n-propylammoniumperruthenate (0.03 g) and N-methylmorpholine-N-oxide (0.5⁸ g, 4.95 mmol) followed by flash column chromatography, the title compound was obtained (0.4 g, 100%) as a colorless oil.

¹H NMR (300 MHz, CDCl₃): δ 8.39 (d, 1H, J=7.0 Hz), 7.28–7.12 (m, 5H), 6.90 (d, 1H, J=1.6 Hz), 6.86 (d, 1H, J=1.6 Hz), 4.20 (s, 2H), 3.89 (s, 2H), 1.88–1.75 (m, 2H), 1.37 (s, 3H), 1.32–1.27 (m, 1H), 1.30 (s, 3H), 1.28 (s, 3H).

(6S,7S)-7-[5-(7-Benzyl-3,3-dimethyl-2,3-dihydro-benzofuranyl)]-6,7-methano-3-methyl-octa-2E,4E-dienoic Acid Ethyl Ester (Compound 13)

Following General Procedure G and using methyl-3-methyl-4-diethylphosphonocrotonate (2.32 g, 8.78 mmol), 20 mL of anhydrous tetrahydrofuran, 4 mL of 1,3-dimethyl-3,4,5,6-tetrahydro-2 (1H)-pyrimidinone (DMPU), 1.6M solution of n-butyllithium in hexanes (5.48 mL, 8.78 mmol), and 7-benzyl-3,3-dimethyl-5-[(1 S,2S)-1,2-methano-1-methyl-3-oxo-propyl]-2,3-dihydro-benzofuran (Intermediate 44, 0.4 g, 1.25 mmol) in tetrahydrofuran (3 mL) the title compound contaminated with the 2Z isomer was obtained. Preparative normal phase HPLC using 3.5% ethyl acetate in hexane as the mobile phase afforded the title compound (0.332 g, 61.5% after HPLC).

¹H NMR (300 MHz, CDCl₃): δ 7.27–7.11 (m, 5H), 6.83 (d, 1H, J=1.7 Hz), 6.80 (d, 1H, J=1.7 Hz), 6.14 (d, 1H, J=15.5 Hz), 5.62 (s, 1H), 5.19 (dd, 1H, J=15.5, 9.9 Hz), 4.21 (s, 2H), 4.15 (q, 2H, J=7.1 Hz), 3.95 (d, 1H, J=15.2 Hz), 3.85 (d, 1H, J=15.0 Hz), 1.95 (s, 3H), 1.70–1.61 (m, 1H), 1.36 (s, 3H), 1.32 (s, 3H), 1.28 (s, 3H), 1.27 (t, 3H, J=7.2 Hz), 1.14–1.10 (m, 1H), 1.06–1.03 (m, 1H).

(6S,7S)-7-[5-(7-Benzyl-3,3-dimethyl-2,3-dihydro-benzofuranyl)]-6,7-methano-3-methyl-octa-2E,4E-dienoic Acid (Compound 14)

Following General Procedure H and using (6S,7S)-7-[5-(7-benzyl-3,3-dimethyl-2,3-dihydro-benzofuranyl)]-6,7-methano-3-methyl-octa-2E,4E-dienoic acid ethyl ester (Compound 13, 0.146 g, 0.34 mmol), methanol and aqueous sodium hydroxide followed by flash column chromatography and preparative reverse phase HPLC using 12% water in acetonitrile as the mobile phase, the title compound was obtained (0.060 g, 41%) as a white solid.

¹H NMR (300 MHz, CDCl₃): δ 7.27–7.15 (m, 5H), 6.83 (d, 1H, J=1.8 Hz), 6.79 (d, 1H, J=1.8 Hz), 6.17 (d, 1H, J=15.5 Hz), 5.63 (s, 1H), 5.24 (dd, 1H, J=15.5, 10.0 Hz), 4.21 (s, 2H), 3.95 (d, 1H, J=15.2 Hz), 3.85 (d, 1H, J=15.1 Hz), 1.95 (s, 3H), 1.71–1.63 (m, 1H), 1.36 (s, 3H), 1.32 (s, 3H), 1.28 (s, 3H), 1.16–1.12 (m, 1H), 1.08–1.04 (m, 1H).

(5-Bromo-3,3-dimethyl-2,3-dihydro-benzofuran-7-yl)-cyclohexyl-methanol (Intermediate 45)

Following General Procedure K and using 5-bromo-3,3-dimethyl-2,3-dihydrobenzofuran-7-carbaldehyde (Intermediate 30, 0.765 g, 3 mmol), 10 mL of anhydrous diethyl ether, and a 2M solution of cyclohexyl magnesium chloride solution in ether (3 mL, 6 mmol) followed by flash column chromatography using 10% ethyl acetate in hexane, the title compound was obtained (0.62 g, 61%).

¹H NMR (300 MHz, CDCl₃): δ 7.19 (d, 1H, J=2.0 Hz), 7.08 (d, 1H, J=2.0 Hz), 4.42 (t, 1H, J=6.8 Hz), 4.22 (ABq, 2H), 2.43 (d, 1H, J=6.2 Hz), 2.00–1.90 (m, 1H), 1.80–1.60 (m, 4H), 1.50–1.35 (m, 1H), 1.30–1.00 (m, 4H),1.32 (s, 6H).

5-Bromo-7-cyclohexylmethyl-3,3-dimethyl-2,3-dihydro-benzofuran (Intermediate 46)

Following General Procedure J and using (5-bromo-3,3-dimethyl-2,3-dihydro-benzofuran-7-yl)-cyclohexyl-methanol (Intermediate 45, 0.62 g, 1.94 mmol), trifluoroacetic acid (4 mL, 52 mmol) and triethyl silane (1.5 mL, 9.4 mmol) followed by flash column chromatography using 3% ethyl acetate in hexane as the eluent, the title compound was obtained (0.58 g, 92%).

¹H NMR (300 MHz, CDCl₃): δ 7.06 (s, 2H), 4.22 (s, 2H), 2.44 (d, 2H, J=7.1 Hz), 1.80–1.60 (m, 5H), 1.34 (s, 6H), 1.30–1.20 (m, 4H), 1.10–0.90 (m, 2H).

7-Cyclohexylmethyl-3,3-dimethyl-2,3-dihydro-benzofuran-5-boronic acid (Intermediate 47)

Following General Procedure A and using 5-bromo-7-cyclohexylmethyl-3,3-dimethyl-2,3-dihydro-benzofuran (Intermediate 46, 0.58 g, 1.79 mmol),15 mL of anhydrous diethyl ether, 1.7M solution of t-butyllithium in n-pentane (2.21 mL, 3.77 mmol) and trimethyl borate (0.42 mL, 3.77 mmol) the title compound was obtained as a foam that was used as such for the next step without purification and characterization.

7-Cyclohexylmethyl-3,3-dimethyl-5-(3-hydroxy-1-methyl-prop-(1Z)-enyl-2,3-dihydro-benzofuran (Intermediate 48)

Following General Procedure B and using 7-cyclohexylmethyl-3,3-dimethyl-2,3-dihydro-benzofuran-5-boronic acid (Intermediate 47, crude, obtained from the previous step, 1.79 mmol), 3-iodo-but-2 (Z)-ene-ol (0.4 g, 2 mmol), methanol (4 mL), toluene (8 mL), water (2 mL), sodium carbonate (0.64 g, 6.05 mmol) and tetrakis (triphenylphosphine)palladium(0)(90 mg), followed by flash column chromatography over silica gel (230–400 mesh) using 13% ethyl acetate in hexane as the eluent the title compound was obtained (0.35 g, 57% over two steps).

¹H NMR (300 MHz, CDCl₃): δ 6.76 (d, 1H, J=1.7 Hz), 6.71 (d, 1H, J=1.7 Hz), 5.63 (dt, 1H, J=1.4, 6.7 Hz), 4.22 (s, 2H), 4.13 (d, 2H, J=6.6 Hz), 2.44 (d, 2H, J=7.0 Hz), 2.08 (s, 3H), 1.80–1.50 (m, 5H), 1.33 (s, 6H), 1.33–1.10 (m, 4H), 1.10–0.90 (m, 2H).

7-Cyclohexylmethyl-3.3-dimethyl-5-[(1S,2S)-3-hydroxy-1,2-methano-1-methyl-propyl]-2,3-dihydro-benzofuran (Intermediate 49)

Following General Procedure C and using 1.08M diethylzinc in anhydrous dichloromethane (18.5 mL, 20 mmol), 1,2-dimethoxyethane (20.1 mL, 20 mmol), diiodomethane (3.22 mL, 40 mmol), 7-cyclohexylmethyl-3,3-dimethyl-5-(3-hydroxy-1-methyl-prop-(1Z)-enyl)-2,3-dihydro-benzofuran (Intermediate 48, 0.35 g, 1.04 mmol), 4A° molecular sieves powder (0.5 g) and (4R-trans)-2-butyl-NN,N',N'-tetramethyl[1,3,2]dioxaborolane-[4,5]dicarboxamide (0.864 g, 3 mmol) in 5 mL of anhydrous dichloromethane followed by flash column chromatography using 13% ethyl acetate in hexane as the eluent, the title compound was obtained as a brown oil (0.3 g, 92%).

$^1$H NMR (300 MHz, CDCl$_3$): δ 6.88 (d, 1H,J=1.7 Hz), 6.84 (d, 1H,J=1.7 Hz), 4.18 (s, 2H), 3.30–3.16 (m, 2H), 2.47–2.41 (m, 2H), 1.80–1.50 (m, 6H), 1.37 (s, 3H), 1.31 (s, 3H), 1.30 (s, 3H), 1.30–1.08 (m, 4H), 1.05–0.85 (m, 2H), 0.83 (t, 1H,J=4.8 Hz), 0.76–0.72 (m, 1H).

(1S)-Camphanate Ester of 7-cyclohexylmethyl-3,3-dimethyl-5-[(1S,2S)-3-hydroxy-1,2-methano-1-methyl-propyl]-2,3-dihydro-benzofuran (Intermediate 50)

Following General Procedure D and using 7-cyclohexylmethyl-3,3-dimethyl-5-[(1S,2S)-3-hydroxy-1,2-methano-1-methyl-propyl]-2,3-dihydro-benzofuran (Intermediate 49, 0.3 g, 0.86 mmol), anhydrous dichloromethane (6 mL), triethylamine (0.5 mL, 3.44 mmol) and (1S)-camphanic chloride (0.37 g, 1.72 mmol) followed by flash column chromatography and preparative normal phase HPLC using 10% ethyl acetate in hexane as the mobile phase to separate the isomers formed during the cyclopropanation, the title compound was obtained (minor isomer, 0.03 g, 6.6%; major isomer, 0.27 g, 59%). Minor isomer:

$^1$H NMR (300 MHz, CDCl$_3$): δ 6.87 (d, 1H, J=1.8 Hz), 6.81 (d, 1H, J=1.8 Hz), 4.19 (s, 2H), 3.95 (dd, 1H,J=11.4, 7.2 Hz), 3.77 (dd, 1H,JJ=11.4, 7.7 Hz), 2.45–2.36 (m, 3H), 2.04–1.87 (m, 2H), 1.70–1.52 (m, 6H), 1.40–0.80 (m, 6H), 1.36 (s, 3H), 1.32 (s, 3H), 1.31 (s, 3H), 1.13 (s, 3H), 1.05 (s, 3H), 0.98 (s, 3H). Major isomer:

$^1$H NMR (300 MHz, CDCl$_3$): δ 6.84 (s, 1H), 6.80 (s, 1H), 4.18 (s, 2H), 4.00 (dd, 1H, J=11.5, 7.0 Hz), 3.73 (dd, 1H, J=11.5, 7.9 Hz), 2.48–2.39 (m, 3H), 2.07–1.87 (m, 2H), 1.73–1.50 (m, 6H), 1.40–0.80 (m, 6H), 1.36 (s, 3H), 1.32 (s, 3H), 1.30 (s, 3H), 1.12 (s, 3H), 1.07 (s, 3H), 0.96 (s, 3H).

7-Cyclohexylmethyl-3,3-dimethyl-5-[(1S,2S)-3-hydroxy-1,2-methano-1-methyl-propyl]-2,3-dihydro-benzofuran (Intermediate 49a)

Following General Procedure E and the using the (1S)-camphanate ester of 7-cyclohexylmethyl-3,3-dimethyl-5-[(1S,2S)-3-hydroxy-1,2-methano-1-methyl-propyl]-2,3-dihydro-benzofuran (Intermediate 50, 0.03 g, 0.056 mmol), 1 mL of methanol, 1 mL of tetrahydrofuran, 0.5 mL of water and lithium hydroxide monohydrate (0.05 g, 1.19 mmol), the title compound was obtained (0.017 g, 86%).

$^1$H NMR (300 MHz, CDCl$_3$): δ 6.88 (d, 1H, J=1.7 Hz), 6.84 (d, 1H, J=1.7 Hz), 4.18 (s, 2H), 3.30–3.16 (m, 2H), 2.47–2.41 (m, 2H), 1.80–1.50 (m, 6H), 1.37 (s, 3H), 1.31 (s, 3H), 1.30 (s, 3H), 1.30–1.08 (m, 4H), 1.05–0.85 (m, 2H), 0.83 (t, 1H, J=4.8 Hz), 0.76–0.72 (m, 1H).

7-Cyclohexylmethyl-3,3-dimethyl-5-[(1S,2S)-1,2-methano-1-methyl-3-oxo-propyl]-2,3-dihydro-benzofuran (Intermediate 51)

Following General Procedure F and using 7-cyclohexylmethyl-3,3-dimethyl-5-[(1S,2S)-3-hydroxy-1,2-methano-1-methyl-propyl]-2,3-dihydro-benzofuran (Intermediate 49a, 0.017 g, 0.049 mmol), dichloromethane (2.5 mL), acetonitrile (0.5 mL), 4A° molecular sieves powder (0.2 g), tetra-n-propylammoniumperruthenate (0.01 g) and N-methylmorpholine-N-oxide (0.097 g, 0.83 mmol) followed by flash column chromatography, the title compound was obtained (0.015 g, 88%).

$^1$H NMR (300 MHz, CDCl$_3$): δ 8.40 (d, 1H, J=7.0 Hz), 6.88 (d, 1H, J=1.9 Hz), 6.85 (d, 1H, J=1.9 Hz), 4.19 (s, 2H), 2.41 (d, 2H, J=7.1 Hz), 1.92–1.82 (m, 2H), 1.80–1.45 (m, 5H), 1.43 (s, 3H), 1.40–1.36 (m, 1H), 1.31 (s, 3H), 1.29 (s, 3H), 1.29–1.15 (m, 4H), 0.99–0.91 (m, 2H), 1.31 (s, 3H), 1.29 (s, 3H), 0.90 (s, 9H).

(6S,7S)-7-[5-(7-Cyclohexylmethyl-3,3-dimethyl-2,3-dihydro-benzofuranyl)]-6,7-methano-3-methyl-octa-2E,4E-dienoic Acid Ethyl Ester (Compound 15)

Following General Procedure G and using methyl-3-methyl-4-diethylphosphonocrotonate (1.06 g, 4.04 mmol), 12 mL of anhydrous tetrahydrofuran, 1.5 mL of 1,3-dimethyl-3,4,5,6-tetrahydro-2 (1H)-pyrimidinone (DMPU), 1.6M solution of n-butyllithium in hexanes (1.9 mL, 3.04 mmol), and 7-cyclohexylmethyl-3,3-dimethyl-5-[(1S,2S)-1,2-methano-1-methyl-3-oxo-propyl]-2,3-dihydro-benzofuran (Intermediate 51, 0.015 g, 0.043 mmol) in tetrahydrofuran (2 mL) the title compound was obtained (0.02 g, 100%).

$^1$H NMR (300 MHz, CDCl$_3$): δ 6.80 (s, 1H), 6.78 (s, 1H), 6.17 (d, 1H, J=15.6 Hz), 5.62 (s, 1H), 5.23 (dd, 1H, J=15.5, 10 Hz), 4.19 (s, 2H), 4.13 (q, 2H, J=7.2 Hz), 2.50–2.32 (m, 2H), 1.98 (s, 3H), 1.80–1.20 (m, 15H), 1.44 (s, 3H), 1.40 (s, 3H), 1.32 (s, 3H), 1.00–0.80 (m, 2H).

(6S,7S)-7-[5-(7-Cyclohexylmethyl-3,3-dimethyl-2,3-dihydro-benzofuranyl)]-6,7-methano-3-methyl-octa-2E,4E-dienoic Acid (Compound 16)

Following General Procedure H and using (6S,7S)-7-[5-(7-cyclohexylmethyl-3,3-dimethyl-2,3-dihydro-benzofuranyl)]-6,7-methano-3-methyl-octa-2E,4E-dienoic acid ethyl ester (Compound 15, 0.02 g, 0.043 mmol), methanol (2 mL), tetrahydrofuran (2 nL) and 1M aqueous sodium hydroxide (1 mL) followed by flash column chromatography using 16% ethyl acetate in hexane as the eluent, the title compound was obtained (0.01 Ig, 61%) as a white solid.

$^1$H NMR (300 MHz, CDCl$_3$): δ 6.80 (s, 1H), 6.78 (s, 1H), 6.17 (d, 1H, J=15.7 Hz), 5.62 (s, 1H), 5.29 (dd, 1H, J=15.7, 10 Hz), 4.20 (s, 2H), 2.50–2.32 (m, 2H), 1.98 (s, 3H), 1.80–1.10 (m, 12H), 1.41 (s, 3H), 1.32 (s, 3H), 1.27 (s, 3H), 1.00–0.80 (m, 2H).

5-Bromo-7-hexanoyl-3,3-dimethyl-2,3-dihydro-benzofuran (Intermediate 52)

Following General Procedure I and using aluminum chloride 1.76 g, 13.2 mmol), 20 mL of anhydrous dichloromethane, hexanoyl chloride (1.76 g, 13.2 mmol) and 5-bromo-3,3-dimethyl-2,3-dihydro-benzofuran (Intermediate 2, 1.5 g, 6.61 mmol) followed by flash column chromatography on silica gel (230–400 mesh) using 3% ethyl acetate in hexane as the eluent, the title compound was obtained as a yellow oil. It was used as such for the next step.

$^1$H NMR (300 MHz, CDCl$_3$): δ 7.81 (d, 1H, J=2.2 Hz), 7.31 (d, 1H, J=2.2 Hz), 4.37 (s, 2H), 2.96 (t, 2H, J=7.4 Hz), 1.73–1.62 (m, 2H), 1.36 (s, 6H), 1.35–1.30 (m, 4H), 0.90 (t, 3H, J=6.9 Hz).

5-Bromo-3,3-dimethyl-7-hexyl-2,3-dihydro-benzofuran (Intermediate 53)

Following General Procedure J and using 5-bromo-3,3-dimethyl-7-hexanoyl-2,3-dihydrobenzofuran (Intermediate 52, 0.325 g, 1.0 mmol), trifluoroacetic acid (0.31 mL, 4 mmol), triethyl silane (0.64 mL, 4 mmol) and dichloromethane (5 mL) followed by flash column chromatography using 2% ethyl acetate in hexane as the eluent, the title compound was obtained (0.20 g, 64% for 2 steps).

$^1$H NMR (300 MHz, CDCl$_3$): δ 7.06 (d, 11H, J=2.0 Hz), 7.01 (d, 11H, J=2.1 Hz), 4.19 (s, 2H), 2.51 (t, 2H, J=7.8 Hz), 1.63–1.50 (m, 2H), 1.38–1.20 (m, 6H), 1.29 (s, 6H), 0.88 (t, 3H, J=6.8 Hz).

3,3-Dimethyl-7-hexyl-2,3-dihydro-benzofuran-5-boronic acid (Intermediate 54)

Following General Procedure A and using 5-bromo-7-hexyl-3,3-dimethyl-2,3-dihydro-benzofuran (Intermediate 53, 1.32 g, 4.26 mmol), anhydrous tetrahydrofuran, 1.7M solution of t-butyllithium in n-pentane and trimethyl borate, the title compound was obtained as a foam that was used as such for the next step without purification and characterization.

3,3-Dimethyl-7-hexyl-5-(3-hydroxy-1-methyl-prop-(1Z)-enyl)-2,3-dihydro-benzofuran (Intermediate 55)

Following General Procedure B and using 3,3-dimethyl-7-hexyl-2,3-dihydro-benzofuran-5-boronic acid (Intermediate 54, crude, obtained from the previous step, 4.26 mmol), 3-iodo-but-2 (Z)-ene-ol (0.76 g, 3.83 mmol), methanol (5 mL), toluene (20 mL), water (2 mL), sodium carbonate (1.06 g, 7.66 mmol) and tetrakis(triphenylphosphine)palladium(0)(50 mg), followed by flash column chromatography over silica gel (230–400 mesh) using 15% ethyl acetate in hexane as the eluent the title compound was obtained (0.44 g, 34% over two steps).
$^1$H NMR (300 MHz, CDCl$_3$): δ 6.78 (s, 2H), 5.63 (dt, 1H, J=6.7, 1.3 Hz), 4.23 (s, 2H), 4.12 (d, 2H, J=6.7 Hz), 2.57 (t, 2H, J=7.8 Hz), 2.08 (s, 3H), 1.67–1.56 (m, 2H), 1.40–1.29 (m, 6H), 1.34 (s, 6H), 0.90 (t, 3H, J=6.8 Hz).

3,3-dimethyl-7-hexyl-5-[(1S,2S)-3-hydroxy-1,2-methano-1-methyl-propyl]-2,3-dihydro-benzofuran (Intermediate 56)

Following General Procedure C and using 1M diethylzinc in anhydrous dichloromethane (17.3 mL, 17.3 mmol), 1,2-dimethoxyethane (1.8 mL, 17.3 mmol), diiodomethane (2.8 mL, 34.6 mmol), 3,3-dimethyl-7-hexyl-5-(3-hydroxy-1-methyl-prop-(1Z)-enyl)-2,3-dihydro-benzofuran (Intermediate 55, 0.44 g, 1.44 mmol), 4A° molecular sieves powder (0.65 g) and (4R-trans)-2-butyl-N,N,N',N'-tetramethyl[1,3,2]dioxaborolane-[4,5]dicarboxamide (0.82 g, 3 mmol) in 5 mL of anhydrous dichloromethane followed by flash column chromatography using 30% ethyl acetate in hexane as the eluent, the title compound was obtained as a brown oil (0.455 g, 100%).
$^1$H NMR (300 MHz, CDCl$_3$): δ 6.91 (d, 1H, J=1.9 Hz), 6.88 (d, 1H, J=1.9 Hz), 4.21 (s, 2H), 3.24 (d, 2H, J=4.5 Hz), 2.54 (t, 2H, J=7.5 Hz), 1.63–1.55 (m, 2H), 1.38 (s, 3H), 1.38–1.20 (m, 7H), 1.32 (s, 6H), 0.89 (t, 3H, J=7.0 Hz) 0.89–0.83 (m, 1H), 0.78–0.73 (m, 1H).

(1S)-Camphanate Ester of 3,3-dimethyl-7-hexyl-5-[(1S,2S)-3-hydroxy-1,2-methano-1-methyl-propyl]-2,3-dihydro-benzofuran (Intermediate 57)

Following General Procedure D and using 3,3-dimethyl-7-hexyl-5-[(1S,2S)-3-hydroxy-1,2-methano-1-methyl-propyl]-2,3-dihydro-benzofuran (Intermediate 56, 0.455 g, 1.44 mmol), anhydrous dichloromethane (10 mL), triethylamine (0.8 mL, 5.7 mmol) and (1S)-camphanic chloride (0.63 g, 2.9 mmol) followed by flash column chromatography and preparative normal phase HPLC to separate the isomers formed during the cyclopropanation, the title compound was obtained.
$^1$H NMR (300 MHz, CDCl$_3$): δ 6.87 (s, 2H), 4.20 (s, 2H), 3.93 (dd, 1H, J=11.5, 7.4 Hz), 3.80 (dd, 1H, J=11.4, 7.4 Hz), 2.53 (t, 2H, J=7.8 Hz), 2.45–2.35 (m, 1H), 2.03–1.87 (m, 2H), 1.76–1.66 (m, 1H), 1.64–1.53 (m, 2H), 1.37–1.28 (m, 7H), 1.34 (s, 3H), 1.32 (s, 3H), 1.31 (s, 3H), 1.13 (s, 3H), 1.05 (s, 3H), 0.99 (s, 3H), 0.88 (t, 3H, J=7.1 Hz), 1.37–0.82 (m, 2H).

3,3-dimethyl-7-hexyl-5-[(1S,2S)-3-hydroxy-1.2-methano-1-methyl-propyl]-2,3-dihydro-benzofuran (Intermediate 56a)

Following General Procedure E and the using the (1S)-Camphanate ester of 3,3-dimethyl-7-hexyl-5-[(1S,2S)-3-hydroxy-1,2-methano-1-methyl-propyl]-2,3-dihydro-benzofuran (Intermediate 57, obtained from previous step, 1.44 mmol), 10 mL of methanol, 2 mL of tetrahydrofuran, and 2 mL of 5M sodium hydroxide solution, the title compound was obtained (0.2 g, 47% over 3 steps).
$^1$H NMR (300 MHz, CDCl$_3$): δ 6.91 (d, 1H, J=1.9 Hz), 6.88 (d, 1H, J=1.9 Hz), 4.21 (s, 2H), 3.24 (d, 2H, J=4.5 Hz), 2.54 (t, 2H, J=7.5 Hz), 1.63–1.55 (m, 2H), 1.38 (s, 3H), 1.38–1.20 (m, 7H), 1.32 (s, 6H), 0.89 (t, 3H, J=7.0 Hz) 0.89–0.83 (m, 1H), 0.78–0.73 (m, 1H).

3,3-dimethyl-7-hexyl-5-[(1S,2S)-1,2-methano-1-methyl-3-oxo-propyl]-2,3-dihydro-benzofuran (Intermediate 58)

Following General Procedure F and using 3,3-dimethyl-7-hexyl-5-[(1S,2S)-3-hydroxy-1,2-methano-1-methyl-propyl]-2,3-dihydro-benzofuran (Intermediate 56a, 0.2 g, 0.63 mmol), dichloromethane (2 mL), acetonitrile (12 mL), 4A° molecular sieves powder (0.3 g), tetra-n-propylammoniumperruthenate (0.03 g) and N-methylmorpholine-N-oxide (0.15 g, 1.27 mmol) followed by flash column chromatography, the title compound was obtained.
$^1$H NMR (300 MHz, CDCl$_3$): δ 8.41 (d, 1H, J=6.9 Hz), 6.91 (d, 1H, J=1.8 Hz), 6.88 (d, 1H, J=1.8 Hz), 4.20 (s, 2H), 2.53 (t, 2H, J=7.8 Hz), 1.92–1.81 (m, 2H), 1.63–1.52 (m, 2H), 1.43 (s, 3H), 1.41–1.28 (m, 7H), 1.31 (s, 3H), 1.29 (s, 3H), 0.88 (t, 3H, J=6.8 Hz).

(6S,7S)-7-[5-(3,3-Dimethyl-7-hexyl-2,3-dihydro-benzofuranyl)]-6,7-methano-3-methyl-octa-2E,4E-dienoic acid ethyl ester (Compound 17)

Following General Procedure G and using methyl-3-methyl-4-diethylphosphonocrotonate (0.835 g, 3.16 mmol), 10 mL of anhydrous tetrahydrofuran, 1.5 mL of 1,3-dimethyl-3,4,5,6-tetrahydro-2 (1H)-pyrimidinone (DMPU), 1.6M solution of n-butyllithium in hexanes (1.98 mL, 3.2 mmol), and 3,3-dimethyl-7-hexyl-5-[(1S,2S)-1,2-methano-1-methyl-3-oxo-propyl]-2,3-dihydro-benzofuran (Intermediate 58, as obtained from previous step, 0.63 mmol) in tetrahydrofuran (2 mL) the title compound was obtained (0.21 g, 64.5% for two steps) after preparative normal phase HPLC using 1.5% ethyl acetate in hexane as the mobile phase.
$^1$H NMR (300 MHz, CDCl$_3$): δ 6.86 (d, 1H, J=1.9 Hz), 6.80 (d, 1H, J=1.9 Hz), 6.20 (d, 1H, J=15.5 Hz), 5.64 (s, 1H), 5.26 (dd, 1H, J=15.5, 10.0 Hz), 4.21 (s, 2H), 4.15 (q, 2H, J=7.1 Hz), 2.63–2.45 (m, 2H), 2.02 (s, 3H), 1.72–1.65 (m, 1H), 1.62–1.52 (m, 2H), 1.41 (s, 3H), 1.39–1.26 (m, 6H), 1.33 (s, 3H), 1.28 (s, 3H), 1.27 (t, 3H, J=7.2 Hz), 1.19–1.15 (m, 1H), 1.12–1.08 (m, 1H), 0.89 (t, 3H, J=6.6 Hz).

(6S,7S)-7-[5-(3,3-Dimethyl-7-hexyl-2,3-dihydro-benzofuranyl)]-6,7-methano-3-methyl-octa-2E,4E-dienoic acid (Compound 18)

Following General Procedure H and using (6S,7S)-7-[5-(3,3-dimethyl-7-hexyl-2,3-dihydro-benzofuranyl)]-6,7-methano-3-methyl-octa-2E,4E-dienoic acid ethyl ester (Compound 17, 0.173 g, 0.41 mmol), methanol, tetrahydrofuran and 1M aqueous sodium hydroxide followed by preparative reverse phase HPLC using 10% water in acetonitrile as the mobile phase, the title compound was obtained (0.098 g, 73%) as a clear oil.
$^1$H NMR (300 MHz, CDCl$_3$): δ 6.84 (d, 1H, J=1.7 Hz), 6.79 (d, 1H, J=1.7 Hz), 6.21 (d, 1H, J=15.4 Hz), 5.64 (s, 1H), 5.29 (dd, 1H, J=15.5, 10.0 Hz), 4.20 (s, 2H), 2.62–2.44 (m, 2H), 1.99 (s, 3H), 1.72–1.65 (m, 1H), 1.60–1.52 (m, 2H), 1.40 (s, 3H), 1.38–1.27 (m, 6H), 1.32 (s, 3H), 1.26 (s, 3H), 1.20–1.15 (m, 1H), 1.12–1.08 (m, 1H), 0.87 (t, 3H, J=6.7 Hz).

(1S)-Camphanate ester of 7-bromo-3,3-dimethyl-5-[(1S, 2S)-3-hydroxy-1,2-methano-1-methyl-propyl]-2,3-dihydrobenzofuran (Intermediate 59)

A stirred, cooled (ice-bath) solution of the (1S)-camphanate ester of 3,3-dimethyl-5-[(1S,2S)-3-hydroxy-1,2-methano-1-methyl-propyl]-2,3-dihydro-benzofuran (Intermediate 6, 1 g, 2.42 mmol), in methanol(15 mL) was treated with a solution of bromine (0.47 gmL, 2.91 mmol). The reaction mixture was allowed to warm to room temperature and stirred for 2.5 h. The volatiles were evaporated in vacuo, the residue was dissolved in ethyl acetate and washed with saturated aqueous sodium bicarbonate solution and brine. The organic phase was dried over anhydrous magnesium sulfate, filtered and evaporated in vacuo to a residue that on flash column chromatography using 25% ethyl acetate in hexane as the eluent afforded the title compound as a white solid (1.3 g, 99%).

$^1$H NMR (300 MHz, CDCl$_3$): δ 7.24 (d, 1H, J=1.5 Hz), 7.02 (d, 1H, J=1.5 Hz), 4.31 (s, 2H), 4.03 (dd, 1H, J=11.5, 6.6 Hz), 3.70 (dd, 1H, J=11.5, 8.6 Hz), 2.48–2.38 (m, 1H), 2.07–1.90 (m, 2H), 1.72–1.64 (m, 1H), 1.42–1.29 (m, 1H), 1.36 (s, 9H), 1.13 (s, 3H), 1.06 (s, 3H), 0.99 (s, 3H), 0.90 (br m, 1H), 0.87 (br m, 1H).

7-Bromo-3,3-dimethyl-5-[(1S,2S)-3-hydroxy-1,2-methano-1-methl-propyl]-2,3-dihydro-benzofuran (Intermediate 60)

Following General Procedure E and the using the (1S)-camphanate ester of 7-bromo-3,3-dimethyl-5-[(1S,2S)-3-hydroxy-1,2-methano-1-methyl-propyl]-2,3-dihydro-benzofuran (Intermediate 59, 0.46 g, 0.94 mmol), 10 mL of ethanol, and 2 mL of 5M sodium hydroxide solution, the title compound was obtained (0.21 g, 72%).

$^1$H NMR (300 MHz, CDCl$_3$): δ 7.24 (d, 1H, J=1.5 Hz), 7.00 (d, 1H, J=1.5 Hz), 4.31 (s, 2H), 3.26 (dd, 1H, J=7.5, 11.2 Hz), 3.90 (dd, 11H, J=7.0, 11.2 Hz), 1.35 (s, 3H), 1.34 (s, 3H), 1.33 (s, 3H), 1.29–1.19 (m, 1H), 0.82–0.76 (m, 2H).

7-Bromo-3,3-dimethyl-5-[(1S,2S)-1,2-methano-1-methyl-3-oxo-propyl]-2,3-dihydro-benzofuran (Intermediate 61)

Following General Procedure F and using 7-bromo-3,3-dimethyl-5-[(1S,2S)-3-hydroxy-1,2-methano-1-methyl-propyl]-2,3-dihydro-benzofuran (Intermediate 60, 0.11 g, 0.36 mmol), dichloromethane (4 mL), acetonitrile (1 mL), 4A° molecular sieves powder (0.3 g), tetra-n-propylammoniumperruthenate (0.025 g) and N-methylmorpholine-N-oxide (0.19 g, 1.62 mmol) followed by flash column chromatography using 20% ethyl acetate in hexane as the eluent, the title compound was obtained (0.1 g, 89%).

$^1$H NMR (300 MHz, CDCl$_3$): δ 8.49 (d, 1H, J=6.7 Hz), 7.27 (d, 1H, J=1.7 Hz), 6.98 (d, 1H, J=1.7 Hz), 4.32 (s, 2H), 1.98–1.91 (m, 1H), 1.87–1.84 (m, 1H), 1.44 (s, 3H), 1.44–1.39 (m, 1H), 1.34 (s, 3H), 1.32 (s, 3H).

(6S,7S)-7-[5-(7-Bromo-3,3-dimethyl-2,3-dihydro-benzofuranyl)]-6,7-methano-3-methyl-octa-2E,4E-dienoic Acid Ethyl Ester (Compound 19)

Following General Procedure G and using methyl-3-methyl-4-diethylphosphonocrotonate (1.32 g, 5 mmol), 10 mL of anhydrous tetrahydrofuran, 2 mL of 1,3-dimethyl-3,4,5,6-tetrahydro-2 (1H)-pyrimidinone (DMPU), 1.6M solution of n-butyllithium in hexanes (3.2 mL, 5 mmol), and 7-bromo-3,3-dimethyl-5-[(1S,2S)-1,2-methano-1-methyl-3-oxo-propyl]-2,3-dihydro-benzofuran (Intermediate 61, 0.1 g, 0.32 mmol) in tetrahydrofuran (2 mL) the title compound was obtained (0.13 g, 96%).

$^1$H NMR (300 MHz, CDCl$_3$): δ 7.21 (d, 1H, J=1.3 Hz), 6.89 (d, 1H J=1.3 Hz), 6.20 (d, 1H, J=15.5 Hz), 5.65 (s, 1H), 5.20 (dd, 1H, J=15.5, 10.0 Hz), 4.32 (s, 2H), 4.14 (q, 2H, J=7.0 Hz), 2.01 (s, 3H), 1.77–1.68 (m, 1H), 1.39 (s, 3H), 1.34 (s, 3H), 1.29 (s, 3H), 1.26 (t, 3H, J=7.1 Hz), 1.20–1.16 (m, 1H), 1.10–1.07 (m, 1H).

(6S,7S)-7-[5-(7-Bromo-3,3-dimethyl-2,3-dihydro-benzofuranyl)]-6,7-methano-3-methyl-octa-2E,4E-dienoic Acid (Compound 20)

Following General Procedure H and using (6S,7S)-7-[5-(7-bromo-3,3-dimethyl-2,3-dihydro-benzofuranyl)]-6,7-methano-3-methyl-octa-2E,4E-dienoic acid ethyl ester (Compound 19, 0.06 g, 0.14 mmol), methanol (2 mL), tetrahydrofuran (2 mL) and 1M aqueous sodium hydroxide (2 mL) followed by flash column chromatography using 25% ethyl acetate in hexane as the eluent, the title compound was obtained (0.04 g, 73%) as a pale yellow solid.

$^1$H NMR (300 MHz, CDCl$_3$): δ 7.20 (d, 1H, J=1.5 Hz), 6.87 (d, 1H J=1.5 Hz), 6.23 (d, 1H, J=15.5 Hz), 5.66 (s, 1H), 5.24 (dd, 1H, J=15.5, 10.0 Hz), 4.32 (s, 2H), 2.01 (s, 3H), 1.77–1.69 (m, 1H), 1.39 (s, 3H), 1.34 (s, 3H), 1.28 (s, 3H), 1.24–1.20 (m, 1H), 1.10 (t, 1H, J=5.0 Hz).

3,3-dimethyl-5-[(1S,2S)-3-hydroxy-1.2-methano-1-methyl-propyl]-7-phenyl-2.3-dihydro-benzofuran (Intermediate 62)

Following General Procedure B and using phenylboronic acid (0.09 g, 0.75 mmol), (1S)-camphanate ester of 7-bromo-3,3-dimethyl-5-[(1S,2S)-3-hydroxy-1,2-methano-1-methyl-propyl]-2,3-dihydro-benzofuran (Intermediate 59, 0.25 g, 0.5 mmol), methanol (3 mL), toluene (6 mL), water (1 mL), sodium carbonate (0.1 g, 1 mmol) and tetrakis(triphenylphosphine)palladium(0)(50 mg), followed by treatment with 5 mL of 1M sodium hydroxide solution for 1 h at ambient temperature and flash column chromatography over silica gel (230–400 mesh) using 40% ethyl acetate in hexane as the eluent the title compound was obtained (0.1$^2$ g, 70%).

$^1$H NMR (300 MHz, CDCl$_3$): δ 7.73 (dd, 2H, J=1.6, 8.0 Hz), 7.45 (ddt, 2H, J=1.6, 7.3, 8.0 Hz), 7.32 (dt, 1H, J=1.6, 7.3 Hz), 7.29 (d, 1H, J=1.7 Hz), 7.07 (d, 1H, J=1.7 Hz), 4.30 (s, 2H), 3.32 (d, 2H, J=7.1 Hz), 1.53 (br s, 1H), 1.44 (s, 3H), 1.39 (s, 6H), 1.35–1.26 (m, 1H), 0.90 (t, 1H, J=5.0 Hz), 0.83 (dd, 1H, J=4.8, 8.3 Hz).

3,3-Dimethyl-5-[(1S,2S)-1.2-methano-1-methyl-3-oxo-propyl]-7-phenyl-2.3-dihydro-benzofuran (Intermediate 63)

Following General Procedure F and using 3,3-dimethyl-5-[(1S,2S)-3-hydroxy-1,2-methano-1-methyl-propyl]-7-phenyl-2,3-dihydro-benzofuran (Intermediate 62, 0.12 g, 0.39 mmol), dichloromethane (4 mL), acetonitrile (1 mL), 4A° molecular sieves powder (0.3 g), tetra-n-propylammoniumperruthenate (0.03 g) and N-methylmorpholine-N-oxide (0.12 g, 1 mmol) followed by flash column chromatography using 10% ethyl acetate in hexane as the eluent, the title compound was obtained(0.12 g, 100%).

$^1$H NMR (300 MHz, CDCl$_3$): δ 8.53 (d, 1H, J=6.8 Hz), 7.71 (d, 2H, J=7.9 Hz), 7.44 (dd, 2H, J=7.3, 7.9 Hz), 7.33 (dt, 1H, J=1.1, 7.3 Hz), 7.29 (d, 1H, J=1.8 Hz), 7.07 (d, 1H, J=1.8 Hz), 4.30 (s, 2H), 2.01–1.82 (m, 2H), 1.51 (s, 3H), 1.47–1.43 (m, 1H), 1.39 (s, 3H), 1.38 (s, 3H).

(6S,7S)-7-[5-(3,3-Dimethyl-7-phenyl-2,3-dihydro-benzofuranyl)]-6,7-methano-3-methyl-octa-2E,4E-dienoic acid ethyl ester (Compound 21)

Following General Procedure G and using methyl-3-methyl-4-diethylphosphonocrotonate (1.32 g, 5 mmol), 8 mL of anhydrous tetrahydrofuran, 2 mL of 1,3-dimethyl-3,4,5,6-tetrahydro-2 (1H)-pyrimidinone (DMPU), 1.6M solution of n-butyllithium in hexanes (3.2 mL, 5 mmol), and 3,3-dimethyl-5-[(1S,2S)-1,2-methano-1-methyl-3-oxo-propyl]-7-phenyl-2,3-dihydro-benzofuran (Intermediate 63, 0.12 g, 0.38 mmol) in tetrahydrofuran (4 mL), followed by flash column chromatography using 8% ethyl acetate in hexane as the eluent, and preparative HPLC using 10% ethyl acetate in hexane as the mobile phase, the title compound was obtained (0.1 g, 63%).

¹H NMR (300 MHz, CDCl₃): δ 7.71 (d, 2H, J=7.1 Hz), 7.44 (dd, 2H, J=7.1, 7.8 Hz), 7.32 (t, 1H, J=7.9 Hz), 7.24 (d, 1H, J=1.6 Hz), 6.96 (d, 1H, J=1.6 Hz), 6.25 (d, 1H, J=15.5 Hz), 5.68 (s, 1H), 5.32 (dd, 1H, J=15.5, 10.0 Hz), 4.31 (ABq, 2H, J=8.3 Hz), 4.16 (q, 2H, J=7.1 Hz), 2.05 (s, 3H), 1.76 (m, 1H), 1.46 (s, 3H), 1.39 (s, 3H), 1.34 (s, 3H), 1.29 (t, 3H, J=7.1 Hz), 1.25–1.21 (m, 1H), 1.16 (t, 1H, J=4.9 Hz).

6S,7S)-7-[5-(3,3-Dimethyl-7-phenyl-2,3-dihydro-benzofuranyl)1-6,7-methano-3-methyl-octa-2E,4E-dienoic acid (Compound 22)

Following General Procedure H and using (6S,7S)-7-[5-(3,3-dimethyl-7-phenyl-2,3-dihydro-benzofuranyl)]-6,7-methano-3-methyl-octa-2E,4E-dienoic acid ethyl ester (Compound 21, 0.01 g, 0.24 mmol), methanol (4 mL), tetrahydrofuran (4 mL) and 1M aqueous sodium hydroxide (3 mL) followed flash column chromatography using 25% in hexane as the eluent, the title compound was obtained (0.068 g, 73%) as a pale yellow solid.

¹H NMR (300 MHz, CDCl₃): δ 7.72 (d, 2H, J=7.3 Hz), 7.45 (dd, 2H, J=7.3, 7.5 Hz), 7.32 (t, 1H, J=7.5 Hz), 7.24 (d, 1H, J=1.7 Hz), 6.96 (d, 1H, J=1.7 Hz), 6.28 (d, 1H, J=15.5 Hz), 5.70 (s, 1H), 5.38 (dd, 1H, J=15.5, 10.0 Hz), 4.31 (ABq, 2H, J=8.5 Hz), 2.05 (s, 3H), 1.82–1.74 (m, 1H), 1.47 (s, 3H), 1.39 (s, 3H), 1.34 (s, 3H), 1.28–1.24 (m, 1H), 1.18 (t, 1H, J=4.8 Hz).

2,6-Dimethyl-phenylboronic Acid (Intermediate 64)

Following General Procedure A and using 1-bromo-2,6-dimethyl-benzene (Aldrich, 5 g, 27 mmol), 50 mL of anhydrous tetrahydrofuran, 1.7M solution of t-butyllithium in n-pentane (32 mL, 54 mmol) and trimethyl borate (6.05 mL, 54 mmol), the title compound was obtained after recrystallization from ethyl acetate-hexane mixture (0.7 g, 10%).

¹H NMR (300 MHz, CDCl₃): δ 7.20 (t, 11H, J=7.6 Hz), 7.01 (d, 2H, J=7.7 Hz), 4.56 (s, 2H), 2.40 (s, 6H).

5-{(1S,2S)-2-[7-(2,6-Dimethyl-phenyl)-3,3-dimethyl-2,3-dihydro-benzofuran-5-yl]-2-methyl-cyclopropyl}-3-methyl-penta-2E,4E-dienoic acid ethyl ester (Compound 23)

Following General Procedure B and using 2,6-dimethyl-phenylboronic acid (Intermediate 64, 0.039 g, 0.26 mmol), (6S,7S)-7-[5-(7-bromo-3,3-dimethyl-2,3-dihydro-benzofuuranyl)]-6,7-methano-3-methyl-octa-2E,4E-dienoic acid ethyl ester (Compound 19.0.1 g, 0.24 mmol), methanol (1 mL), toluene (5 mL), water (1 mL), potassium carbonate (0.1 g, 0.72 mmol) and tetrakis(triphenylphosphine)palladium(0)(50 mg), followed by flash column chromatography over silica gel (230–400 mesh), the title compound was obtained (0.109 g, 100%).

¹H NMR (300 MHz, CDCl₃): δ 7.19–7.10 (m, 3H), 7.00 (d, 1H, J=1.8 Hz), 6.83 (d, 1H, J=1.8 Hz), 6.16 (d, 1H, J=15.5 Hz), 5.62 (s, 1H), 5.27 (dd, 1H, J=15.6, 9.9 Hz), 4.19 (s, 2H), 4.15 (q, 2H, J=7.1 Hz), 2.09 (s, 3H), 2.08 (s, 3H), 2.00 (s, 3H), 1.77–1.67 (m, 1H), 1.46 (s, 3H), 1.38 (s, 3H), 1.33 (s, 3H), 1.28 (t, 3H, J=7.1 Hz), 1.19–1.15 (m, 2H).

5-{(1 S 2S)-2-[7-(2,6-Dimethyl-phenyl)-3,3-dimethyl-2,3-dihydro-benzofuran-5-yl]-2-methyl-cyclopropyl}-3-methyl-penta-2E,4E-dienoic acid (Compound 24)

Following General Procedure H and using 5-{(1S, 2S)-2-[7-(2,6-dimethyl-phenyl)-3,3-dimethyl-2,3-dihydro-benzofuran-5-yl]-2-methyl-cyclopropyl}-3-methyl-penta-2E,4 Edienoic acid ethyl ester (Compound 23, 0.109 g, 0.24 mmol), ethanol (15 mL), and 5M aqueous sodium hydroxide (1 mL) followed by flash column chromatography using 25% in hexane as the eluent, and reverse phase HPLC, the title compound was obtained (0.049 g, 50%) as a white solid.

¹H NMR (300 MHz, CDCl₃): δ 7.17–7.07 (m, 3H), 6.97 (d, 1H, J=1.9 Hz), 6.81 (d, 1H, J=1.9 Hz), 6.17 (d, 1H, J=15.5 Hz), 5.62 (s, 1H), 5.30 (dd, 1H, J=15.6, 9.8 Hz), 4.17 (s, 2H), 2.06 (s, 3H), 2.05 (s, 3H), 1.97 (s, 3H), 1.76–1.68 (m, 1H), 1.44 (s, 3H), 1.36 (s, 3H), 1.31 (s, 3H), 1.19–1.15 (m, 2H).

O-Tolylboronic Acid (Intermediate 65)

Following General Procedure A and using 2-bromotoluene (2 g, 7.8 mmol), 20 mL of anhydrous tetrahydrofuran, 1.7M solution of t-butyllithium in n-pentane (14 mL, 15.5 mmol) and trimethyl borate (2.6 mL, 15.5 mmol), the title compound was obtained after recrystallization from ethyl acetate-hexane mixture (0.8 g, 51%).

¹H NMR (300 MHz, CDCl₃): δ 8.19 (d, 1H,J=6.1 Hz), 7.45–7.40 (m, 1H), 7.30–7.21 (m, 2H), 2.80 (s, 3H).

5-[(1S,2S)-2-(3,3-Dimethyl-7-o-tolyl-2,3-dihydro-benzofuran-5-yl)-2-methyl-cyclopropyl]-3-methyl-penta-2E,4E-dienoic acid ethyl ester (Compound 25)

Following General Procedure B and using o-tolylboronic acid (Intermediate 65, 0.029 g, 0.21 mmol), (6S,7S)-7-[5-(7-bromo-3,3-dimethyl-2,3-dihydro-benzofuranyl)]-6,7-methano-3-methyl-octa-2E,4-dienoic acid ethyl ester (Compound 19, 0.09 g, 0.21 mmol), methanol (1 mL), toluene (5 mL), water (1 mL), potassium carbonate (0.059 g, 0.43 mmol) and tetrakis(triphenylphosphine)palladium(0) (20 mg), followed by flash column chromatography over silica gel (230–400 mesh), the title compound was obtained (0.096 g, 100%).

¹H NMR (300 MHz, CDCl₃): δ 7.24 (br s, 4H), 6.97 (d, 1H, J=1.7 Hz), 6.94 (d, 1H, J=1.7 Hz), 6.17 (d, 1H, J=15.6 Hz), 5.62 (s, 1H), 5.28 (dd, 1H, J=15.6 J=9.9 Hz), 4.21 (s, 2H), 4.14 (q, 2H, J=7.1 Hz), 2.21 (s, 3H), 2.01 (s, 3H), 1.76–1.69 (m, 1H), 1.44 (s, 3H), 1.36 (s, 3H), 1.32 (s, 3H), 1.27 (t, 3H, J=7.1 Hz), 1.19–1.15 (m, 2H).

5-[(1S,2S)-2-(3,3-Dimethyl-7-o-tolyl-2,3-dihydro-benzofuran-5-yl)-2-methyl-cyclopropyl]-3-methyl-penta-2E,4E-dienoic acid (Compound 26)

Following General Procedure H and using 5-[(1S, 2S)-2-(3,3-dimethyl-7-o-tolyl-2,3-dihydro-benzofuran-5-yl)-2-methyl-cyclopropyl]-3-methyl-penta-2E,4E-dienoic acid ethyl ester (Compound 25, 0.096 g, 0.22 mmol), ethanol (20 mL), and 5M aqueous sodium hydroxide (5 mL) followed by preparative reverse phase HPLC using 10% water in acetonitrile as the mobile phase, the title compound was obtained (0.044 g, 45%) as a white solid.

¹H NMR (300 MHz, CDCl₃): δ 7.27–7.22 (m, 4H), 6.97 (d, 1H, J=1.9 Hz), 6.94 (d, 1H, J=1.9 Hz), 6.20 (d, 1H, J=15.5 Hz), 5.64 (s, 1H), 5.33 (dd, 1H, J=15.6, 9.8 Hz), 4.21 (s, 2H), 2.02 (s, 3H), 2.00 (s, 3H), 1.77–1.68 (m, 1H), 1.44 (s, 3H), 1.37 (s, 3H), 1.32 (s, 3H), 1.20–1.15 (m, 2H).

1-(2-Bromo-phenyl)-heptan-1-ol (Intermediate 66)

Following General Procedure K and using 2-bromobenzaldehyde (1.5 g, 8 mmol), 15 mL of anhydrous tetrahydrofuran, and a 2M solution of n-hexyl magnesium bromide solution in ether (6 mL, 12 mmol) followed by flash column chromatography using 10% ethyl acetate in hexane, the title compound was obtained (1.86 g, 85%).

¹H NMR (300 MHz, CDCl₃): δ 7.52–7.46 (m, 2H), 7.32–7.24 (m, 1H), 7.11–7.06 (m, 1H), 5.05–5.00 (m, 1H), 2.49 (d, 1H, J=3.6 Hz), 1.78–1.55 (m, 2H), 1.45–1.23 (m, 8H), 0.88 (t, 3H, J=6.8 Hz).

1-Bromo-2-heptyl-benzene (Intermediate 67)

Following General Procedure J and using 1-(2-Bromo-phenyl)-heptan-1-ol (1.86 g, 6.9 mmol), anhydrous dichloromethane (5 mL), trifluoroacetic acid (2.5 mL, 32.5 mmol) and triethyl silane (5 mL, 31 mmol) followed by flash column chromatography, the title compound was obtained (0.4 g, 23%).

¹H NMR (300 MHz, CDCl₃): δ 7.49 (d, 1H, J=7.7 Hz), 7.19–7.15 (m, 2H), 7.02–6.96 (m, 1H), 2.70 (t, 2H, J=7.8 Hz), 1.64–1.55 (m, 2H), 1.40–1.27 (m, 8H), 0.88 (t, 3H, J=6.8 Hz).

2-Heptyl-phenylboronic Acid (Intermediate 68)

Following General Procedure A and using 1-bromo-2-heptyl-benzene (Intermediate 67, 0.4 g, 1.56 mmol), 4 mL of anhydrous tetrahydrofuran, 1.7M solution of t-butyllithium in n-pentane (1.84 mL, 3.1 mmol) and trimethyl borate (0.45 mL, 3.1 mmol), the title compound was obtained (0.27 g, 50%).

¹H NMR (300 MHz, CDCl₃): δ 8.21 (dd, 1H, J=7.5, 1.4 Hz), 7.48 (dd, 1H, J=7.5, 1.5 Hz), 7.33–7.25 (m, 2H), 3.19 (t, 2H, J=7.8 Hz), 1.30–1.22 (m, 10H), 0.85 (t, 3H, J=6.8 Hz).

(E)-3-((E)-2-{(1S,2S)-2-[7-(2-heptyl-phenyl)-3,3-dimethyl-2,3-dihydro-benzofuran-5-yl]-2-methyl-cyclopropyl}-vinyl)-but-2-enoic Acid, Ethyl Ester (Compound 27)

Following General Procedure B and using 2-heptyl-phenylboronic acid (Intermediate 68, 0.073 g, 0.33 mmol), (6S,7S)-7-[5-(7-bromo-3,3-dimethyl-2,3-dihydro-benzofuranyl)]-6,7-methano-3-methyl-octa-2E,4E-dienoic acid ethyl ester (Compound 19, 0.07 g, 0.167 mmol), methanol (2 mL), toluene (10 mL), water (2 mL), potassium carbonate (0.046 g, 0.33 mmol) and tetrakis(triphenylphosphine)palladium(0)(20 mg), followed by preparative normal phase HPLC using 4% ethyl acetate in hexane as the mobile phase, the title compound was obtained (0.038 g, 44%).

¹HNMR (300 MHz, CDCl₃): δ 7.27–7.22 (m, 4H), 6.96 (s, 1H), 6.94 (s, 1H), 6.19 (d, 1H, J=15.4 Hz), 5.63 (s, 1H), 5.28 (dd, 1H, J=15.3, 10.3 Hz), 4.19 (s, 2H), 4.14 (q, 3H, J=7.1 Hz), 2.51 (t, 2H, J=7.8 Hz), 2.02 (s, 3H), 1.76–1.69 (m, 1H), 1.44 (s, 3H), 1.36 (s, 3H), 1.31 (s, 3H), 1.27 (t, 3H, J=7.1 Hz),1.27–1.15 (m, 12H), 0.83 (t, 3H, J=6.6 Hz).

(E)-3-((E)-2-{(1S,2S)-2-[7-(2-Heptyl-phenyl-3,3-dimethyl-2.3-dihydro-benzofuran-5-yl]-2-methyl-cyclopropyl}-vinyl)-but-2-enoic Acid (Compound 28)

Following General Procedure H and using (E)-3-((E)-2-{(1S,2S)-2-[7-(2-heptyl-phenyl)-3,3-dimethyl-2,3-dihydro-benzofuran-5-yl]-2-methyl-cyclopropyl}-vinyl)-but-2-enoic acid, ethyl ester (Compound 27, 0.038 g, 0.074 mmol), ethanol (5 mL), and SM aqueous sodium hydroxide (2 mL) followed by preparative reverse phase HPLC using 10% water in acetonitrile as the mobile phase, the title compound was obtained (0.037 g, 97%).

¹H NMR (300 MHz, CDCl₃): δ 7.27–7.21 (m, 4H), 6.95 (d, 1H, J=2.0 Hz), 6.94 (d, 1H, J=2.0 Hz), 6.22 (d, 1H, J=15.5 Hz), 5.65 (s, 1H), 5.33 (dd, 1H, J=15.5, 9.9 Hz), 4.19 (s, 2H), 2.50 (t, 2H, J=7.8 Hz), 2.01 (s, 3H), 1.77–1.70 (m, 1H), 1.44 (s, 3H), 1.36 (s, 3H), 1.31 (s, 3H), 1.27–1.14 (m, 12H), 0.82 (t, 3H,J=6.9 Hz).

5-{(1S,2S)-2-[7-(4-tert-Butyl-phenyl)-3,3-dimethyl-2,3-dihydro-benzofuran-5-yl]-2-methyl-cyclopropyl}-3-methyl-pent-2E,4E-dienoic Acid Ethyl Ester (Compound 29)

Following General Procedure B and using 4-t-butyl-phenylboronic acid (Aldrich, 0.03 g, 0.187 mmol), (6S,7S)-7-[5-(7-bromo-3,3-dimethyl-2,3-dihydro-benzofuranyl)]-6,7-methano-3-methyl-octa-2E,4E-dienoic acid ethyl ester (Compound 19, 0.065 g, 0.155 mmol), methanol (1 mL), toluene (5 mL), water (1 mL), potassium carbonate (0.047 g, 0.34 mmol) and tetrakis(triphenylphosphine)palladium(0) (20 mg), the title compound was obtained (0.069 g, 95%).

¹H NMR (300 MHz, CDCl₃): δ 7.61 (dd, 2H, J=1.9, 8.5 Hz), 7.44 (dd, 2H, J=1.9, 8.5 Hz), 7.20 (d, 1H, J=1.8 Hz), 6.91 (d, 1H, J=1.8 Hz), 6.21 (d, 1H, J=15.5 Hz), 5.65 (s, 1H), 5.29 (dd, 1H, J=15.5, 9.9 Hz), 4.30 (d, 1H, J=8.4 Hz), 4.26 (d, 1H, J=8.4 Hz), 4.14 (q, 2H, J=7.1 Hz), 2.02 (s, 3H), 1.77–1.69 (m, 1H), 1.43 (s, 3H), 1.36 (s, 3H), 1.34 (s, 9H), 1.32 (s, 3H), 1.27 (t, 3H, J=7.1 Hz), 1.22–1.18 (m, 11H) 1.15–1.12 (m, 1H).

5-{(1S, 2S)-2-[7-(4-tert-Butyl-phenyl)-3,3-dimethyl-2,3-dihydro-benzofuran-5-]-2-methyl-cyclopropyl}-3-methyl-pent-2E,4E-dienoic Acid (Compound 30)

Following General Procedure H and using 5-{(1S, 2S)-2-[7-(4-tert-butyl-phenyl)-3,3-dimethyl-2,3-dihydro-benzofuran-5-yl]-2-methyl-cyclopropyl}-3-methyl-pent-2E,4E-dienoic acid ethyl ester (Compound 29, 0.069 g, 0.15 mmol), ethanol (10 mL), and 5M aqueous sodium hydroxide (2 mL) followed by preparative reverse phase HPLC using 10% water in acetonitrile as the mobile phase, the title compound was obtained (0.044 g, 48%).

¹H NMR (300 MHz, CDCl₃): δ 7.61 (dd, 2H, J=2.0, 8.5 Hz), 7.44 (dd, 2H, J=2.0, 8.5 Hz), 7.20 (d, 11H, J=1.8 Hz), 6.91 (d, 11H, J=1.8 Hz), 6.24 (d, 11H, J=15.5 Hz), 5.66 (s, 11H), 5.33 (dd, 11H, J=15.5, 10.0 Hz), 4.30 (d, 1H, J=8.5 Hz), 4.26 (d, 1H, J=8.5 Hz), 2.01 (s, 3H), 1.79–1.71 (m, 1H), 1.44 (s, 3H), 1.36 (s, 3H), 1.34 (s, 9H), 1.31 (s, 3H), 1.24–1.17 (m, 1H), 1.17–1.14 (m, 1H).

(E)-3-((E)-2-{(1S,2S)-2-[7-(4-Methoxy-phenyl)-3.3-dimethyl-2.3-dihydro-benzofuran-5-yl]-2-methyl-cyclopropyl}-vinyl)-but-2-enoic acid, ethyl ester (Compound 31)

Following General Procedure B and using 4-methoxy-phenylboronic acid (Aldrich, 0.024 g, 0.16 mmol), (6S,7S)-7-[5-(7-bromo-3,3-dimethyl-2,3-dihydro-benzofuranyl)]-6,7-methano-3-methyl-octa-2E,4E-dienoic acid ethyl ester (Compound 19, 0.055 g, 0.13 mmol), methanol (1 mL), toluene (7 mL), water (1 mL), potassium carbonate (0.043 g, 0.32 mmol) and tetrakis(triphenylphosphine)palladium(0) (25 mg), the title compound was obtained as a clear oil (0.041 g, 70%).

¹H NMR (300 MHz, CDCl₃): 7.64 (dd, 2H, J=2.0, 8.9 Hz), 7.18 (d, 1H, J=1.8 Hz), 6.96 (dd, 2H, J=2.0, 8.9 Hz), 6.89 (d, 1H, J=1.8 Hz), 6.22 (d, 1H, J=15.5 Hz), 5.65 (s, 1H), 5.35 (dd, 1H, J=15.5, 10.0 Hz), 4.29 (d, 1H, J=8.5 Hz), 4.25 (d, 1H, J=8.5 Hz), 4.14 (q, 2H, J=7.1 Hz), 3.84 (s, 3H), 2.02 (s, 3H), 1.77–1.69 (m, 1H), 1.45 (s, 3H), 1.37 (s, 3H), 1.32 (s, 3H), 1.28 (t, 3H,J=7.1 Hz), 1.25–1.21 (m, 11H), 1.17–1.14 (m, 1H).

(E)-3-((E)-2-{(1S,2S)-2-[7-(4-Methoxy-phenyl)-3,3-dimethyl-2,3-dihydro-benzofuran-5-yl]-2-methyl-cyclopropyl}-vinyl)-but-2-enoic acid (Compound 32)

Following General Procedure H and using (E)-3-((E)-2-{(1S, 2S)-2-[7-(4-methoxy-phenyl)-3,3-dimethyl-2,3-dihydro-benzofuran-5-yl]-2-methyl-cyclopropyl}-vinyl)-but-2-enoic acid ethyl ester (Compound 31, 0.041 g, 0.09 mmol), ethanol (5 mL), and 5M aqueous sodium hydroxide followed by preparative reverse phase HPLC using 10% water in acetonitrile as the mobile phase, the title compound was obtained (0.026 g, 65%).

¹H NMR (300 MHz, CDCl₃): 7.63 (dd, 2H, J=2.0, 8.7 Hz), 7.18 (d, 1H, J=1.7 Hz), 6.96 (dd, 2H, J=2.0, 8.7 Hz), 6.89 (d, 1H, J=1.8 Hz), 6.25 (d, 1H, J=15.5 Hz), 5.67 (s, 11H), 5.35 (dd, 11H, J=15.5, 10.0 Hz), 4.29 (d, 11H, J=8.5 Hz), 4.26 (d, 11H, J=8.5 Hz), 3.84 (s, 3H), 2.02 (s, 3H), 1.79–1.71 (m, 1H), 1.44 (s, 3H), 1.36 (s, 3H), 1.31 (s, 3H), 1.25–1.20 (m, 1H), 1.17–1.12 (m, 1H).

(E)-3-((E)-2-{(1S,2S)-2-[7-(4-Fluoro-phenyl)-3,3-dimethyl-2,3-dihydro-benzofuran-5-yl]-2-methyl-cyclopropyl}-vinyl)-but-2-enoic Acid Ethyl Ester (Compound 33)

Following General Procedure B and using 4-fluoro-phenylboronic acid (Aldrich, 0.020 g, 0.14 mmol), (6S, 7S)-7-[5-(7-bromo-3,3-dimethyl-2,3-dihydro-benzofuranyl)]-6,7-methano-3-methyl-octa-2E,4E-dienoic acid ethyl ester (Compound 19, 0.050 g, 0.12 mmol), methanol (1 mL), toluene (7 mL), water (1 mL), potassium carbonate (0.039 g, 0.29 mmol) and tetrakis(triphenylphosphine)palladium(0)(25 mg), the title compound was obtained (0.044 g, 85%).

$^1$H NMR (300 MHz, CDCl$_3$): 7.69–7.64 (m, 2H), 7.17 (d, 1H, J=1.7 Hz), 7.13–7.07 (m, 2H), 6.93 (d, 1H, J=1.7 Hz), 6.22 (d, 1H, J=15.5 Hz), 5.65 (s, 1H), 5.28 (dd, 1H, J=15.5, 10.0 Hz), 4.30 (d, 1H, J=8.5 Hz), 4.26 (d, 1H, J=8.5 Hz), 4.14 (q, 2H, J=7.1 Hz), 2.01 (s, 3H), 1.78–1.69 (m, 1H), 1.43 (s, 3H), 1.36 (s, 3H), 1.32 (s, 3H), 1.27 (t, 3H, J=7.1 Hz), 1.24–1.19 (m, 1H), 1.14–1.11 (m, 1H).

(E)-3-((E)-2-{(1S,2S)-2-[7-(4-Fluoro-phenyl)-3,3-dimethyl-2,3-dihydro-benzofuran-5-yl]-2-methyl-cyclopropyl}-vinyl)-but-2-enoic acid Compound 34)

Following General Procedure H and using (E)-3-((E)-2-{(1S,2S)-2-[7-(4-fluoro-phenyl)-3,3-dimethyl-2,3-dihydro-benzofuran-5-yl]-2-methyl-cyclopropyl}-vinyl)-but-2-enoic acid ethyl ester (Compound 33, 0.036 g, 0.083 mmol), methanol, and 5M aqueous sodium hydroxide (2 mL) followed by preparative reverse phase HPLC using 10% water in acetonitrile as the mobile phase, the title compound was obtained (0.016 g, 44%).

$^1$H NMR (300 MHz, CDCl$_3$): 7.69–7.64 (m, 2H), 7.17 (d, 1H, J=1.7 Hz), 7.13–7.08 (m, 2H), 6.93 (d, 1H, J=1.7 Hz), 6.25 (d, 1H, J=15.5 Hz), 5.68 (s, 1H), 5.33 (dd, 1H, J=15.5, 10.0 Hz), 4.28 (d, 2H), 2.01 (s, 3H), 1.78–1.72 (m, 1H), 1.44 (s, 3H), 1.37 (s, 3H), 1.31 (s, 3H), 1.26–1.21 (m, 1H), 1.17–1.14 (m, 1H).

3-iodo-prop-2 (Z)-ene-ol (Intermediate 69)

A stirred, cooled (−78° C.) solution of ethyl-cis-iodo acrylate (2.27 g, 10 mmol) in anhydrous dichloromethane (30 mL) was treated with a 1M solution of di-isobutylaluminumhydride in dichloromethane (22 mL, 22 mmol). The reaction mixture was allowed to warm to 0° C., quenched with methanol (1 mL) and saturated aqueous sodium-potassium tartarate solution (150 mL) and extracted with dichloromethane. The organic phase was dried over anhydrous magnesium sulfate, filtered and evaporated to afford the title compound as an oil (1.35 g, 73%).

$^1$H NMR (300 MHz, CDCl$_3$): δ 6.48–6.42 (m, 1H), 6.35–6.31 (m, 1H), 4.18 (s, 2H), 3.21 (s, 1H).

3,3-Dimethyl-5-(3-hydroxy-prop-(1Z)-enyl)-2,3-dihydro-benzofuran (Intermediate 70)

Following General Procedure B and using 3,3-dimethyl-2,3-dihydro-benzofuran-5-boronic acid (Intermediate 3, crude, 10 mmol), 3-iodo-prop-2 (Z)-ene-ol (Intermediate 69, 1.35 g, 7.29 mmol), methanol (20 mL), toluene (40 mL), water (10 mL), sodium carbonate (1.58 g, 15 mmol) and tetrakis(triphenylphosphine)palladium(0)(100 mg), followed by flash column chromatography over silica gel (230–400 mesh) using 15% ethyl acetate in hexane as the eluent the title compound was obtained (0.16 g, 8%).

$^1$H NMR (300 MHz, CDCl$_3$): δ 6.97 (d, 1H, J=8.0 Hz), 6.96 (s, 1H), 6.75 (d, 1H, J=8.0 Hz), 6.49 (d, 1H, J=11.7 Hz), 5.76–5.73 (m, 1H), 4.43 (d, 2H, J=6 Hz), 4.25 (s, 2H),1.34 (s, 6H).

3,3-Dimethyl-5-(3-hydroxy-1,2-methano-1-methyl-propyl)-2,3-dihydro-benzofuran (Intermediate 71)

Following General Procedure C and using 1.57M diethylzinc in anhydrous dichloromethane (10 mL, 15.7 mmol), 1,2-dimethoxyethane (1.63 mL, 15.7 mmol), diiodomethane (2.53 mL, 31.4 mmol), 3,3-dimethyl-5-(3-hydroxy-prop-(1Z)-enyl)-2,3-dihydro-benzofuran (Intermediate 70, 0.16 g, 0.78 mmol), 4A° molecular sieves powder (0.4 g) and (4R-trans)-2-butyl-N,N,N',N'-tetramethyl[1,3,2]dioxaborolane-[4,5]dicarboxamide (0.45 g, 1.56 mmol) in 3 mL of anhydrous dichloromethane followed by flash column chromatography using 20% ethyl acetate in hexane, the title compound was obtained as a brown oil (0.16 g, 94%).

$^1$H NMR (300 MHz, CDCl$_3$): δ 7.00 (d, 1H, J=8.0 Hz), 6.99 (s, 1H), 6.71 (d, 1H, J=8.0 Hz), 4.22 (s, 2H), 3.47 (dd, 1H, J=6.3, 11.5 Hz), 3.38 (dd, 1H, J=8.4, 11.5 Hz), 2.26–2.21 (m, 1H), 1.64 (br s, 1H), 1.47–1.35 (m, 1H), 1.33 (s, 6H), 1.05–0.98 (m, 1H), 0.88 (dd, 1H, J=5.5, 10.2 Hz).

(1S)-Camphanate ester of 3,3-dimethyl-5-[(1S,2S)-3-hydroxy-1,2-methano-propyl]-2,3-dihydro-benzofuran (Intermediate 72)

Following General Procedure D and using 3,3-dimethyl-5-[3-hydroxy-1,2-methano-propyl]-2,3-dihydro-benzofuran (Intermediate 71, 0.16 g, 0.73 mmol), anhydrous dichloromethane (5 mL), triethylamine (0.5 mL, 3.46 mmol) and (1S)-camphanic chloride (0.32 g, 1.48 mmol) followed by flash column chromatography using 17% ethyl acetate in hexane as the eluent. Recrystallization from hot hexane afforded the title compound (0.1 g, 34%). Preparative normal phase HPLC of the mother liquor (0.1 g) separated the major and minor isomer (0.038 g, 13%) formed during the cyclopropanation. Major isomer: $^1$H NMR (300 MHz, CDCl$_3$): δ 6.98–6.95 (m, 2H), 6.65 (d, 1H, J=7.9 Hz), 4.19 (s, 2H), 4.02 (dd, 1H, J=11.6, 7.2 Hz), 3.87 (dd, 1H, J=11.6, 8.1 Hz), 2.41–2.23 (m, 2H), 2.01–1.85 (m, 2H), 1.70–1.61 (m, 1H), 1.52–1.44 (m, 1H), 1.31 (s, 3H), 1.30 (s, 3H), 1.09 (s, 3H), 1.09–0.96 (m, 1H), 1.01 (s, 3H), 0.91–0.82 (m, 1H), 0.87 (s, 3H).

Minor isomer (title compound): $^1$H NMR (300 MHz, CDCl$_3$): δ 6.99 (d, 1H, J=8.7 Hz), 6.97 (s, 1H), 6.68 (d, 1H, J=8.0 Hz), 4.21 (s, 2H), 4.02 (dd, 1H, J=11.6, 7.2 Hz), 3.89 (dd, 1H, J=11.6, 8.1 Hz), 2.40–2.27 (m, 2H), 1.99–1.85 (m, 2H), 1.70–1.66 (m, 1H), 1.52–1.33 (m, 1H), 1.32 (s, 6H), 1.10 (s, 3H), 1.10–0.99 (m, 1H), 0.99 (s, 3H), 0.92 (s, 3H), 0.85 (dd, 1H, J=5.8, 11.7 Hz).

3,3-dimethyl-5-[(1S,2S)-3-hydroxy-1,2-methano-propyl]-2,3-dihydro-benzofuran (Intermediate 71a)

Following General Procedure E and using the (1S)-camphanate ester of 3,3-dimethyl-5-[(1S,2S)-3-hydroxy-1,2-methano-propyl]-2,3-dihydro-benzofuran (Intermediate 72, 0.038 g, 0.109 mmol), 1.5 mL of methanol, 1.5 mL of tetrahydrofuran, 0.5 mL of water and lithium hydroxide monohydrate (0.082 g, 1.95 mmol), the title compound was obtained (0.018 g, 76%) as a colorless, viscous oil.

$^1$H NMR (300 MHz, CDCl$_3$): δ 7.00 (d, 1H, J=8.0 Hz), 6.99 (s, 1H), 6.71 (d, 1H, J=8.0 Hz), 4.22 (s, 2H), 3.47 (dd, 1H, J=6.3, 11.5 Hz), 3.38 (dd, 1H, J=8.4, 11.5 Hz), 2.26–2.21 (m, 1H), 1.64 (br s, 1H), 1.47–1.35 (m, 1H), 1.33 (s, 6H), 1.05–0.98 (m, 1H), 0.88 (dd, 1H, J=5.5, 10.2 Hz).

3,3-Dimethyl-5-[(1S,2S)-1,2-methano-3-oxo-propyl]-2,3-dihydro-benzofuran (Intermediate 73)

Following General Procedure F and using 3,3-dimethyl-5-[(1S,2S)-3-hydroxy-1,2-methano-propyl]-2,3-dihydro-benzofuran (Intermediate 71a, 0.018 g, 0.083 mmol), dichloromethane (2.5 mL), acetonitrile (0.5 mL), 4A° molecular sieves powder (0.112 g), tetra-n-propylammoniumperruthenate (0.007 g) and N-methylmorpholine-N-oxide (0.08 g, 0.68 mmol) followed by flash column chromatography, the title compound was obtained (0.017 g, 95%) as a colorless oil.

$^1$H NMR (300 MHz, CDCl$_3$): δ 8.66 (d, 1H, J=5.6 Hz), 7.08–7.04 (m, 2H), 6.70 (d, 1H, J=7.8 Hz), 4.22 (s, 2H), 2.79–2.74 (m, 1H), 2.09–2.05 (m, 1H), 1.86–1.80 (m, 1H), 1.63–1.53 (m, 1H), 1.32 (s, 3H), 1.31 (s, 3H).

(E)-3-{(E)-2-[(1S,2S)-2-(3,3-Dimethyl-2,3-dihydro-benzofaran-5-yl)-cyclopropyl]-vinyl}-but-2-enoic Acid Ethyl Ester (Compound 35)

Following General Procedure G and using methyl-3-methyl-4-diethylphosphonocrotonate (1.01 g, 3.85 mmol), 4 mL of anhydrous tetrahydrofuran, 1.5 mL of 1,3-dimethyl-3,4,5,6-tetrahydro-2 (1H)-pyrimidinone (DMPU), 1.6M solution of n-butyllithium in hexanes (1.9 mL, 3 mmol), and 3,3-dimethyl-5-[(1S,2S)-1,2-methano-3-oxo-propyl]-2,3-dihydro-benzofuran (Intermediate 73, 0.017 g, 0.078 mmol) in tetrahydrofuran (1.5 mL), the title compound was obtained (0.015 g, 58% after HPLC).

$^1$H NMR (300 MHz, CDCl$_3$): δ 6.99–6.91 (m, 2H), 6.69 (d, 1H J=8.1 Hz), 6.22 (d, 1H, J=15.5 Hz), 5.62 (s, 1H), 5.39 (dd, 1H, J=15.5, 10.0 Hz), 4.22 (s, 2H), 4.14 (q, 2H, J=7.1 Hz), 2.44–2.01 (m, 1H), 2.01 (s, 3H), 1.91–1.87 (m, 1H), 1.50–1.20 (m, 1H), 1.32 (s, 3H), 1.30 (s, 3H), 1.26 (t, 3H,J=7.1 Hz), 1.08–1.02 (m, 1H).

(E)-3-{(E)-2-F[(1S,2S)-2-(3,3-Dimethyl-2,3-dihydro-benzofuran-5-yl)-cyclopropyl]-vinyl}-but-2-enoic acid (Compound 36)

Following General Procedure H and using (E)-3-{(E)-2-[(1S,2S)-2-(3,3-dimethyl-2,3-dihydro-benzofuran-5-yl)-cyclopropyl]-vinyl}-but-2-enoic acid ethyl ester (Compound 35, 0.015 g, 0.046 mmol), methanol (2 mL), tetrahydrofuran (2 mL) and 1M aqueous sodium hydroxide (1 mL) followed by preparative reverse phase HPLC using 10% water in acetonitrile as the eluent, the title compound was obtained (0.01 g, 80%) as a white solid.

$^1$H NMR (300 MHz, CDCl$_3$): δ 6.98 (dd, 1H, J=1.7, 8.1 Hz), 6.92 (d, 1H, J=1.7 Hz), 6.70 (d, 1H, J=8.1 Hz) 6.26 (d, 1H, J=15.6 Hz), 5.65 (s, 1H), 5.45 (dd, 1H, J=15.6, 10.0 Hz), 4.23 (s, 2H), 2.47–2.02 (m, 1H), 2.02 (s, 3H), 1.95–1.88 (m, 1H), 1.43–1.25 (m, 1H), 1.33 (s, 3H), 1.30 (s, 3H), 1.07 (dd, 1H, J=5.2, 11.7 Hz).

(E)-3-(5-Bromo-3,3-dimethyl-2,3-dihydro-benzofaran-7-yl)-acrylic acid ethyl ester (Intermediate 74)

A solution of 5-bromo-3,3-dimethyl-2,3-dihydro-benzofaran-7-carbaldehyde (Intermediate 30, 0.765 g, 3 mmol) in anhydrous toluene was treated with (ethoxycarbonylmethylidene)triphenylphosphorane (1.56 g, 4.5 mmol) (generated from (ethoxycarbonylmethyl) triphenylphosphonium bromide and aqueous sodium hydroxide) and heated at 100° C. for 1 h. The reaction mixture was cooled to room temperature and subjected to flash column chromatography using 8% ethyl acetate in hexane as the eluent to afford the title compound (0.97 g, 99%).

$^1$H NMR (300 MHz, CDCl$_3$): δ 7.52 (d, 1H J=16 Hz), 7.28 (d, 1H, J=2 Hz), 7.11 (d, 1H, J=2.0 Hz), 6.64 (d, 1H, J=16 Hz), 4.27 (s, 2H), 4.20 (q, 2H, J=7.1 Hz), 1.28 (s, 6H), 1.27 (t, 3H, J=7.1 Hz).

3-(3,3-Dimethyl-2,3-dihydro-benzofuran-7-yl)-propionic Acid Ethyl Ester (Intermediate 75)

A solution of (E)-3-(5-bromo-3,3-dimethyl-2,3-dihydro-benzofuran-7-yl)-acrylic acid ethyl ester (Intermediate 74, 0.97 g, 2.98 mmol) in 13 mL of ethyl acetate was treated with a slurry of 10% palladium on carbon (0.25 g) in 7 mL of ethanol and the resulting reaction mixture was stirred overnight under an atmosphere of hydrogen. The solids were then filtered over a bed of celite and the filtrate was evaporated to an oil. The oil was dissolved in dichloromethane and washed with water. The organic phase was dried over anhydrous sodium sulfate, filtered and evaporated to afford the title compound as a pale yellow oil (0.71 g, 96%).

$^1$H NMR (300 MHz, CDCl$_3$): δ 6.98 (d, 2H J=7.2 Hz), 6.82 (dd, 1H, J=7.2, 7.6 Hz), 4.23 (s, 2H), 4.14 (q, 2H, J=7.1 Hz), 2.93 (t, 2H, J=7.8 Hz), 2.65 (t, 2H, J=7.8 Hz), 1.34 (s, 6H), 1.25 (t, 3H, J=7.1 Hz).

3-(5-Bromo-3,3-dimethyl-2,3-dihydro-benzofuran-7-yl)-propionic Acid Ethyl Ester (Intermediate 76)

A stirred, cooled (ice bath) solution of 3-(3,3-dimethyl-2,3-dihydro-benzofuran-7-yl)-propionic acid ethyl ester (Intermediate 75, 0.71 g, 2.86 mmol) in ethanol (14 mL) was treated with bromine (0.3 mL, 5.819 mmol) and the reaction mixture was allowed to gradually warm up to room temperature over 1.5 h. The volatiles were then evaporated in vacuo and the residue was dissolved in diethyl ether and washed with water (×1), aqueous sodium thiosulfate solution (×1) and brine (×1), dried over anhydrous sodium sulfate, filtered and evaporated to afford the title compound as an oil (0.875 g, 93%).

$^1$H NMR (300 MHz, CDCl$_3$): δ 7.08 (d, 1H J=2 Hz), 7.05 (d, 1H, J=2 Hz), 4.22 (s, 2H), 4.12 (q, 2H, J=7.1 Hz), 2.85 (t, 2H, J=7.8 Hz), 2.60 (t, 2H, J=7.8 Hz), 1.31 (s, 6H), 1.23 (t, 3H, J=7.1 Hz).

3-(5-Bromo-3,3-dimethyl-2,3-dihydro-benzofuran-7-yl)-propionic Acid (Intermediate 77)

A solution of 3-(5-bromo-3,3-dihydro-benzofuran-7-yl)-propionic acid ethyl ester (Intermediate 76, 0.875 g, 2.67 mmol) in methanol (15 mL), tetrahydrofuran (15 mL) and water (7 mL) was treated with lithium hydroxide monohydrate (0.68 g, 16 mmol) and the resulting reaction mixture was stirred at room temperature for 1 h. The volatiles were evaporated in vacuo and the residue was diluted with water and washed with diethyl ether. The aqueous phase was neutralized with concentrated hydrochloric acid and the solution was extracted with ether (×3). The combined organic phase was dried over anhydrous magnesium sulfate, filtered and evaporated to afford the title compound as an oily foam (0.64 g, 87%).

$^1$H NMR (300 MHz, CDCl$_3$): δ 7.10 (d, 1H J=2 Hz), 7.07 (d, 1H, J=2 Hz), 4.23 (s, 2H), 2.87 (t, 2H, J=7.5 Hz), 2.69 (t, 2H, J=7.5 Hz), 1.32 (s, 6H).

3-(5-Bromo-3,3-dimethyl-2,3-dihydro-benzofuran-7-yl)-N,N-dimethyl-propionamide (Intermediate 78)

A stirred, cooled (−78° C.) solution of 3-(5-bromo-3,3-dimethyl-2,3-dihydro-benzofuran-7-yl)-propionic acid (Intermediate 77, 0.7 g, 2.34 mmol) and triphenyl phosphine (0.74 g, 2.81 mmol) in anhydrous benzene (10 mL) and dichloromethane (20 mL) was treated with hexachloroacetone (0.178 mL, 1.17 mmol). After 1 h, a 2M solution of dimethyl amine in tetrahydrofuran (3 mL, 6 mmol) was added. After 1 h, the reaction mixture was evaporated in vacuo to a brown oil which was subjected to flash column chromatography using 40% ethyl acetate in hexane as the eluent to afford the title compound (0.65 g, 84%).

$^1$H NMR (300 MHz, CDCl$_3$): δ 7.03 (d, 1H J=2 Hz), 6.96 (d, 1H, J=2 Hz), 4.14 (s, 2H), 2.89 (s, 3H), 2.86 (s, 3H), 2.79 (t, 2H,J=7.8 Hz), 2.52 (t, 2H,J=7.8 Hz), 1.23 (s, 6H).

3,3-Dimethyl-7-(3-oxo-heptyl)-2,3-dihydro-benzofaran-5-boronic Acid (Intermediate 79)

Following General Procedure A and using 3-(5-bromo-3,3-dimethyl-2,3-dihydro-benzofuran-7-yl)-N,N-dimethyl-propionamide (Intermediate 78, 0.64 g, 2 mmol), 10 mL of anhydrous tetrahydrofuran, 1.7M solution of n-butyllithium in hexanes (2.5 mL, 4 mmol) and trimethyl borate (0.45 mL, 4 mmol) the title compound was obtained as a foam that was used as such for the next step without purification and characterization.

1-[5-((Z)-3-Hydroxy-1-methyl-propenyl)-3,3-dimethyl-2,3-dihydro-benzofuran-7-yl]-heptan-3-one (Intermediate 80)

Following General Procedure B and using 3,3-dimethyl-7-(3-oxo-heptyl)-2,3-dihydro-benzofuran-5-boronic acid (Intermediate 79, crude, obtained from the previous step, 2 mmol), 3-iodo-but-2 (Z)-ene-ol (0.4 g, 1.98 mmol), methanol (6 mL), toluene (6 mL), water (2 mL), sodium carbonate (0.42 g, 4 mmol) and tetrakis(triphenylphosphine)palladium (0)(30 mg), followed by flash column chromatography over silica gel (230–400 mesh) using 15–25% ethyl acetate in hexane as the eluent the title compound was obtained (0.18 g, 28% over two steps).

$^1$H NMR (300 MHz, CDCl$_3$): δ 6.76 (s, 2H), 5.62 (dt, 1H, J=1.4, 7.0 Hz), 4.22 (s, 2H), 4.06 (d, 2H, J=6.6 Hz), 2.85–2.70 (m, 4H), 2.38 (t, 2H, J=7.3 Hz), 2.04 (s, 3H), 2.02 (br s, 1H), 1.52 (quintet, 2H, J=7.4 Hz), 1.31 (s, 6H), 1.31–1.20 (m, 2H), 0.86 (t, 3H, J=7.3 Hz).

1-[5-(1S 2S)-(2-Hydroxymethyl-1-methyl-cyclopropyl)-3, 3-dimethyl-2,3-dihydro-benzofuran-7-yl]-heptan-3-one (Intermediate 81)

Following General Procedure C and using 1.57M diethylzinc in anhydrous dichloromethane (10 mL, 15.7 mmol), 1,2-dimethoxyethane (1.63 mL, 15.7 mmol), diiodomethane (2.53 mL, 31.4 mmol), 1-[5-((Z)-3-hydroxy-1-methyl-propenyl)-3,3-dimethyl-2,3-dihydro-benzofuran-7-yl]-heptan-3-one (Intermediate 800.18 g, 0.55 mmol), 4A° molecular sieves powder (0.4 g) and (4S-trans)-2-butyl-N, N,N',N'-tetramethyl[1,3,2]dioxaborolane-[4,5] dicarboxamide (0.34 g, 1.17 mmol) in 3 mL of anhydrous dichloromethane followed by flash column chromatography using 20% ethyl acetate in hexane, the title compound was obtained as a brown oil (0.16 g,85%). It was used as such for the next step.

(1S)-Camphanate ester of 1-[5-((1S,2S)-2-Hydroxymethyl-1methyl-cyclopropyl)-3,3-dimethyl-2,3-dihydro-benzofaran-7-yl]-heptan-3-one (Intermediate 82)

Following General Procedure D and using 1-[5-(2-hydroxymethyl-1-methyl-cyclopropyl)-3,3-dimethyl-2,3-dihydro-benzofuran-7-yl]-heptan-3-one (Intermediate 81, 0.16 g, 0.47 mmol), anhydrous dichloromethane (3 mL), triethylamine (0.5 mL, 3.46 mmol) and (1S)-camphanic chloride (0.24 g, 1.11 mmol) followed by flash column chromatography using 20% ethyl acetate in hexane as the eluent, the title compound was obtained as a viscous oil. Preparative normal phase HPLC using 15% ethyl acetate in hexane as the mobile phase eliminated the minor isomer formed during the cyclopropanation step (0.1 g, 41%).

$^1$H NMR (300 MHz, CDCl$_3$): δ 6.87 (s, 1H), 6.86 (s, 1H), 4.18 (s, 2H), 3.90–3.75 (m, 2H), 2.82–2.68 (m, 4H), 2.43–2.34 (m, 3H), 2.01–1.80 (m, 2H), 1.71–1.62 (m, 1H), 1.52 (quintet, 2H, J=7.5 Hz), 1.32–1.20 (m, 3H), 1.32 (s, 3H), 1.30 (s, 3H), 1.29 (s, 3H), 1.10 (s, 3H), 1.03 (s, 3H), 0.97 (s, 3H), 0.95–0.80 (m, 5H).

7-[3-(tert-Butyl-dimethyl-silanyloxy)-heptyl]-3,3-dimethyl-5-[(1S,2S)-3-hydroxy-1,2-methano-1-methyl-propyl]-2,3-dihydro-benzofuran (Intermediate 83)

A solution of the (1S)-camphanate ester of 1-[5-((1S, 2S)-2-hydroxymethyl-1-methyl-cyclopropyl)-3,3-dimethyl-2,3-dihydro-benzofuran-7-yl]-heptan-3-one (Intermediate 82, 0.1 g, 0.19 mmol) in ethanol (2 mL) and dichloromethane (2 mL) was treated with sodium borohydride (0.12 g, 3.17 mmol). After 15 minutes, the volatiles were evaporated in vacuo and the residue was diluted with water and extracted with diethyl ether (×2). The combined organic extract was dried over anhydrous magnesium sulfate, filtered and evaporated in vacuo to afford the corresponding alcohol (0.09 g, 89%).

A stirred, cooled (ice bath) solution of the alcohol obtained as above (0.09 g, 0.17 mmol) in dichloromethane (2 mL) was treated with imidazole (0.080 g, 1.17 mmol) followed by tert-butyldimethylchlorosilane (0.08 g, 0.53 mmol). The reaction mixture was allowed to warm to room temperature and stirred for 2 h. The reaction mixture was then subjected to flash column chromatography using 10% ethyl acetate in hexane as the eluent to afford the corresponding silyl protected compound as a clear, colorless oil (0.1 g, 91%).

Following General Procedure E and using the silyl protected compound obtained as above (0.1 g, 0.15 mmol), 2 mL of methanol, 2 mL of tetrahydrofuran, 0.75 mL of water and lithium hydroxide monohydrate (0.16 g, 3.81 mmol), the title compound was obtained. (0.05 g, 68%).

$^1$H NMR (300 MHz, CDCl$_3$): δ 6.89 (s, 2H), 4.21 (s, 2H), 3.69 (m, 1H), 3.25 (d, 2H, J=6.7 Hz), 2.65–2.48 (m, 2H), 1.78–1.71 (m, 2H), 1.49–1.47 (m, 2H), 1.38 (s, 3H), 1.32 (s, 3H), 1.31 (s, 3H), 1.31–1.23 (m, 5H), 0.91 (s, 9H), 0.91–0.90 (m, 3H), 0.86–0.74 (m, 2H), 0.05 (s, 3H), 0.04 (s, 3H).

7-[3-(tert-Butyl-dimethyl-silanyloxy)-heptyl]-3,3-dimethyl-5-F(1S,2S)-3-hydroxy-1,2-methano-1-methyl-3-oxo-propyl]-2,3-dihydro-benzofuran (Intermediate 84)

Following General Procedure F and using 7-[3-(tert-butyl-dimethyl-silanyloxy)-heptyl]-3,3-dimethyl-5-[(1S, 2S)-3-hydroxy-1,2-methano-1-methyl-propyl]-2,3-dihydro-benzofuran (Intermediate 83, 0.05 g, 0.111 mmol), dichloromethane (2.5 mL), acetonitrile (0.5 mL), 4A° molecular sieves powder (0.3 g), tetra-n-propylammoniumperruthenate (0.016 g) and N-methylmorpholine-N-oxide (0.145 g, 1.23 mmol) followed by flash column chromatography, the title compound was obtained (0.05 g, 100%) as a colorless oil.

$^1$H NMR (300 MHz, CDCl$_3$): δ 8.41 (d, 1H, J=6 Hz), 6.91 (d, 1H, J=1.8 Hz), 6.88 (d, 1H, J=1.8 Hz), 4.21 (s, 2H), 3.68 (m, 1H), 2.65–2.48 (m, 2H), 1.89–1.83 (m, 2H), 1.75–1.70 (m, 3H), 1.44 (s, 3H), 1.32 (s, 3H), 1.29 (s, 3H), 1.50–1.25 (m, 6H), 0.97 (s, 9H), 0.97–0.85 (m, 3H), 0.05 (s, 3H), 0.03 (s, 3H).

(E)-3-((E)-2-{(1S,2S)-2-[7-(3-Hydroxy-heptyl)-3,3-dimethyl-2,3-dihydro-benzofuran-5-yl]-2-methyl-cyclopropyl}-vinyl)-but-2-enoic Acid Ethyl Ester (Compound 37)

Following General Procedure G and using methyl-3-methyl-4-diethylphosphonocrotonate (1.01 g, 3.85 mmol), 4 mL of anhydrous tetrahydrofuran, 1.5 mL of 1,3-dimethyl-3,4,5,6-tetrahydro-2 (1H)-pyrimidinone (DMPU), 1.6M solution of n-butyllithium in hexanes (1.9 mL, 3 mmol), and 7-[3-(tert-butyl-dimethyl-silanyloxy)-heptyl]-3,3-dimethyl-5-[(1S,2S)-3-hydroxy-1,2-methano-1-methyl-3-oxo-propyl]-2,3-dihydro-benzofuran (Intermediate 84, 0.015 g, 0.11 mmol) in tetrahydrofuran (1.5 mL), the corresponding silyl ether of title compound was obtained after flash column chromatography over silica gel (230–400 mesh) using 5% ethyl acetate in hexane as the eluent (0.05 g, 81%). A stirred solution of the silyl ether obtained as above (0.05 g, 0.087 mmol) in 3 mL of ethanol was treated with aqueous 1N hydrochloric acid (1 mL, 1 mmol). After 1.5 h, the volatiles were evaporated in vacuo, the residue was diluted with water and extracted with diethyl ether (×2). The combined organic extract was dried over anhydrous magnesium sulfate, filtered and evaporated in vacuo to afford an oil. Flash column chromatography over silica gel (230–400 mesh) using 10–15% ethyl acetate in hexane as the eluent afforded the title product (0.029 g, 71%).

$^1$H NMR (300 MHz, CDCl$_3$): δ 6.86 (s, 1H), 6.81 (s, 1H), 6.18 (d, 1H, J=15.5 Hz), 5.63 (s, 1H), 5.22 (dd, 1H, J=10, 15.5 Hz), 4.22 (s, 2H), 4.14 (q, 2H, J=7.1 Hz), 3.50 (m, 1H), 2.80–2.58 (m, 2H), 1.99 (s, 3H), 1.72–1.66 (m, 5H), 1.39 (s, 3H), 1.32 (s, 3H), 1.27 (s, 3H), 1.50–1.08 (m, 6H), 1.27 (t, 3H, J=7.1 Hz), 0.89 (t, 3H, J=6.6 Hz).

(E)-3-((E)-2-{(1S,2S)-2-[7-(3-Hydroxy-heptyl)-3,3-dimethyl-2,3-dihydro-benzofuran-5-yl]-2-methyl-cyclopropyl}-vinyl)-but-2-enoic acid (Compound 38)

Following General Procedure H and using (E)-3-((E)-2-{(1S,2S)-2-[7-(3-hydroxy-heptyl)-3,3-dimethyl-2,3-dihydro-benzofuran-5-yl]-2-methyl-cyclopropyl}-vinyl)-but-2-enoic acid ethyl ester (Compound 37, 0.007 g, 0.015 mmol), methanol (1.5 mL), tetrahydrofuran (1.5 mL) and 1M aqueous sodium hydroxide (0.5 mL) followed by preparative reverse phase HPLC using 10% water in acetonitrile as the eluent, the title compound was obtained (0.0044 g, 67%).

$^1$H NMR (300 MHz, CDCl$_3$): δ 6.86 (s, 1H), 6.81 (s, 1H), 6.20 (d, 1H, J=15.5 Hz), 5.65 (s, 1H), 5.27 (dd, 1H, J=10, 15.5 Hz), 4.22 (s, 2H), 3.51 (m, 1H), 2.80–2.50 (m, 2H), 1.99 (s, 3H), 1.72–1.66 (m, 5H), 1.40 (s, 3H), 1.33 (s, 3H), 1.27 (s, 3H), 1.50–1.10 (m, 6H), 0.89 (t, 3H, J=7.1 Hz).

(E)-3-((E)-2-{(1 S,2S)-2-[3,3-Dimethyl-7-(3-oxo-heptyl)-2,3-dihydro-benzofuran-5-yl]-2-methyl-cyclopropyl}-vinyl)-but-2-enoic acid ethyl ester (Compound 39)

Following General Procedure F and using (E)-3-((E)-2-{(1S,2S)-2-[7-(3-hydroxy-heptyl)-3,3-dimethyl-2,3-dihydro-benzofuran-5-yl]-2-methyl-cyclopropyl}-vinyl)-but-2-enoic acid ethyl ester (Compound 38, 0.019 g, 0.042 mmol), dichloromethane (2.5 mL), acetonitrile (0.5 mL), 4A° molecular sieves powder (0.15 g), tetra-n-propylammoniumperruthenate (0.012 g) and N-methylmorpholine-N-oxide (0.07 g, 0.6 mmol), the title compound was obtained (0.012 g, 58%).

$^1$H NMR (300 MHz, CDCl$_3$): δ 6.84 (d, 1H, J=1.8 Hz), 6.80 (d, 1H, J=1.8 Hz), 6.18 (d, 1H, J=15.5 Hz), 5.63 (s, 11H), 5.21 (dd, 1H, J=9.9, 15.5 Hz), 4.21 (s, 2H), 4.14 (q, 2H, J=7.1 Hz), 2.85–2.68 (m, 4H), 2.39 (t, 2H, J=7.3 Hz), 2.00 (s, 3H), 1.71–1.60 (m, 1H), 1.60–1.49 (m, 2H), 1.38 (s, 3H), 1.32 (s, 3H), 1.27 (t, 3H, J=7.1 Hz), 1.26 (s, 3H), 1.40–1.20 (m, 2H), 1.16 (dd, 1H, J=4.7, 8.1 Hz), 1.07 (t, 1H, J=4.8 Hz), 0.89 (t, 3H, J=6.6 Hz).

(E)-3-((E)-2-{(1S,2S)-2-r[33-Dimethyl-7-(3-oxo-heptyl-2,3-dihydro-benzofuran-5-yl]-2-methyl-cyclopropyl}-vinyl)-but-2-enoic acid (Compound 40)

Following General Procedure H and using (E)-3-((E)-2-{(1S,2S)-2-[3,3-dimethyl-7-(3-oxo-heptyl)-2,3-dihydro-benzofuran-5-yl]-2-methyl-cyclopropyl}-vinyl)-but-2-enoic acid ethyl ester (Compound 39, 0.012 g, 0.032 mmol), methanol (2 mL), tetrahydrofuran (2 mL) and 1M aqueous sodium hydroxide (1 mL) followed by preparative reverse phase HPLC using 10% water in acetonitrile as the eluent, the title compound was obtained (0.0096 g, 85%).

$^1$H NMR (300 MHz, CDCl$_3$): δ 6.85 (s, 1H), 6.80 (s, 1H), 6.21 (d, 1H, J=15.4 Hz), 5.65 (s, 1H), 5.27 (dd, 1H, J=9.9, 15.4 Hz), 4.21 (s, 2H), 2.85–2.68 (m, 4H), 2.39 (t, 2H, J=7.3 Hz), 2.00 (s, 3H), 1.72–1.66 (m, 1H), 1.54 (m, 2H), 1.39–1.28 (m, 2H), 1.39 (s, 3H), 1.32 (s, 3H), 1.26 (s, 3H), 1.20–1.07 (m, 2H), 0.88 (t, 3H, J-6.6 Hz).

What is claimed is:

1. A compound of the formula

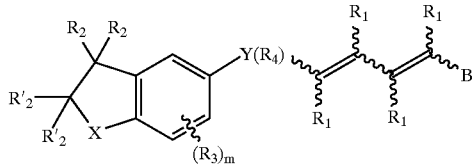

where X is O or S;

Y is a bivalent cycloalkyl or cycloalkenyl radical optionally substituted with one to four $R_4$ groups, the cycloalkenyl radical having 5 or 6 carbons and one double bond, or Y is a bivalent aryl or 5 or 6 membered heteroaryl radical having 1 to 3 heteroatoms selected from N, S and O, said aryl or heteroaryl groups optionally substituted with 1 to 4 $R_4$ groups with the proviso that the cycloalkyl or the cycloalkenyl radical is not substituted on the same carbon with the condensed cyclic moiety and with the diene containing moiety;

$R_1$ is independently H, alkyl of 1 to 6 carbons, or fluoroalkyl of 1 to 6 carbons;

$R_2$ is independently H, alkyl of 1 to 8 carbons, or fluoroalkyl of 1 to 8 carbons;

$R'_2$ is independently H, alkyl of 1 to 8 carbons, or fluoroalkyl of 1 to 8 carbons;

$R_3$ is hydrogen, alkyl of 1 to 10 carbons, fluoro substituted alkyl of 1 to 10 carbons, halogen, alkoxy of 1 to 10 carbons, or alkylthio of 1 to 10 carbons; $NO_2$, $NH_2$, $NHCO(C_1-C_6$ alkyl), $NHCO(C_1-C_6)$alkenyl, $NR_1H$ or $N(R_1)_2$, benzyloxy, $C_1-C_6$alkyl-substituted benzyloxy, or $R_3$ is selected from the groups shown below,

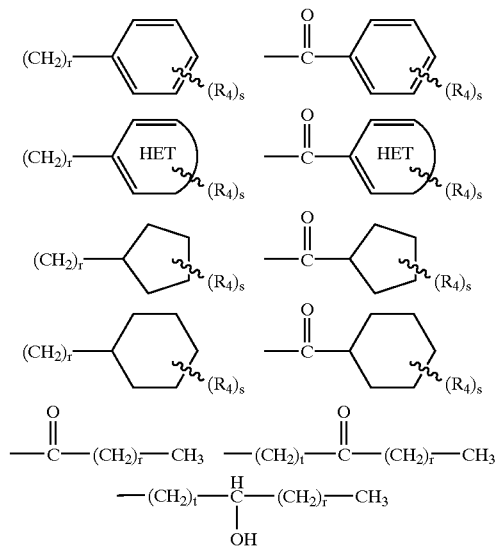

$R_4$ is H, halogen, alkyl of 1 to 10 carbons, fluoro substituted alkyl of 1 to 6 carbons, alkoxy of 1 to 10 carbons, or alkylthio of 1 to 10 carbons;

m is an integer having the values of 0 to 3;
r is an integer having the values of 1 to 10;
s is an integer having the values 1 to 4;
t is an integer having the values 1 to 5;

represents a 5 or 6 membered heteroaryl ring having 1 to 3 heteroatoms selected from the group consisting of N, S and O;

B is COOH or a pharmaceutically acceptable salt thereof, $COOR_8$, $COOCH_2COR_7$, $CONR_9R_{10}$, —$CH_2OH$, $CH_2OR_{11}$, $CH_2OCOR_{11}$, CHO, $CH(OR_{12})_2$, $CH(OR_{13}O)$, —$COR_7$, $CR_7(OR_{12})_2$, $CR_7(OR_{13}O)$, where $R_7$ is an alkyl, cycloalkyl or alkenyl group containing 1 to 5 carbons, $R_8$ is an alkyl group of 1 to 10 carbons or (trimethylsilyl)alkyl where the alkyl group has 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl, hydroxyphenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

2. A compound in accordance with claim 1 wherein X is O.

3. A compound in accordance with claim 1 where X is S.

4. A compound in accordance with claim 1 where V is a bivalent cyclopropyl radical.

5. A compound in accordance with claim 1 where is a bivalent phenyl radical.

6. A compound in accordance with claim 1 where Y is a bivalent pyridine radical.

7. A compound in accordance with claim 1 where Y is a bivalent furan or thiophene radical.

8. A compound in accordance with claim 1 where B is COOH or a pharmaceutically acceptable salt thereof, or $COOR_8$.

9. A compound in accordance with claim 1 where $R_3$ is alkyl of 1 to 10 carbons.

10. A compound in accordance with claim 1 where $R_3$ is halogen.

11. A compound in accordance with claim 1 where $R_3$ is phenyl, phenyl substituted with halogen, phenyl substituted with an alkoxy group of 1 to 10 carbons, phenyl substituted with one or two alkyl groups of 1 to 10 carbons, phenylmethyl, or phenylmethyl substituted with one or two alkyl groups of 1 to 10 carbons.

12. A compound in accordance with claim 1 where $R_3$ is CO—$(CH_2)_r$—$CH_3$, $(CH_2)_r$—CO—$(CH_2)_r$—$CH_3$, $(CH_2)_r$—CHOH—$(CH_2)_r$—$CH_3$ or cyclohexylmethyl.

13. A compound of the formula

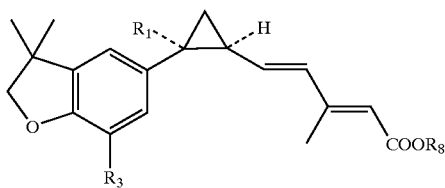

wherein $R_1$ is H or methyl;

$R_8$ is H, alkyl of 1 to 6 carbons, or a pharmaceutically acceptable cation, and $R_3$ is hydrogen, alkyl of 1 to 10 carbons, halogen, alkoxy of 1 to 10 carbons, or $R_3$ is selected from the groups shown below

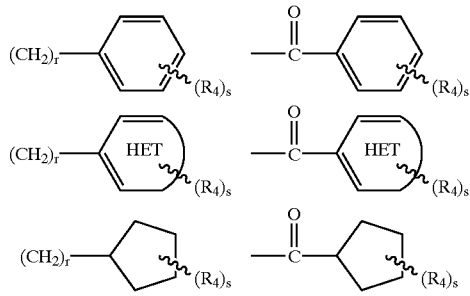

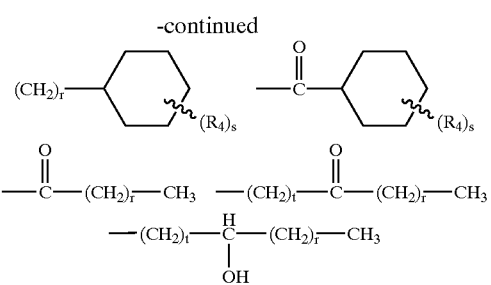

where $R_4$ is H, halogen, alkyl of 1 to 10 carbons, carbons, alkoxy of 1 to 10;

r is an integer having the values of 1 to 10;

s is an integer having the values 1 to 4;

represents a 5 or 6 membered heteroaryl ring having 1 to 3 heteroatoms selected from the group consisting of N, S and O, and t is an integer having the values 1 to 5.

14. A compound in accordance with claim 13 where $R_3$ is H.

15. A compound in accordance with claim 14 where $R_8$ is H, a pharmaceutically acceptable cation or ethyl, and where $R_1$ is methyl.

16. A compound in accordance with claim 13 where $R_3$ is $CH_3$.

17. A compound in accordance with claim 16 where $R_8$ is H, a pharmaceutically acceptable cation or ethyl, and where $R_1$ is methyl.

18. A compound in accordance with claim 13 where $R_3$ is $CH_2CH_3$.

19. A compound in accordance with claim 18 where $R_8$ is H, a pharmaceutically acceptable cation or ethyl, and where $R_1$ is methyl.

20. A compound in accordance with claim 13 where $R_3$ is iso-propyl.

21. A compound in accordance with claim 20 where $R_8$ is H, a pharmaceutically acceptable cation or ethyl, and where $R_1$ is methyl.

22. A compound in accordance with claim 13 where $R_3$ is tertiary-butyl.

23. A compound in accordance with claim 22 where $R_8$ is H, a pharmaceutically acceptable cation or ethyl, and where $R_1$ is methyl.

24. A compound in accordance with claim 13 where $R_3$ is phenyl.

25. A compound in accordance with claim 24 where $R_8$ is H, a pharmaceutically acceptable cation or ethyl, and where $R_1$ is methyl.

26. A compound in accordance with claim 13 where $R_3$ is tertiary-butylmethyl.

27. A compound in accordance with claim 26 where $R_8$ is H, a pharmaceutically acceptable cation or ethyl, and where $R_1$ is methyl.

28. A compound in accordance with claim 13 where $R_3$ is phenylmethyl.

29. A compound in accordance with claim 28 where $R_8$ is H, a pharmaceutically acceptable cation or ethyl, and where $R_1$ is methyl.

30. A compound in accordance with claim 13 where $R_3$ is n-hexyl.

31. A compound in accordance with claim 30 where $R_8$ is H, a pharmaceutically acceptable cation or ethyl, and where $R_1$ is methyl.

32. A compound in accordance with claim 13 where $R_3$ is Br.

33. A compound in accordance with claim 32 where $R_8$ is H, a pharmaceutically acceptable cation or ethyl, and where R1 is methyl.

34. A compound in accordance with claim 13 where $R_3$ is 2-methylphenyl.

35. A compound in accordance with claim 34 where $R_8$ is H, a pharmaceutically acceptable cation or ethyl, and where $R_1$ is methyl.

36. A compound in accordance with claim 13 where $R_3$ is 2,6-dimethylphenyl.

37. A compound in accordance with claim 36 where $R_8$ is H, a pharmaceutically acceptable cation or ethyl, and where $R_1$ is methyl.

38. A compound in accordance with claim 13 where $R_3$ is 4-tertiary-butylphenyl.

39. A compound in accordance with claim 38 where $R_8$ is H, a pharmaceutically acceptable cation or ethyl, and where $R_1$ is methyl.

40. A compound in accordance with claim 13 where $R_3$ is 2-n-heptyiphenyl.

41. A compound in accordance with claim 40 where $R_8$ is H, a pharmaceutically acceptable cation or ethyl, and where $R_1$ is methyl.

42. A compound in accordance with claim 13 where $R_3$ is H.

43. A compound in accordance with claim 42 where $R_8$ is H, a pharmaceutically acceptable cation or ethyl, and where $R_1$ is H.

44. A compound in accordance with claim 13 where $R_3$ is $CH_2CH_2CO(CH_2)_3 CH_3$.

45. A compound in accordance with claim 44 where $R_8$ is H, a pharmaceutically acceptable cation or ethyl, and where $R_1$ is methyl.

46. A compound in accordance with claim 13 where $R_3$ is $CH_2CH_2CHOH(CH_2)_3 CH_3$.

47. A compound in accordance with claim 46 where $R_8$ is H, a pharmaceutically acceptable cation or ethyl, and where $R_1$ is methyl.

48. A compound in accordance with claim 13 where $R_3$ is $CH_2$-cyclohexyl.

49. A compound in accordance with claim 48 where $R_8$ is H, a pharmaceutically acceptable cation or ethyl, and where $R_1$ is methyl.

50. A compound in accordance with claim 13 where $R_3$ is 4-fluorophenyl.

51. A compound in accordance with claim 50 where $R_8$ is H, a pharmaceutically acceptable cation or ethyl, and where $R_1$ is methyl.

52. A compound in accordance with claim 13 where $R_3$ is 4-methoxyphenyl.

53. A compound in accordance with claim 52 where $R_8$ is H, a pharmaceutically acceptable cation or ethyl, and where $R_1$ is methyl.

54. A compound of the formula

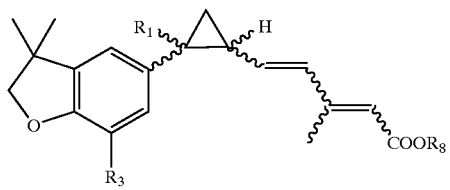

wherein $R_1$ is H or methyl;

$R_8$ is H, alkyl of 1 to 6 carbons, or a pharmaceutically acceptable cation, and $R_3$ is hydrogen, alkyl of 1 to 10 carbons, halogen, alkoxy of 1 to 10 carbons, or $R_3$ is selected from the groups shown below

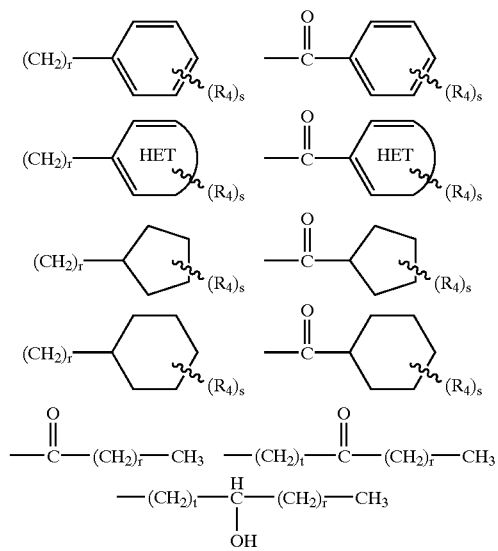

where $R_4$ is H, halogen, alkyl of 1 to 10 carbons, carbons, alkoxy of 1 to 10;

r is an integer having the values of 1 to 10;

s is an integer having the values 1 to 4;

represents a 5 or 6 membered heteroaryl ring having 1 to 3 heteroatoms selected from the group consisting of N, S and O, and t is an integer having the values 1 to 5.

* * * * *

UNITED STATES PATENT AND TRADEMARK OFFICE
CERTIFICATE OF CORRECTION

PATENT NO. : 6,720,423 B2
DATED : April 13, 2004
INVENTOR(S) : Vasudevan et al.

It is certified that error appears in the above-identified patent and that said Letters Patent is hereby corrected as shown below:

Title page,
Item [75], Inventors, "Roshanta" should be -- Roshantha --

Column 14,
Table 1, for the compound no. 38, "557" should be deleted after (102); after "306" on the next line, insert -- 557 --
Table 1, for the compound no. 32, "926" should be deleted after (105); after "66" on the next line, insert -- 926 --

Column 15,
Line 18, "Pa." should be -- Pennsylvania --

Column 27,
Line 45, "Acid" should be -- acid --

Column 28,
Line 15, "3,3-Dimethyl-5-F[(1S,2S)" should be -- 3,3-Dimethyl-5-[(1S,2S) --

Column 29,
Line 22, "1.41 (m, 11H)" should be -- 1.41 (m, 1H) --
Line 46, "Acid Ethyl Ester" should be -- acid ethyl ester --

Column 30,
Lines 8 and 29, "Acid" should be -- acid --
Line 59, "1.1 SM" should be -- 1.15M --

Column 31,
Line 29, "SM" should be -- 5M --
Line 55, "Acid Ethyl Ester" should be -- acid ethyl ester --

Column 34,
Line 25, "Acid Ethyl Ester" should be -- acid ethyl ester --

Column 36,
Line 31, "Acid Ethyl Ester" should be -- acid ethyl ester --
Line 53, "Acid" should be -- acid --

Column 38,
Line 33, "Acid Ethyl Ester" should be -- acid ethyl ester --

UNITED STATES PATENT AND TRADEMARK OFFICE
CERTIFICATE OF CORRECTION

PATENT NO. : 6,720,423 B2
DATED : April 13, 2004
INVENTOR(S) : Vasudevan et al.

It is certified that error appears in the above-identified patent and that said Letters Patent is hereby corrected as shown below:

Column 39,
Line 32, "7.21(d, 11H, J=2.0Hz)" should be -- 7.21(d, 1H, J=2.0Hz) --

Column 41,
Line 66, "7.49 (d, 11H, J=2.1Hz)" should be -- 7.49 (d, 1H, J=2.1Hz) --

Column 42,
Line 13, "Acid" should be -- acid --

Column 43,
Line 23, "5-r[1S, 2S)" should be -- 5-[1S, 2S) --
Line 40, "Acid Ethyl Ester" should be -- acid ethyl ester --
Line 62, "Acid" should be -- acid --

Column 44,
Line 67, "20.1m1" should be -- 2.1 ml --

Column 45,
Line 4, "NN" should be -- N,N --
Line 32, "JJ=11.4" should be -- J=11.4 --

Column 46,
Line 9, "Acid Ethyl Ester" should be -- acid ethyl ester --
Line 26, "Acid" should be -- acid --
Line 31, "tetrahydrofuran (2 nl)" should be -- tetrahydrofuran (2 ml) --
Line 34, "0.01 Ig" should be -- 0.011g --
Lines 64 and 65, "11H" should be -- 1H --

Column 50,
Line 5, "Acid" should be -- acid --
Line 32, "$0.1^2g$" should be -- 0.12g --

Column 51,
Line 28, "Acid" should be -- acid --
Line 63, "4 Edienoic" should be -- 4E-dienoic --

Column 52,
Line 6, "Acid" should be -- acid --

UNITED STATES PATENT AND TRADEMARK OFFICE
CERTIFICATE OF CORRECTION

PATENT NO. : 6,720,423 B2
DATED : April 13, 2004
INVENTOR(S) : Vasudevan et al.

It is certified that error appears in the above-identified patent and that said Letters Patent is hereby corrected as shown below:

Column 53,
Line 42, "SM" should be -- 5M --
Line 54, "Acid Ethyl Ether" should be -- acid ethyl ester --

Column 54,
Line 6, "benzofuran-5-]" should be -- benzofuran-5-yl] --
Line 17, "7.20 (d,11H,J=1.8Hz), 6.91 (d, 11H, J=1.8)" should be -- 7.20 (d, 1H,J=1.8Hz), 6.91 (d, 1H, J=1.8) --
Line 18, "6.24 (d, 11H, J=15.5Hz), 5.66 (s, 11H), 5.33 (dd, 11H" should be -- 6.24 (d, 1H, J=15.5Hz), 5.66 (s, 1H), 5.33 (dd, 1H --
Line 42, "(m,11H)" should be -- (m,1H) --
Line 57, "5.67 (s, 11H)" should be -- 5.67 (s, 1H) --
Line 58, "(dd, 11H, J=15.5, 10.0Hz), 4.29 (d, 11H, J=8.5Hz)" should be -- (dd, 1H, J=15.5, 10.0Hz), 4.29 (d, 1H, J=8.5Hz) --
Line 59, "11H, J=8.5Hz)" should be -- 1H, J=8.5Hz) --
Line 64, "Acid Ethyl Ester" should be -- acid ethyl ester --

Column 57,
Line 53, "Acid Ethyl Ester" should be -- acid ethyl ester --

Column 58,
Line 4, "Acid Ethyl Ester" should be -- acid ethyl ester --
Line 55, "Acid" should be -- acid --

Column 59,
Line 22, "Intermediate 800.18 g" should be -- Intermediate 80 0.18g --
Line 38, "1.11 mmol" should be -- 1.1mmol --

Column 60,
Line 18, "5-F(1S,2S)" should be -- 5-[(1S,2S) --
Line 38, "Acid Ethyl Ester" should be -- acid ethyl ester --

Column 61,
Line 30, "5.63 (s,11H)" should be -- 5.63 (s, 1H) --
Line 37, "2-r[33-Dimethyl" should be -- 2-[33-Dimethyl --

Column 63,
Line 12, "where V" should be -- where Y --
Line 14, "where is" should be -- where Y is --

UNITED STATES PATENT AND TRADEMARK OFFICE
CERTIFICATE OF CORRECTION

PATENT NO.    : 6,720,423 B2
DATED         : April 13, 2004
INVENTOR(S)   : Vasudevan et al.

It is certified that error appears in the above-identified patent and that said Letters Patent is hereby corrected as shown below:

<u>Column 65,</u>
Line 25, "heptyiphenyl" should be -- heptylphenyl --

Signed and Sealed this

Twenty-first Day of December, 2004

JON W. DUDAS
*Director of the United States Patent and Trademark Office*